United States Patent
Just et al.

(10) Patent No.: US 10,100,097 B2
(45) Date of Patent: Oct. 16, 2018

(54) GIP-GLP-1 DUAL AGONIST COMPOUNDS AND METHODS

(71) Applicant: Zealand Pharma A/S, Glostrup (DK)

(72) Inventors: Rasmus Just, Copenhagen (DK); Ditte Riber, Brønshøj (DK); Anne Pernille Tofteng Shelton, Valby (DK); Torben Østerlund, Lund (SE); Kate Hansen, Copenhagen Nv (DK); Lene Jessen, Glostrup (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 14/398,260

(22) PCT Filed: May 3, 2013

(86) PCT No.: PCT/EP2013/059319
§ 371 (c)(1),
(2) Date: Oct. 31, 2014

(87) PCT Pub. No.: WO2013/164483
PCT Pub. Date: Nov. 7, 2013

(65) Prior Publication Data
US 2015/0299281 A1  Oct. 22, 2015

Related U.S. Application Data

(60) Provisional application No. 61/642,439, filed on May 3, 2012, provisional application No. 61/765,561, filed on Feb. 15, 2013.

(51) Int. Cl.
*A61K 38/26* (2006.01)
*C07K 14/575* (2006.01)
*C07K 14/605* (2006.01)
*A61K 38/00* (2006.01)

(52) U.S. Cl.
CPC .......... *C07K 14/575* (2013.01); *C07K 14/605* (2013.01); *A61K 38/00* (2013.01)

(58) Field of Classification Search
CPC .................................................. C07K 14/575
See application file for complete search history.

(56) References Cited

U.S. PATENT DOCUMENTS

| | | | |
|---|---|---|---|
| 7,994,122 B2 | 8/2011 | Riber et al. | |
| 8,642,540 B2 | 2/2014 | Meier et al. | |
| 8,642,541 B2 | 2/2014 | Meier et al. | |
| 8,680,049 B2 | 3/2014 | Meier et al. | |
| 8,685,919 B2 | 4/2014 | Meier et al. | |
| 9,156,901 B2 | 10/2015 | Riber et al. | |
| 9,169,310 B2 | 10/2015 | Riber et al. | |
| 9,180,169 B2 | 11/2015 | Tolborg et al. | |
| 9,403,894 B2 | 8/2016 | Meier et al. | |
| 9,896,495 B2 | 2/2018 | Riber et al. | |
| 2005/0070469 A1 | 3/2005 | Bloom et al. | |
| 2010/0099601 A1 | 4/2010 | Weiss | |
| 2010/0190701 A1 | 7/2010 | Day et al. | |
| 2010/0240883 A1 | 9/2010 | Wu et al. | |
| 2011/0230397 A1 | 9/2011 | Carriero et al. | |
| 2011/0286981 A1 | 11/2011 | Meier et al. | |
| 2011/0286982 A1 | 11/2011 | Meier et al. | |
| 2011/0293586 A1 | 12/2011 | Meier et al. | |
| 2011/0293587 A1 | 12/2011 | Meier et al. | |
| 2012/0178670 A1 | 7/2012 | Riber et al. | |
| 2013/0053304 A1 | 2/2013 | Wang et al. | |
| 2013/0157929 A1 | 6/2013 | Riber et al. | |
| 2013/0157935 A1 | 6/2013 | Meier et al. | |
| 2013/0157953 A1 | 6/2013 | Petersen et al. | |
| 2013/0316941 A1 | 11/2013 | Hamprecht et al. | |
| 2014/0011733 A1 | 1/2014 | Fosgerau et al. | |
| 2014/0080757 A1 | 3/2014 | Tolborg et al. | |
| 2014/0127174 A1 | 5/2014 | Meier et al. | |
| 2014/0127175 A1 | 5/2014 | Meier et al. | |
| 2015/0080295 A1 | 3/2015 | Meier et al. | |
| 2015/0111817 A1 | 4/2015 | Riber et al. | |
| 2015/0111826 A1 | 4/2015 | Riber et al. | |
| 2015/0210744 A1 | 7/2015 | Riber et al. | |
| 2015/0299281 A1 | 10/2015 | Just et al. | |
| 2015/0322130 A1 | 11/2015 | DiMarchi et al. | |
| 2015/0376257 A1 | 12/2015 | Riber et al. | |
| 2016/0000883 A1 | 1/2016 | Fosgerau et al. | |
| 2016/0009777 A1 | 1/2016 | Tolborg et al. | |
| 2016/0120951 A1 | 5/2016 | Riber et al. | |

(Continued)

FOREIGN PATENT DOCUMENTS

| | | |
|---|---|---|
| CN | 101519446 A | 9/2009 |
| DE | 102008003566 A1 | 7/2009 |
| DE | 102008003568 A1 | 7/2009 |

(Continued)

OTHER PUBLICATIONS

Finan et al., 2016, Reappraisal of GIP Pharmacology for Metabolic Diseases, Trends in Molecular Medicine, 22(5): 359-376.*
Ebert et al., 1980, Gastric Inhibitory Polypeptide, Clinics in Gastroenterology, 9(3): 679-698.*
Matsurmoto et al., 2016, Plasma Incretin Levels and Dipeptidyl Peptidase-4 Activity in Patients with obstructive Sleep Apnea, AnnalsATS, 13(8): 1378-1387.*
Gault et al., "Administration of an acylated GLP-1 and GIP preparation provides added beneficial glucose-lowering and insulinotropic actions over single incretins in mice with Type 2 diabetes and obesity," Clin Sci (Lond). 121(3):107-17 (2011).
Green et al., "Structurally modified analogues of glucagon-like peptide-1 (GLP-1) and glucose-dependent insulinotropic polypeptide (GIP) as future antidiabetic agents," Curr Pharm Des. 10(29):3651-62 (2004).
International Search Report and Written Opinion for PCT/EP2013/059319, mailed Sep. 12, 2013 (12 pages).

(Continued)

*Primary Examiner* — Amber D Steele
(74) *Attorney, Agent, or Firm* — Clark & Elbing LLP

(57) ABSTRACT

The present invention relates to truncated GIP analogs which comprise one or more substitutions as compared to wild-type GIP and which may have the property of an altered, preferably increased GLP-1 activity, e.g. as assessed in in vitro efficacy assays. The invention provides GIP-GLP-1 dual agonist compounds and associated methods.

28 Claims, 10 Drawing Sheets

Specification includes a Sequence Listing.

(56) References Cited

U.S. PATENT DOCUMENTS

| | | |
|---|---|---|
| 2016/0304576 A1 | 10/2016 | Meier et al. |
| 2016/0347813 A1 | 12/2016 | Hamprecht et al. |

FOREIGN PATENT DOCUMENTS

| | | |
|---|---|---|
| EP | 0082731 A1 | 6/1983 |
| EP | 2025684 A1 | 2/2009 |
| JP | 2011-524418 A | 9/2011 |
| JP | 2012-511900 A | 5/2012 |
| WO | WO-98/08871 A1 | 3/1998 |
| WO | WO-98/11125 A1 | 3/1998 |
| WO | WO-98/11126 A1 | 3/1998 |
| WO | WO-99/25727 A2 | 5/1999 |
| WO | WO-99/46283 A1 | 9/1999 |
| WO | WO-00/34331 A2 | 6/2000 |
| WO | WO-00/55119 A1 | 9/2000 |
| WO | WO-00/55184 A1 | 9/2000 |
| WO | WO-01/04156 A1 | 1/2001 |
| WO | WO-03/022304 A1 | 3/2003 |
| WO | WO-03/053339 A2 | 7/2003 |
| WO | WO-03/053460 A1 | 7/2003 |
| WO | WO-2004/062685 A2 | 7/2004 |
| WO | WO-2004/096854 A2 | 11/2004 |
| WO | WO-2006/051110 A2 | 5/2006 |
| WO | WO-2006/097537 A2 | 9/2006 |
| WO | WO-2006/121860 A2 | 11/2006 |
| WO | WO-2006/134340 A2 | 12/2006 |
| WO | WO-2007/024899 A2 | 3/2007 |
| WO | WO-2007/056362 A2 | 5/2007 |
| WO | WO-2007/081824 A2 | 7/2007 |
| WO | WO-2007/100535 A2 | 9/2007 |
| WO | WO-2008/010101 A2 | 1/2008 |
| WO | WO-2008/071972 A1 | 6/2008 |
| WO | WO-2008/101017 A2 | 8/2008 |
| WO | WO-2008/152403 A1 | 12/2008 |
| WO | WO-2009/067636 A2 | 5/2009 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2010/002283 A9 | 1/2010 |
| WO | WO-2010/011439 A2 | 1/2010 |
| WO | WO-2010/014946 A2 | 2/2010 |
| WO | WO-2010/016940 A2 | 2/2010 |
| WO | WO-2010/029159 A1 | 3/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/080606 A1 | 7/2010 |
| WO | WO-2010/080609 A1 | 7/2010 |
| WO | WO-2010/148089 A1 | 12/2010 |
| WO | WO-2011/006497 A1 | 1/2011 |
| WO | WO-2011/080103 A1 | 7/2011 |
| WO | WO-2011/088837 A1 | 7/2011 |
| WO | WO-2011/094337 A1 | 8/2011 |
| WO | WO-2011/117417 A1 | 9/2011 |
| WO | WO-2011/119657 A1 | 9/2011 |
| WO | WO-2011/160630 A2 | 12/2011 |
| WO | WO-2011/160633 A1 | 12/2011 |
| WO | WO-2012/062803 A1 | 5/2012 |
| WO | WO-2012/062804 A1 | 5/2012 |
| WO | WO-2012/098462 A1 | 7/2012 |
| WO | WO-2012/130866 A1 | 10/2012 |
| WO | WO-2012/140117 A1 | 10/2012 |
| WO | WO-2012/150503 A2 | 11/2012 |
| WO | WO 2012/167744 A1 * | 12/2012 ............ A61K 38/22 |
| WO | WO-2013/041678 A1 | 3/2013 |
| WO | WO-2013/092703 A2 | 6/2013 |
| WO | WO-2013/164483 A1 | 11/2013 |
| WO | WO-2014/016300 A1 | 1/2014 |
| WO | WO-2014/041195 A1 | 3/2014 |
| WO | WO-2015/067715 A2 | 5/2015 |
| WO | WO-2015/124612 A1 | 8/2015 |
| WO | WO-2016/166289 A1 | 10/2016 |

OTHER PUBLICATIONS

Irwin et al., "Antidiabetic potential of two novel fatty acid derivatised, N-terminally modified analogues of glucose-dependent insulinotropic polypeptide (GIP): N-AcGIP(LysPAL16) and N-AcGIP(LysPAL37)," Biol Chem. 389(7):679-87 (2005).

Malde et al., "Understanding interactions of gastric inhibitory polypeptide (GIP) with its G-protein coupled receptor through NMR and molecular modeling," J Pept Sci. 13(5):287-300 (2007).

Manhart et al., "Structure-function analysis of a series of novel GIP analogues containing different helical length linkers," Biochemistry. 42(10):3081-8 (2003).

Runge et al., "Differential structural properties of GLP-1 and exendin-4 determine their relative affinity for the GLP-1 receptor N-terminal extracellular domain," Biochemistry. 46(19):5830-40 (2007).

Irwin et al., "GIP(Lys16PAL) and GIP(Lys37PAL): novel long-acting acylated analogues of glucose-dependent insulinotropic polypeptide with improved antidiabetic potential," J Med Chem. 49(3):1047-54 (2006).

First Examination Report for New Zealand Patent Application No. 702333, dated Jun. 2, 2016 (4 pages).

U.S. Appl. No. 14/843,047, dated May 5, 2016, Zealand Pharma A/S.

U.S. Appl. No. 60/132,018, Prickett et al.

Abbrecht et al., "Erythrocyte life-span in mice acclimatized to different degrees of hypoxia," J Appl Physiol. 32(4):443-445 (1972).

Adelhorst et al., "Structure-activity studies of glucagon-like peptide-1," J Biol Chem 269(9):6275-6278 (1994).

Ali et al., "Cardiomyocyte glucagon receptor signaling modulates outcomes in mice with experimental myocardial infarction," Mol Metab. 4(2):132-143 (2015).

Altschul et al., "Local alignment statistics," Methods Enzymol. 266:460-480 (1996).

Arnold, "Heart failure," <http://www.merckmanuals.com/home/heart_and_blood_vessel_disorders/heart_failure/heart_failure.html?qt=congestive heart failure&alt=sh>, retrieved on Feb. 8, 2015 (12 pages).

Authier et al., "Endosomal proteolysis of glucagon at neutral pH generates the bioactive degradation product miniglucagon-(19-29)," Endocrinology. 144(12):5353-5364 (2003).

Bell, "Heart failure: the frequent, forgotten, and often fatal complication of diabetes," Diabetes Care. 26(8):2433-41 (2003).

Blache et al., "Endopeptidase from rat liver membranes, which generates miniglucagon from glucagon," J Biol Chem. 268(29):21748-21753 (1993).

Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).

Chan et al., "Suppression of weight gain by glucagon in obese Zucker rats," Exp Mol Path. 40(3):320-327 (1984).

Cohen et al., "Oxyntomodulin suppresses appetite and reduces food intake in humans," J Clin Endocrinol Metab. 88(10):4696-4701 (2003).

Communication from the European Patent Office for European Patent Application No. 08875673.9, dated Jul. 4, 2012 (6 pages).

Dakin et al., "Oxyntomodulin inhibits food intake in the rat," Endocrinology. 142(10):4244-4250 (2001).

Dakin et al., "Peripheral oxyntomodulin reduces food intake and body weight gain in rats," Endocrinology. 145(6):2687-2695 (2004).

Day et al., "A new glucagon and GLP-1 co-agonist eliminates obesity in rodents," Nat Chem Biol. 5(10):749-757 (2009).

Delgado et al., "The uses and properties of PEG-linked proteins," Crit Rev Ther Drug Carrier Syst. 9(3,4):249-304 (1992).

Diamant et al., "Diabetic cardiomyopathy in uncomplicated type 2 diabetes is associated with the metabolic syndrome and systemic inflammation," Diabetologia 48(8):1669-70 (2005).

(56) References Cited

OTHER PUBLICATIONS

Druce et al., "Investigation of structure-activity relationships of Oxyntomodulin (Oxm) using Oxm analogs," Endocrinology. 150(4):1712-1721 (2009).
England et al., "Glucagon carboxyl-terminal derivatives: Preparation, purification and characterization," Biochemistry. 21(5):940-950 (1982).
European Search Report from European Patent Application No. 07016032.0, dated Jan. 28, 2008 (8 pages).
Francis et al., "PEGylation of cytokines and other therapeutic proteins and peptides: the importance of biological optimisation of coupling techniques," Int J Hematol. 68(1):1-18 (1998).
Frandsen et al., "Glucagon: structure-function relationships investigated by sequence deletions," Hoppe Seylers Z Physiol Chem. 362(6):665-677 (1981).
Gelfanov et al., Discovery and structural optimization of high affinity co-agonists at the glucagon and GLP-1 receptors. Understanding Biology Using Peptides. Sylvie E. Blondelle, 763-764 (2005).
Goldstein et al., "Effects of chronic heart failure on the capacity of glucagon to enhance contractility and adenyl cyclase activity of human papillary muscles," Circulation. 44(4):638-648 (1971).
Gombotz et al. "Biodegradable polymers for protein and peptide drug delivery," Bioconjug Chem. 6(4):332-351 (1995).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).
Hjorth et al., "Glucagon and glucagon-like peptide 1: Selective receptor recognition via distinct peptide epitopes," J Biol Chem. 269(48):30121-30124 (1994).
Hostrup et al., Modification of Peptides and Proteins. Delivery Technologies for Biopharmaceuticals: Peptides, Proteins, Nucleic Acids and Vaccines. Jorgensen, Nielsen, 171-91 (2009).
Hruby et al., "The design and biological activities of glucagon agonists and antagonists, and their use in examining the mechanisms of glucose action," Curr Med Chem—Imm, Endoc Metab Agents. 1(3):199-215 (2001).
Hudecz et al., "Synthesis, conformation, biodistribution, and in vitro cytotoxicity of daunomycin-branched polypeptide conjugates," Bioconjug Chem. 3(1):49-57 (1992).
International Preliminary Report on Patentability for PCT/EP2013/069286, dated Jan. 19, 2015 (40 pages).
International Preliminary Report on Patentability for PCT/GB2008/002041, dated Dec. 17, 2009 (7 pages).
International Search Report and Written Opinion for PCT/EP2013/065519, dated Dec. 6, 2013 (11 pages).
International Search Report and Written Opinion for PCT/EP2013/069286, dated Dec. 18, 2013 (16 pages).
International Search Report and Written Opinion for PCT/GB2008/004121, dated Jun. 30, 2009 (25 pages).
International Search Report and Written Opinion for PCT/GB2008/004130, dated Mar. 25, 2009 (17 pages).
International Search Report and Written Opinion for PCT/GB2008/004132, dated Jun. 10, 2009 (16 pages).
International Search Report for International Application No. PCT/DK2011/000067, dated Dec. 9, 2011 (4 pages).
International Search Report for International Application No. PCT/IB2012/000134, dated Jun. 25, 2012 (3 pages).
International Search Report for PCT/DK2011/000072, dated Dec. 6, 2011 (3 pages).
International Search Report for PCT/GB2008/002041, dated Sep. 9, 2008 (3 pages).
International Search Report for PCT/GB2008/004157, dated Jun. 4, 2009 (21 pages).
Jaya et al., "Mechanism of hypocholesterolemic action of glucagon," J Biosci. 12(2):111-4 (1987).
Joshi et al., "The estimation of glutaminyl deamidation and aspartyl cleavage rates in glucagon," Int J Pharm. 273(1-2):213-219 (2004).
Kallenbach et al., Role of the peptide bond in protein structure and folding. The Amide Linkage: Selected Structural Aspects in Chemistry, Biochemistry, and Materials Science. Greenberg, Breneman, Liebman, 599-625 (2000).
Knudsen et al., "Potent derivatives of glucagon-like peptide-1 with pharmacokinetic properties suitable for once daily administration," J Med Chem. 43(9):1664-1669 (2000).
Lefébvre, "The intriguing diversity of the glucagon gene products," Curr Diab Rep. 2(3):201-2 (2002).
Lvoff et al., "Glucagon in heart failure and in cardiogenic shock. Experience in 50 patients," Circulation. 45(3):534-42 (1972).
Madsen et al., "Structure-activity and protraction relationship of long-acting glucagon-like peptide-1 derivatives: importance of fatty acid length, polarity, and bulkiness," J Med Chem. 50(54):6126-6132 (2007).
McKee et al., "Receptor binding and adenylate cyclase activities of glucagon analogues modified in the N-terminal region," Biochemistry. 25(7):1650-1656 (1986).
Mehta, "Diabetic cardiomyopathy: insights into pathogenesis, diagnostic challenges, and therapeutic options," Intl J Pharm Sci Res. 3(10):3565-3576 (2012).
NCBI Blast for Accession No. 721913A, retrieved on Dec. 15, 2009 (1 page).
Pan et al., "Design of a long acting peptide functioning as both a glucagon-like peptide-1 receptor agonist and a glucagon receptor antagonist," J Biol Chem. 281(18):12506-12515 (2006).
Parlevliet et al., "CNT0736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Parlevliet et al., "Oxyntomodulin ameliorates glucose intolerance in mice fed a high-fat diet," Am J Physiol Endocrinol Metab. 294(1):E142-E147 (2008).
Pocai et al., "Glucagon-like peptide 1/glucagon receptor dual agonism reverses obesity in mice," Diabetes. 58(10):2258-66 (2009).
Pocai, "Glucagon signaling in the heart: activation or inhibition?," Mol Metab. 4(2):81-2 (2015).
Pratesi et al., "Poly-L-aspartic acid as a carrier for doxorubicin: a comparative in vivo study of free and polymer-bound drug," Br J Cancer. 52(6):841-848 (1985).
Protest of U.S. Appl. No. 12/664,534 Pursuant 37 CFR 1.291, dated Jan. 13, 2010 (14 pages).
Rose et al., "Insulin proteinase liberates from glucagon a fragment known to have enhanced activity against $Ca^{2+} + Mg^{2+}$-dependent ATPase," Biochem J. 256(3):847-51 (1988).
Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).
Unson et al., "Glucagon antagonists: contribution to binding and activity of the amino-terminal sequence 1-5, position 12, and the putative alpha-helical segment 19-27," J Biol Chem. 264(2):789-794 (1989).
Unson et al., "Identification of an essential serine residue in glucagon: implication for an active site triad," Proc Natl Acad Sci USA. 91(2):454-458 (1994).
Unson et al., "Positively charged residues at positions 12, 17, and 18 of glucagon ensure maximum biological potency," J Biol Chem. 273(17):10308-12 (1998).
Wermuth et al., "Glossary of terms used in medicinal chemistry," Pure & Appl Chem. 70(5):1129-43 (1998).
Written Opinion for PCT/DK2011/000072, dated Dec. 6, 2011 (6 pages).
Written Opinion for Singapore Application No. 201209089-0, dated Nov. 8, 2013 (10 pages).
Written Opinion of the International Searching Authority for PCT/GB2008/002041, dated Sep. 9, 2008 (6 pages).
Zalipsky, "Functionalized poly(ethylene glycol) for preparation of biologically relevant conjugates," Bioconjug Chem. 6(2):150-165 (1995).
Zhu et al.,"The role of dipeptidyl peptidase IV in the cleavage of glucagon family peptides: in vivo metabolism of pituitary adenylate cyclase activating polypeptide-(1-38)," J Biol Chem. 278(25):22418-22423 (2003).

(56) References Cited

OTHER PUBLICATIONS

Chabenne et al., "Optimization of the native glucagon sequence for medicinal purposes," J Diabetes Sci Technol. 4(6):1322-31 (2010).
Periasamy et al., "Molecular basis of diastolic dysfunction," Available in PMC Jul. 6, 2009, published in final edited form as: Heart Fail Clin. 4(1):13-21 (13 pages).
Yasgur, "Premature ventricle contractions in heart failure: a closer examination," http://www.thecardiologyadvisor.com/heart-failure/premature-ventricle-contractions-in-heart-failure/article/515445/, retrieved Sep. 10, 2017 (3 pages).
Office Action for Colombian Application No. 16089238, dated Sep. 13, 2017 (18 pages).
U.S. Appl. No. 15/852,458, filed Dec. 22, 2017 (55 pages).

* cited by examiner

Figure 2:
A
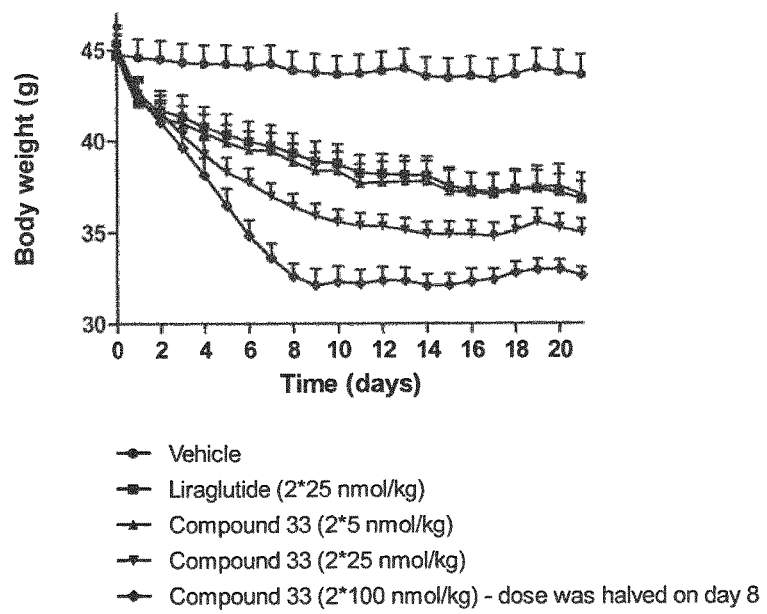
- Vehicle
- Liraglutide (2*25 nmol/kg)
- Compound 33 (2*5 nmol/kg)
- Compound 33 (2*25 nmol/kg)
- Compound 33 (2*100 nmol/kg) - dose was halved on day 8
B
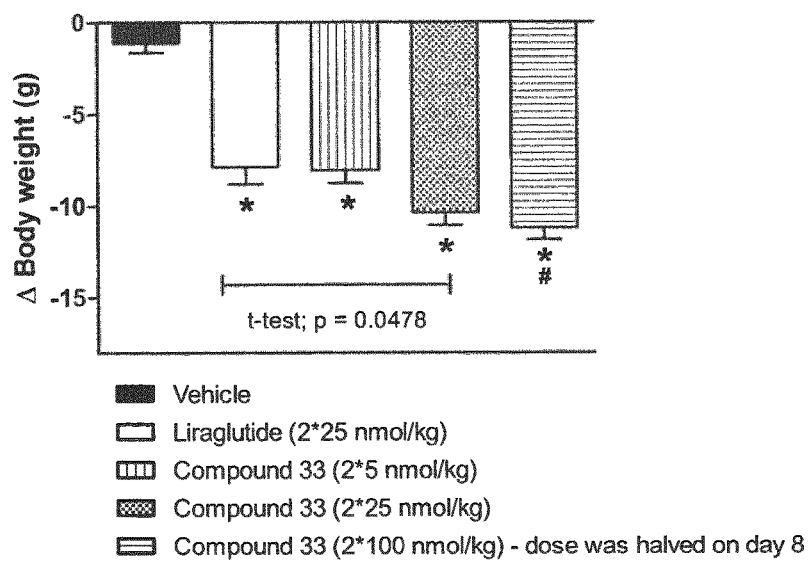
- Vehicle
- Liraglutide (2*25 nmol/kg)
- Compound 33 (2*5 nmol/kg)
- Compound 33 (2*25 nmol/kg)
- Compound 33 (2*100 nmol/kg) - dose was halved on day 8
*, $p < 0.05$ vs Vehicle
, $p < 0.05$ vs Liraglutide (2*25 nmol/kg)
One-way ANOVA followed by Tukey's multiple comparison tests Figure 3:
A

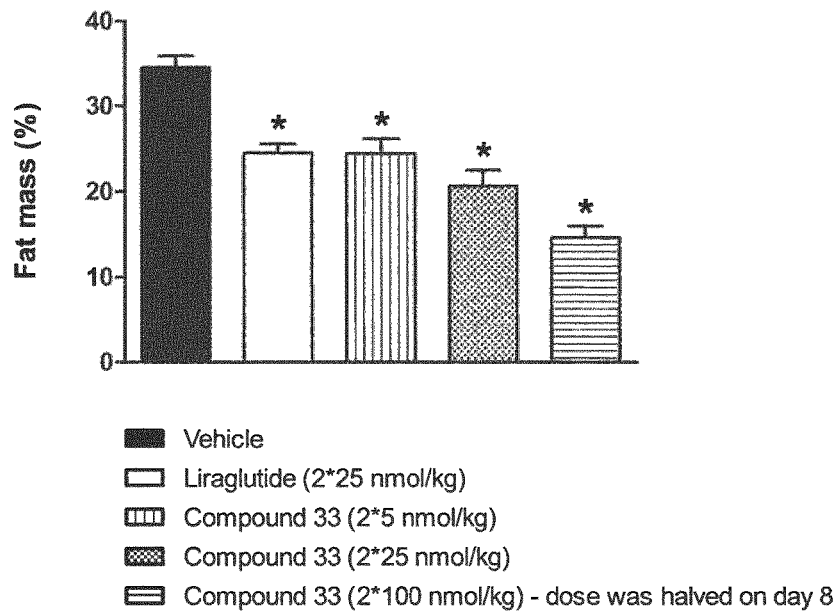

■ Vehicle
☐ Liraglutide (2*25 nmol/kg)
▥ Compound 33 (2*5 nmol/kg)
▨ Compound 33 (2*25 nmol/kg)
☰ Compound 33 (2*100 nmol/kg) - dose was halved on day 8

*, $p < 0.05$ vs Vehicle
One-way ANOVA; Tukey's multiple comparison tests

B

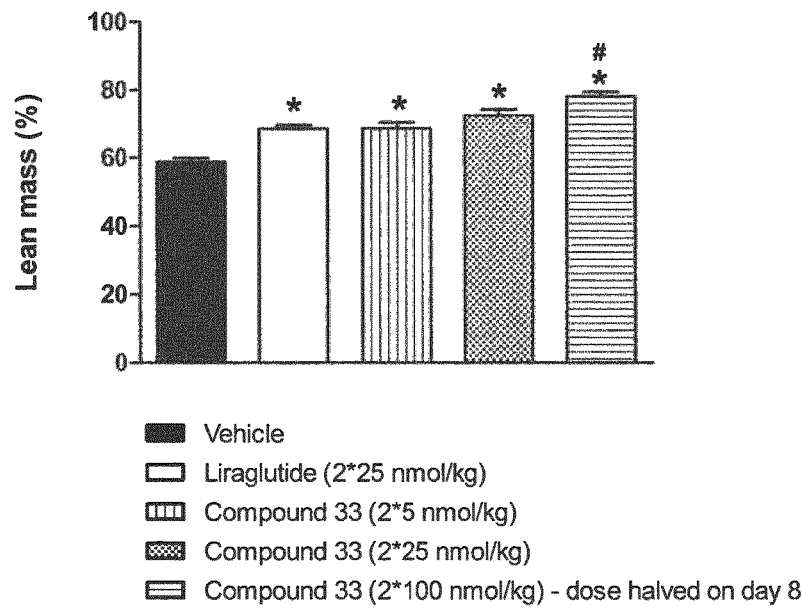

■ Vehicle
☐ Liraglutide (2*25 nmol/kg)
▥ Compound 33 (2*5 nmol/kg)
▨ Compound 33 (2*25 nmol/kg)
☰ Compound 33 (2*100 nmol/kg) - dose halved on day 8

*, $p < 0.05$ vs Vehicle
, $p < 0.05$ vs Liraglutide (2*25 nmol/kg)
One-way ANOVA; Tukey's multiple comparison tests Figure 5:
A

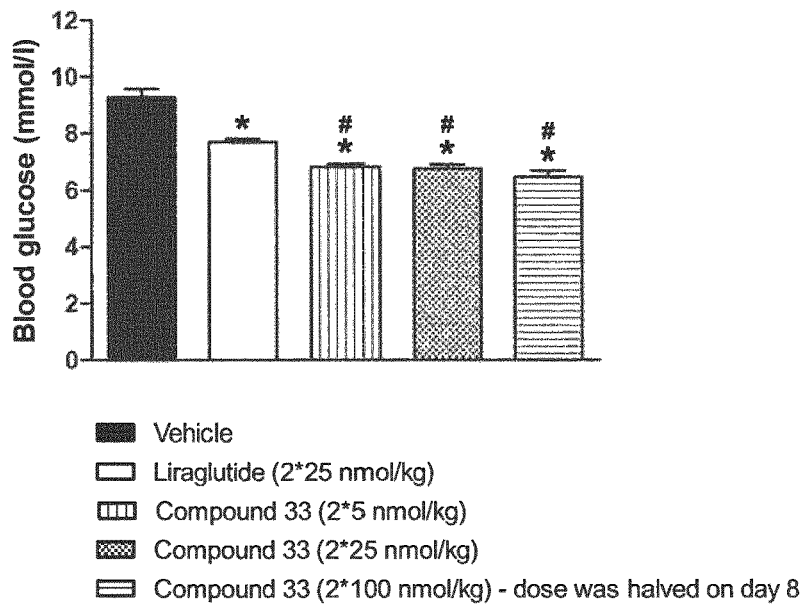

- Vehicle
- Liraglutide (2*25 nmol/kg)
- Compound 33 (2*5 nmol/kg)
- Compound 33 (2*25 nmol/kg)
- Compound 33 (2*100 nmol/kg) - dose was halved on day 8

*, $p < 0.05$ vs Vehicle
, $p < 0.05$ vs Liraglutide (2*25 nmol/kg)
One-way ANOVA; Tukey's multiple comparison tests

B

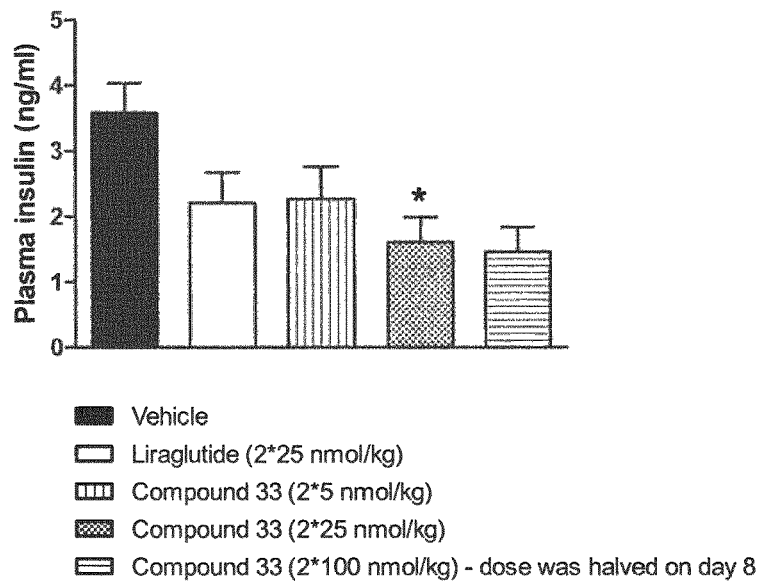

- Vehicle
- Liraglutide (2*25 nmol/kg)
- Compound 33 (2*5 nmol/kg)
- Compound 33 (2*25 nmol/kg)
- Compound 33 (2*100 nmol/kg) - dose was halved on day 8

*, $p < 0.05$ vs Vehicle
One-way ANOVA; Tukey's multiple comparison tests

Figure 6:
A
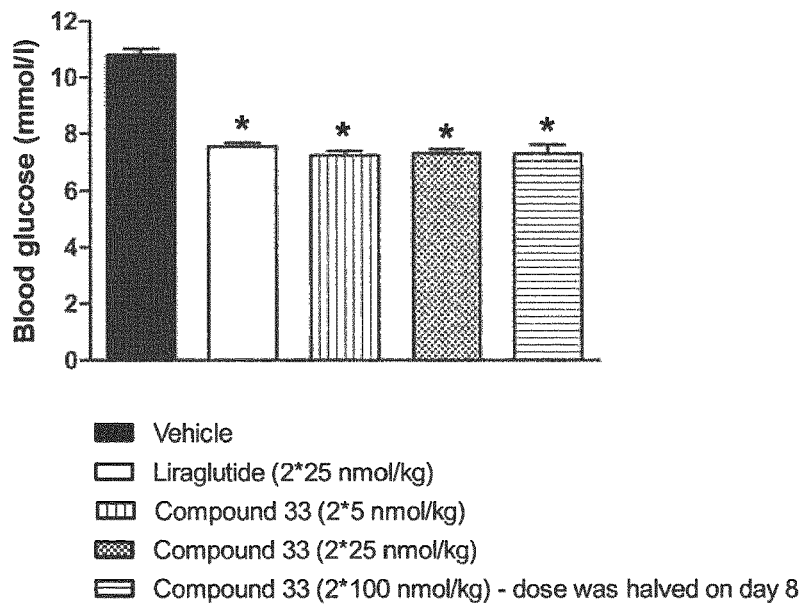
- Vehicle
- Liraglutide (2*25 nmol/kg)
- Compound 33 (2*5 nmol/kg)
- Compound 33 (2*25 nmol/kg)
- Compound 33 (2*100 nmol/kg) - dose was halved on day 8
*, $p < 0.05$ vs Vehicle
One-way ANOVA; Tukey's multiple comparison tests
B
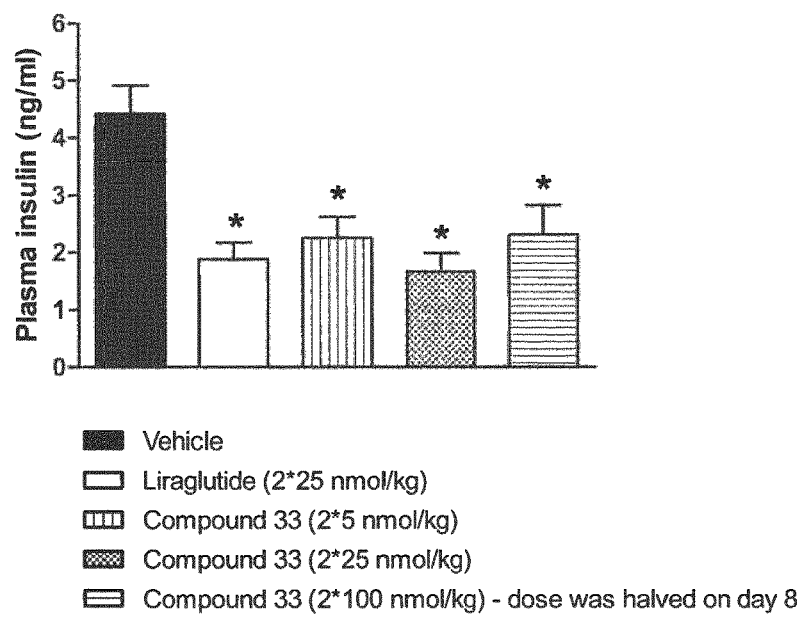
- Vehicle
- Liraglutide (2*25 nmol/kg)
- Compound 33 (2*5 nmol/kg)
- Compound 33 (2*25 nmol/kg)
- Compound 33 (2*100 nmol/kg) - dose was halved on day 8
*, $p < 0.05$ vs Vehicle
One-way ANOVA; Tukey's multiple comparison tests

A

■ Vehicle
☐ Liraglutide (2*25 nmol/kg)
▥ Compound 33 (2*5 nmol/kg)
▦ Compound 33 (2*25 nmol/kg)
☰ Compound 33 (2*100 nmol/kg) - dose was halved on day 8

*, p < 0.05 vs Vehicle
, p < 0.05 vs Liraglutide (2*25 nmol/kg)
One way ANOVA; Tukey's multiple comparison tests

SEQUENCE LISTING

```
<160> NUMBER OF SEQ ID NOS: 149

<210> SEQ ID NO 1
<211> LENGTH: 42
<212> TYPE: PRT
<213> ORGANISM: Artificial sequence
<220> FEATURE:
<223> OTHER INFORMATION: Synthetic sequence: GIP Analogue: General
      Formula I(b) of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: VARIANT
<222> LOCATION: (1)..(1)
<223> OTHER INFORMATION: Xaa is His or Tyr
<220> FEATURE:
<221> NAME/KEY: VARIANT
<222> LOCATION: (2)..(2)
<223> OTHER INFORMATION: Xaa is Ala, Aib or Gly
<220> FEATURE:
<221> NAME/KEY: VARIANT
<222> LOCATION: (3)..(3)
<223> OTHER INFORMATION: Xaa is Glu or Asp
<220> FEATURE:
<221> NAME/KEY: VARIANT
<222> LOCATION: (7)..(7)
<223> OTHER INFORMATION: Xaa is Thr or Ser
<220> FEATURE:
<221> NAME/KEY: VARIANT
<222> LOCATION: (9)..(9)
<223> OTHER INFORMATION: Xaa is Asp or Glu
<220> FEATURE:
<221> NAME/KEY: VARIANT
<222> LOCATION: (10)..(10)
<223> OTHER INFORMATION: Xaa is Tyr, Leu or Ser
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (14)..(14)
<223> OTHER INFORMATION: Xaa is Met, Leu or Ser
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Lys, Gly, Ser or Glu
<220> FEATURE:
<221> NAME/KEY: VARIANT
<222> LOCATION: (17)..(17)
<223> OTHER INFORMATION: Xaa is Ile, Lys, Gln, Arg or Glu
<220> FEATURE:
<221> NAME/KEY: VARIANT
<222> LOCATION: (19)..(19)
<223> OTHER INFORMATION: Xaa is Gln, Ala, Glu or Lys
<220> FEATURE:
<221> NAME/KEY: VARIANT
<222> LOCATION: (20)..(20)
```

```
<223> OTHER INFORMATION: Xaa is Gln, Lys or Arg
<220> FEATURE:
<221> NAME/KEY: VARIANT
<222> LOCATION: (21)..(21)
<223> OTHER INFORMATION: Xaa is Asp, Ala or Glu
<220> FEATURE:
<221> NAME/KEY: VARIANT
<222> LOCATION: (22)..(22)
<223> OTHER INFORMATION: Xaa is Phe or 1Nal
<220> FEATURE:
<221> NAME/KEY: VARIANT
<222> LOCATION: (23)..(23)
<223> OTHER INFORMATION: Xaa is Val, Ile or Leu
<220> FEATURE:
<221> NAME/KEY: VARIANT
<222> LOCATION: (24)..(24)
<223> OTHER INFORMATION: Xaa is Asn, Glu, Arg or Lys
<220> FEATURE:
<221> NAME/KEY: VARIANT
<222> LOCATION: (27)..(27)
<223> OTHER INFORMATION: Xaa is Leu, Val, Ile, Lys or Ser
<220> FEATURE:
<221> NAME/KEY: VARIANT
<222> LOCATION: (28)..(28)
<223> OTHER INFORMATION: Xaa is Ala or Aib
<220> FEATURE:
<221> NAME/KEY: VARIANT
<222> LOCATION: (29)..(29)
<223> OTHER INFORMATION: Xaa is Gln, Gly, Aib or Tyr
<220> FEATURE:
<221> NAME/KEY: VARIANT
<222> LOCATION: (30)..(30)
<223> OTHER INFORMATION: Xaa is Lys, Gly, Pro or absent
<220> FEATURE:
<221> NAME/KEY: VARIANT
<222> LOCATION: (31)..(31)
<223> OTHER INFORMATION: Xaa is Gly, Pro, Ser, Glu or absent
<220> FEATURE:
<221> NAME/KEY: VARIANT
<222> LOCATION: (32)..(32)
<223> OTHER INFORMATION: Xaa is Lys, Ser or absent
<220> FEATURE:
<221> NAME/KEY: VARIANT
<222> LOCATION: (33)..(33)
<223> OTHER INFORMATION: Xaa is Lys, Ser, Glu or absent
<220> FEATURE:
<221> NAME/KEY: VARIANT
<222> LOCATION: (34)..(34)
<223> OTHER INFORMATION: Xaa is Asn, Gly, Ala, Lys or absent
<220> FEATURE:
<221> NAME/KEY: VARIANT
<222> LOCATION: (35)..(35)
<223> OTHER INFORMATION: Xaa is Asp, Ala, Pro, Glu or absent
<220> FEATURE:
<221> NAME/KEY: VARIANT
<222> LOCATION: (36)..(36)
<223> OTHER INFORMATION: Xaa is Trp, Pro, Lys or absent
<220> FEATURE:
<221> NAME/KEY: VARIANT
<222> LOCATION: (37)..(37)
<223> OTHER INFORMATION: Xaa is Lys, Pro, Glu or absent
<220> FEATURE:
<221> NAME/KEY: VARIANT
<222> LOCATION: (38)..(38)
<223> OTHER INFORMATION: Xaa is His, Pro, Ser, Lys or absent
<220> FEATURE:
<221> NAME/KEY: VARIANT
<222> LOCATION: (39)..(39)
<223> OTHER INFORMATION: Xaa is Asn, Ser or absent
<220> FEATURE:
<221> NAME/KEY: VARIANT
<222> LOCATION: (40)..(40)
<223> OTHER INFORMATION: Xaa is Ile or absent
<220> FEATURE:
<221> NAME/KEY: VARIANT
<222> LOCATION: (41)..(41)
<223> OTHER INFORMATION: Xaa is Thr or absent
<220> FEATURE:
<221> NAME/KEY: VARIANT
```

<222> LOCATION: (42)..(42)
<223> OTHER INFORMATION: Xaa is Gln or absent

<400> SEQUENCE: 1

Xaa Xaa Xaa Gly Thr Phe Xaa Ser Xaa Xaa Ile Xaa Xaa Xaa Xaa
1               5                   10                  15

Xaa Ala Xaa Xaa Xaa Xaa Xaa Trp Leu Xaa Xaa Xaa Xaa Xaa
            20                  25                  30

Xaa Xaa Xaa Xaa Xaa Xaa Xaa Xaa Xaa Xaa
            35                  40

<210> SEQ ID NO 2
<211> LENGTH: 40
<212> TYPE: PRT
<213> ORGANISM: Artificial sequence
<220> FEATURE:
<223> OTHER INFORMATION: Synthetic sequence: GIP Analogue: General
      Formula II(b) of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (7)..(7)
<223> OTHER INFORMATION: Xaa is Thr or Ser
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (14)..(14)
<223> OTHER INFORMATION: Xaa is Leu
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Ile or Lys
<220> FEATURE:
<221> NAME/KEY: VARIANT
<222> LOCATION: (20)..(20)
<223> OTHER INFORMATION: Xaa is Lys or Arg
<220> FEATURE:
<221> NAME/KEY: VARIANT
<222> LOCATION: (21)..(21)
<223> OTHER INFORMATION: Xaa is Ala or Glu
<220> FEATURE:
<221> NAME/KEY: VARIANT
<222> LOCATION: (23)..(23)
<223> OTHER INFORMATION: Xaa is Val or Ile
<220> FEATURE:
<221> NAME/KEY: VARIANT
<222> LOCATION: (24)..(24)
<223> OTHER INFORMATION: Xaa is Asn or Glu
<220> FEATURE:
<221> NAME/KEY: VARIANT
<222> LOCATION: (27)..(27)
<223> OTHER INFORMATION: Xaa is Leu or Val
<220> FEATURE:
<221> NAME/KEY: VARIANT
<222> LOCATION: (29)..(29)
<223> OTHER INFORMATION: Xaa is Aib or Gly
<220> FEATURE:
<221> NAME/KEY: VARIANT
<222> LOCATION: (30)..(30)
<223> OTHER INFORMATION: Xaa is Lys, Gly or absent
<220> FEATURE:

```
<221> NAME/KEY: VARIANT
<222> LOCATION: (31)..(40)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 2

Tyr Ala Glu Gly Thr Phe Xaa Ser Asp Tyr Ser Ile Xaa Xaa Xaa Lys
1               5                   10                  15

Xaa Ala Gln Xaa Xaa Phe Xaa Xaa Trp Leu Xaa Ala Xaa Xaa Xaa Xaa
            20                  25                  30

Xaa Xaa Xaa Xaa Xaa Xaa Xaa Xaa
        35                  40

<210> SEQ ID NO 3
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib

<400> SEQUENCE: 3

Tyr Ala Glu Gly Thr Phe Ile Ser Asp Tyr Ser Ile Tyr Leu Glu Lys
1               5                   10                  15

Lys Ala Ala Lys Glu Phe Val Asn Trp Leu Leu Ala Gln Lys
            20                  25                  30

<210> SEQ ID NO 4
<211> LENGTH: 39
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(13)
<223> OTHER INFORMATION: Aib

<400> SEQUENCE: 4

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 5
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 5

Tyr Ala Glu Gly Thr Phe Thr Ser Asp Tyr Ser Ile Ala Leu Asp Lys
1               5                   10                  15

Ile Ala Gln Arg Ala Phe Val Asn Trp Leu Val Ala Ala Lys
            20                  25                  30
```

```
<210> SEQ ID NO 6
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib

<400> SEQUENCE: 6

Tyr Ala Glu Gly Thr Phe Ile Ser Asp Tyr Ser Ile Tyr Leu Glu Lys
1               5                   10                  15

Ile Ala Ala Lys Glu Phe Val Asn Trp Leu Leu Ala Gln Lys
            20                  25                  30

<210> SEQ ID NO 7
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 7

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala Lys
            20                  25                  30

<210> SEQ ID NO 8
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (29)..(29)
<223> OTHER INFORMATION: Aib

<400> SEQUENCE: 8

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala Lys
            20                  25                  30

<210> SEQ ID NO 9
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (29)..(29)
<223> OTHER INFORMATION: Aib

<400> SEQUENCE: 9

Tyr Gly Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala Lys
```

```
            20                  25                  30

<210> SEQ ID NO 10
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 10

Tyr Ala Glu Gly Thr Phe Ser Ser Asp Tyr Ser Ile Tyr Leu Asp Lys
1               5                   10                  15

Lys Ala Gln Arg Ala Phe Val Asn Trp Leu Leu Ala Ala Lys
            20                  25                  30

<210> SEQ ID NO 11
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 11

Tyr Ala Glu Gly Thr Phe Thr Ser Asp Leu Ser Ile Tyr Leu Asp Lys
1               5                   10                  15

Lys Ala Gln Arg Ala Phe Val Asn Trp Leu Leu Ala Ala Lys
            20                  25                  30

<210> SEQ ID NO 12
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 12

Tyr Ala Glu Gly Thr Phe Thr Ser Asp Ser Ser Ile Tyr Leu Asp Lys
1               5                   10                  15

Lys Ala Gln Arg Ala Phe Val Asn Trp Leu Leu Ala Ala Lys
            20                  25                  30

<210> SEQ ID NO 13
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 13

Tyr Ala Glu Gly Thr Phe Thr Ser Asp Tyr Leu Ile Tyr Leu Asp Lys
1               5                   10                  15
```

Lys Ala Gln Arg Ala Phe Val Asn Trp Leu Leu Ala Ala Lys
            20                  25                  30

<210> SEQ ID NO 14
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 14

Tyr Ala Glu Gly Thr Phe Thr Ser Asp Tyr Ser Ile Ala Leu Asp Lys
1               5                   10                  15

Lys Ala Gln Arg Ala Phe Val Asn Trp Leu Leu Ala Ala Lys
            20                  25                  30

<210> SEQ ID NO 15
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 15

Tyr Ala Glu Gly Thr Phe Thr Ser Asp Tyr Ser Ile Tyr Ser Asp Lys
1               5                   10                  15

Lys Ala Gln Arg Ala Phe Val Asn Trp Leu Leu Ala Ala Lys
            20                  25                  30

<210> SEQ ID NO 16
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 16

Tyr Ala Glu Gly Thr Phe Thr Ser Asp Tyr Ser Ile Tyr Leu Glu Lys
1               5                   10                  15

Lys Ala Gln Arg Ala Phe Val Asn Trp Leu Leu Ala Ala Lys
            20                  25                  30

<210> SEQ ID NO 17
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 17

Tyr Ala Glu Gly Thr Phe Thr Ser Asp Tyr Ser Ile Ala Leu Glu Lys
1               5                   10                  15

Lys Ala Gln Arg Ala Phe Val Asn Trp Leu Leu Ala Ala Lys
            20                  25                  30

<210> SEQ ID NO 18
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 18

Tyr Ala Glu Gly Thr Phe Thr Ser Asp Tyr Ser Ile Tyr Leu Asp Ser
1               5                   10                  15

Lys Ala Gln Arg Ala Phe Val Asn Trp Leu Leu Ala Ala Lys
            20                  25                  30

<210> SEQ ID NO 19
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 19

Tyr Ala Glu Gly Thr Phe Thr Ser Asp Tyr Ser Ile Tyr Leu Asp Glu
1               5                   10                  15

Lys Ala Gln Arg Ala Phe Val Asn Trp Leu Leu Ala Ala Lys
            20                  25                  30

<210> SEQ ID NO 20
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 20

Tyr Ala Glu Gly Thr Phe Thr Ser Asp Tyr Ser Ile Tyr Leu Asp Ser
1               5                   10                  15

Lys Ala Lys Arg Ala Phe Val Asn Trp Leu Leu Ala Ala Lys
            20                  25                  30

<210> SEQ ID NO 21
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 21

Tyr Ala Glu Gly Thr Phe Thr Ser Asp Tyr Ser Ile Tyr Leu Asp Lys

```
                1               5                   10                  15
Lys Ala Gln Lys Glu Phe Val Asn Trp Leu Leu Ala Ala Lys
            20                  25                  30

<210> SEQ ID NO 22
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 22

Tyr Ala Glu Gly Thr Phe Thr Ser Asp Tyr Ser Ile Tyr Leu Asp Lys
1               5                   10                  15

Lys Ala Gln Arg Ala Phe Val Lys Trp Leu Leu Ala Ala Lys
            20                  25                  30

<210> SEQ ID NO 23
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 23

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Val Ala Ala Lys
            20                  25                  30

<210> SEQ ID NO 24
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 24

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Ser Ala Ala Lys
            20                  25                  30

<210> SEQ ID NO 25
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 25
```

```
Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Lys Ala Ala Lys
            20                  25                  30

<210> SEQ ID NO 26
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 26

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Lys
            20                  25

<210> SEQ ID NO 27
<211> LENGTH: 36
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (33)..(33)
<223> OTHER INFORMATION: Xaa is 1Nal

<400> SEQUENCE: 27

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala Lys Tyr Gly
            20                  25                  30

Xaa Leu Asp Phe
        35

<210> SEQ ID NO 28
<211> LENGTH: 34
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (31)..(31)
<223> OTHER INFORMATION: Xaa is 1Nal

<400> SEQUENCE: 28

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Tyr Gly Xaa Leu
            20                  25                  30

Asp Phe
```

```
<210> SEQ ID NO 29
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 29

Tyr Ala Glu Gly Thr Phe Thr Ser Asp Tyr Ser Ile Tyr Leu Asp Lys
1               5                   10                  15

Lys Ala Glu Lys Ala Phe Val Asn Trp Leu Leu Ala Ala Lys
            20                  25                  30

<210> SEQ ID NO 30
<211> LENGTH: 39
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 30

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala Gly Pro Ser
            20                  25                  30

Ser Gly Ala Pro Pro Pro Ser
        35

<210> SEQ ID NO 31
<211> LENGTH: 38
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib

<400> SEQUENCE: 31

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala Gly Pro Ser
            20                  25                  30

Ser Gly Ala Pro Pro Ser
        35

<210> SEQ ID NO 32
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib

<400> SEQUENCE: 32
```

```
Tyr Ala Glu Gly Thr Phe Thr Ser Asp Tyr Ser Ile Tyr Leu Glu Lys
1               5                   10                  15

Lys Ala Ala Lys Glu Phe Val Asn Trp Leu Leu Ala Gln Lys
            20                  25                  30

<210> SEQ ID NO 33
<211> LENGTH: 42
<212> TYPE: PRT
<213> ORGANISM: Artificial sequence
<220> FEATURE:
<223> OTHER INFORMATION: Synthetic sequence: GIP Analogue: General
      Formula I(a) of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: VARIANT
<222> LOCATION: (1)..(1)
<223> OTHER INFORMATION: Xaa is His or Tyr
<220> FEATURE:
<221> NAME/KEY: VARIANT
<222> LOCATION: (2)..(2)
<223> OTHER INFORMATION: Xaa is Ala, Aib or Gly
<220> FEATURE:
<221> NAME/KEY: VARIANT
<222> LOCATION: (3)..(3)
<223> OTHER INFORMATION: Xaa is Glu or Asp
<220> FEATURE:
<221> NAME/KEY: VARIANT
<222> LOCATION: (7)..(7)
<223> OTHER INFORMATION: Xaa is Thr, Ser or Ile
<220> FEATURE:
<221> NAME/KEY: VARIANT
<222> LOCATION: (9)..(9)
<223> OTHER INFORMATION: Xaa is Asp or Glu
<220> FEATURE:
<221> NAME/KEY: VARIANT
<222> LOCATION: (10)..(10)
<223> OTHER INFORMATION: Xaa is Tyr, Leu or Ser
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (14)..(14)
<223> OTHER INFORMATION: Xaa is Met, Leu or Ser
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Lys, Gly, Ser or Glu
<220> FEATURE:
<221> NAME/KEY: VARIANT
<222> LOCATION: (17)..(17)
<223> OTHER INFORMATION: Xaa is Ile, Lys, Gln, Arg or Glu
<220> FEATURE:
<221> NAME/KEY: VARIANT
<222> LOCATION: (19)..(19)
<223> OTHER INFORMATION: Xaa is Gln, Ala, Glu or Lys
<220> FEATURE:
<221> NAME/KEY: VARIANT
<222> LOCATION: (20)..(20)
<223> OTHER INFORMATION: Xaa is Gln, Lys or Arg
<220> FEATURE:
<221> NAME/KEY: VARIANT
<222> LOCATION: (21)..(21)
<223> OTHER INFORMATION: Xaa is Asp, Ala or Glu
```

```
<220> FEATURE:
<221> NAME/KEY: VARIANT
<222> LOCATION: (22)..(22)
<223> OTHER INFORMATION: Xaa is Phe or 1Nal
<220> FEATURE:
<221> NAME/KEY: VARIANT
<222> LOCATION: (23)..(23)
<223> OTHER INFORMATION: Xaa is Val, Ile or Leu
<220> FEATURE:
<221> NAME/KEY: VARIANT
<222> LOCATION: (24)..(24)
<223> OTHER INFORMATION: Xaa is Asn, Glu, Arg or Lys
<220> FEATURE:
<221> NAME/KEY: VARIANT
<222> LOCATION: (27)..(27)
<223> OTHER INFORMATION: Xaa is Leu, Val, Ile, Lys, Glu or Ser
<220> FEATURE:
<221> NAME/KEY: VARIANT
<222> LOCATION: (28)..(28)
<223> OTHER INFORMATION: Xaa is Ala, Ser, Arg or Aib
<220> FEATURE:
<221> NAME/KEY: VARIANT
<222> LOCATION: (29)..(29)
<223> OTHER INFORMATION: Xaa is Gln, Aib, Glu, Lys or Tyr
<220> FEATURE:
<221> NAME/KEY: VARIANT
<222> LOCATION: (30)..(30)
<223> OTHER INFORMATION: Xaa is Lys, Gly, Pro or absent
<220> FEATURE:
<221> NAME/KEY: VARIANT
<222> LOCATION: (31)..(31)
<223> OTHER INFORMATION: Xaa is Gly, Pro, Ser, Glu or absent
<220> FEATURE:
<221> NAME/KEY: VARIANT
<222> LOCATION: (32)..(32)
<223> OTHER INFORMATION: Xaa is Lys, Ser or absent
<220> FEATURE:
<221> NAME/KEY: VARIANT
<222> LOCATION: (33)..(33)
<223> OTHER INFORMATION: Xaa is Lys, Ser, Glu or absent
<220> FEATURE:
<221> NAME/KEY: VARIANT
<222> LOCATION: (34)..(34)
<223> OTHER INFORMATION: Xaa is Asn, Gly, Ala, Lys or absent
<220> FEATURE:
<221> NAME/KEY: VARIANT
<222> LOCATION: (35)..(35)
<223> OTHER INFORMATION: Xaa is Asp, Ala, Pro, Glu or absent
<220> FEATURE:
<221> NAME/KEY: VARIANT
<222> LOCATION: (36)..(36)
<223> OTHER INFORMATION: Xaa is Trp, Pro, Lys or absent
<220> FEATURE:
<221> NAME/KEY: VARIANT
<222> LOCATION: (37)..(37)
<223> OTHER INFORMATION: Xaa is Lys, Pro, Glu or absent
<220> FEATURE:
<221> NAME/KEY: VARIANT
<222> LOCATION: (38)..(38)
<223> OTHER INFORMATION: Xaa is His, Pro, Ser, Lys or absent
<220> FEATURE:
<221> NAME/KEY: VARIANT
<222> LOCATION: (39)..(39)
<223> OTHER INFORMATION: Xaa is Asn, Ser or absent
<220> FEATURE:
<221> NAME/KEY: VARIANT
<222> LOCATION: (40)..(40)
<223> OTHER INFORMATION: Xaa is Ile or absent
<220> FEATURE:
<221> NAME/KEY: VARIANT
<222> LOCATION: (41)..(41)
<223> OTHER INFORMATION: Xaa is Thr or absent
<220> FEATURE:
<221> NAME/KEY: VARIANT
<222> LOCATION: (42)..(42)
<223> OTHER INFORMATION: Xaa is Gln or absent

<400> SEQUENCE: 33
```

```
Xaa Xaa Xaa Gly Thr Phe Xaa Ser Xaa Xaa Ile Xaa Xaa Xaa Xaa
1               5                   10                  15

Xaa Ala Xaa Xaa Xaa Xaa Xaa Xaa Trp Leu Xaa Xaa Xaa Xaa Xaa
        20                  25                  30

Xaa Xaa Xaa Xaa Xaa Xaa Xaa Xaa Xaa Xaa
        35                  40

<210> SEQ ID NO 34
<211> LENGTH: 40
<212> TYPE: PRT
<213> ORGANISM: Artificial sequence
<220> FEATURE:
<223> OTHER INFORMATION: Synthetic sequence: GIP Analogue: General
      Formula II(a) of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: VARIANT
<222> LOCATION: (2)..(2)
<223> OTHER INFORMATION: Xaa is Aib or Gly
<220> FEATURE:
<221> NAME/KEY: VARIANT
<222> LOCATION: (7)..(7)
<223> OTHER INFORMATION: Xaa is Thr, Ile or Ser
<220> FEATURE:
<221> NAME/KEY: VARIANT
<222> LOCATION: (10)..(10)
<223> OTHER INFORMATION: Xaa is Tyr, Leu or Ser
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (14)..(14)
<223> OTHER INFORMATION: Xaa is Leu
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Ser, Glu or Lys
<220> FEATURE:
<221> NAME/KEY: VARIANT
<222> LOCATION: (17)..(17)
<223> OTHER INFORMATION: Xaa is Ile or Lys
<220> FEATURE:
<221> NAME/KEY: VARIANT
<222> LOCATION: (19)..(19)
<223> OTHER INFORMATION: Xaa is Gln, Lys, Ala or Glu
<220> FEATURE:
<221> NAME/KEY: VARIANT
<222> LOCATION: (20)..(20)
<223> OTHER INFORMATION: Xaa is Lys or Arg
<220> FEATURE:
<221> NAME/KEY: VARIANT
<222> LOCATION: (21)..(21)
<223> OTHER INFORMATION: Xaa is Ala or Glu
<220> FEATURE:
<221> NAME/KEY: VARIANT
<222> LOCATION: (23)..(23)
<223> OTHER INFORMATION: Xaa is Val or Ile
<220> FEATURE:
<221> NAME/KEY: VARIANT
<222> LOCATION: (24)..(24)
<223> OTHER INFORMATION: Xaa is Asn or Glu
<220> FEATURE:
<221> NAME/KEY: VARIANT
```

-continued

```
<222> LOCATION: (27)..(27)
<223> OTHER INFORMATION: Xaa is Leu, Glu, Ser, Lys or Val
<220> FEATURE:
<221> NAME/KEY: VARIANT
<222> LOCATION: (28)..(28)
<223> OTHER INFORMATION: Xaa is Aib, Ala, Ser or Arg
<220> FEATURE:
<221> NAME/KEY: VARIANT
<222> LOCATION: (29)..(29)
<223> OTHER INFORMATION: Xaa is Aib, Glu or Lys
<220> FEATURE:
<221> NAME/KEY: VARIANT
<222> LOCATION: (30)..(30)
<223> OTHER INFORMATION: Xaa is Lys, Gly or absent
<220> FEATURE:
<221> NAME/KEY: VARIANT
<222> LOCATION: (31)..(40)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 34

Tyr Xaa Glu Gly Thr Phe Xaa Ser Asp Xaa Xaa Ile Xaa Xaa Xaa Xaa
1               5                   10                  15

Xaa Ala Xaa Xaa Xaa Phe Xaa Xaa Trp Leu Xaa Xaa Xaa Xaa Xaa Xaa
            20                  25                  30

Xaa Xaa Xaa Xaa Xaa Xaa Xaa Xaa
        35                  40

<210> SEQ ID NO 35
<211> LENGTH: 30
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys(15-carboxy-pentadecanoyl-isoGlu)

<400> SEQUENCE: 35

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala Lys
            20                  25                  30

<210> SEQ ID NO 36
<211> LENGTH: 39
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(13)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 36

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln Gly Pro Ser
            20                  25                  30
```

Ser Gly Ala Pro Pro Ser
        35

<210> SEQ ID NO 37
<211> LENGTH: 39
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 37

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Ser
        35

<210> SEQ ID NO 38
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 38

Tyr Ala Glu Gly Thr Phe Thr Ser Asp Tyr Ser Ile Tyr Leu Asp Glu
1               5                   10                  15

Lys Ala Ala Lys Glu Phe Ile Glu Trp Leu Glu Ser Ala
            20                  25

<210> SEQ ID NO 39
<211> LENGTH: 39
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 39

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala Lys Pro Ser
            20                  25                  30

Ser Gly Ala Pro Pro Pro Ser
        35

<210> SEQ ID NO 40
<211> LENGTH: 39
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 40

Tyr Ala Glu Gly Thr Phe Thr Ser Asp Tyr Ser Ile Ala Leu Asp Lys
1               5                   10                  15

Lys Ala Gln Arg Ala Phe Val Asn Trp Leu Val Ala Ala Lys Pro Ser
            20                  25                  30

Ser Gly Ala Pro Pro Pro Ser
        35

<210> SEQ ID NO 41
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib

<400> SEQUENCE: 41

Tyr Ala Glu Gly Thr Phe Thr Ser Asp Tyr Ser Ile Tyr Leu Glu Lys
1               5                   10                  15

Lys Ala Ala Lys Asp Phe Val Glu Trp Leu Leu Ser Ala
            20                  25

<210> SEQ ID NO 42
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib

<400> SEQUENCE: 42

Tyr Ala Glu Gly Thr Phe Thr Ser Asp Tyr Ser Ile Tyr Leu Glu Lys
1               5                   10                  15

Lys Ala Gln Lys Glu Phe Val Glu Trp Leu Leu Ser Ala
            20                  25

<210> SEQ ID NO 43
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES -continued
<222> LOCATION: (2)..(2)
<223> OTHER INFORMATION: Aib

<400> SEQUENCE: 43

Tyr Ala Glu Gly Thr Phe Thr Ser Asp Tyr Ser Ile Tyr Leu Asp Glu
1               5                   10                  15

Lys Ala Ala Lys Asp Phe Val Glu Trp Leu Leu Ser Ala
            20                  25

<210> SEQ ID NO 44
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib

<400> SEQUENCE: 44

Tyr Ala Glu Gly Thr Phe Thr Ser Asp Tyr Ser Ile Tyr Leu Glu Ser
1               5                   10                  15

Lys Ala Ala His Asp Phe Val Glu Trp Leu Leu Ser Ala
            20                  25

<210> SEQ ID NO 45
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib

<400> SEQUENCE: 45

Tyr Ala Glu Gly Thr Phe Thr Ser Asp Tyr Ser Ile Tyr Leu Asp Lys
1               5                   10                  15

Lys Ala Ala His Asp Phe Val Glu Trp Leu Leu Ser Ala
            20                  25

<210> SEQ ID NO 46
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib

<400> SEQUENCE: 46

Tyr Ala Glu Gly Thr Phe Thr Ser Asp Tyr Ser Ile Tyr Leu Glu Lys
1               5                   10                  15

Lys Ala Ala Lys Glu Phe Val Glu Trp Leu Leu Ser Ala
            20                  25

<210> SEQ ID NO 47
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:

```
<221> NAME/KEY: MOD_RES
<222> LOCATION: (2)..(2)
<223> OTHER INFORMATION: Aib

<400> SEQUENCE: 47

Tyr Ala Glu Gly Thr Phe Thr Ser Asp Tyr Ser Ile Tyr Leu Asp Ser
1               5                   10                  15

Lys Ala Ala His Asp Phe Val Glu Trp Leu Leu Arg Ala
            20                  25

<210> SEQ ID NO 48
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 48

Tyr Ala Glu Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 49
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 49

Tyr Ala Glu Gly Thr Phe Thr Ser Asp Tyr Ser Ile Tyr Leu Glu Lys
1               5                   10                  15

Lys Ala Ala Lys Glu Phe Val Glu Trp Leu Leu Ser Ala
            20                  25

<210> SEQ ID NO 50
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 50

Tyr Ala Glu Gly Thr Phe Thr Ser Asp Tyr Ser Ile Tyr Leu Asp Ser
```

```
                1               5                   10                  15
Lys Ala Ala His Asp Phe Val Glu Trp Leu Leu Arg Ala
            20                  25
```

<210> SEQ ID NO 51
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 51

```
Tyr Ala Glu Gly Thr Phe Thr Ser Asp Tyr Ser Ile Tyr Leu Asp Glu
1               5                   10                  15
Lys Ala Ala Lys Asp Phe Val Glu Trp Leu Glu Ser Ala
            20                  25
```

<210> SEQ ID NO 52
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 52

```
Tyr Ala Glu Gly Thr Phe Thr Ser Asp Tyr Ser Lys Tyr Leu Asp Glu
1               5                   10                  15
Lys Ala Ala Lys Asp Phe Ile Glu Trp Leu Glu Ser Ala
            20                  25
```

<210> SEQ ID NO 53
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 53

```
Tyr Ala Glu Gly Thr Phe Thr Ser Asp Tyr Ser Ile Tyr Leu Asp Glu
1               5                   10                  15
Lys Ala Ala Lys Asp Phe Ile Glu Trp Leu Glu Ser Ala
            20                  25
```

<210> SEQ ID NO 54

-continued

```
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 54

Tyr Ala Glu Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 55
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 55

Tyr Ala Glu Gly Thr Phe Thr Ser Asp Tyr Ser Ile Tyr Leu Asp Glu
1               5                   10                  15

Lys Ala Ala Lys Asp Phe Val Glu Trp Leu Leu Ser Ala
            20                  25

<210> SEQ ID NO 56
<211> LENGTH: 39
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 56

Tyr Ala Glu Gly Thr Phe Thr Ser Asp Tyr Ser Ile Tyr Leu Asp Ser
1               5                   10                  15

Lys Ala Ala His Asp Phe Val Glu Trp Leu Leu Ser Ala Gly Pro Ser
            20                  25                  30

Ser Gly Ala Pro Pro Pro Ser
        35

<210> SEQ ID NO 57
<211> LENGTH: 39
<212> TYPE: PRT
<213> ORGANISM: Artificial sequence
<220> FEATURE:
```

<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys(Hexadecanoyl-isoGlu)

<400> SEQUENCE: 57

Tyr Ala Glu Gly Thr Phe Thr Ser Asp Tyr Ser Ile Tyr Leu Glu Lys
1               5                   10                  15

Lys Ala Ala Lys Glu Phe Val Glu Trp Leu Leu Ser Ala Gly Pro Ser
            20                  25                  30

Ser Gly Ala Pro Pro Pro Ser
        35

<210> SEQ ID NO 58
<211> LENGTH: 39
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib

<400> SEQUENCE: 58

Tyr Ala Glu Gly Thr Phe Thr Ser Asp Tyr Ser Ile Tyr Leu Asp Ser
1               5                   10                  15

Lys Ala Ala His Asp Phe Val Glu Trp Leu Leu Ser Ala Gly Pro Ser
            20                  25                  30

Ser Gly Ala Pro Pro Pro Ser
        35

<210> SEQ ID NO 59
<211> LENGTH: 42
<212> TYPE: PRT
<213> ORGANISM: Artificial sequence
<220> FEATURE:
<223> OTHER INFORMATION: Synthetic sequence: GIP Analogue: General
      Formula I of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: VARIANT
<222> LOCATION: (1)..(1)
<223> OTHER INFORMATION: Xaa is His or Tyr
<220> FEATURE:
<221> NAME/KEY: VARIANT
<222> LOCATION: (2)..(2)
<223> OTHER INFORMATION: Xaa is Ala, Aib or Gly
<220> FEATURE:
<221> NAME/KEY: VARIANT
<222> LOCATION: (3)..(3)
<223> OTHER INFORMATION: Xaa is Glu or Asp
<220> FEATURE:
<221> NAME/KEY: VARIANT
<222> LOCATION: (7)..(7)
<223> OTHER INFORMATION: Xaa is Thr, Ser or Ile
<220> FEATURE:
<221> NAME/KEY: VARIANT
<222> LOCATION: (9)..(9)
<223> OTHER INFORMATION: Xaa is Asp or Glu
<220> FEATURE:
<221> NAME/KEY: VARIANT
<222> LOCATION: (10)..(10)

```
<223> OTHER INFORMATION: Xaa is Tyr, Leu or Ser
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (14)..(14)
<223> OTHER INFORMATION: Xaa is Met, Leu or Ser
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Lys, Gly, Ser or Glu
<220> FEATURE:
<221> NAME/KEY: VARIANT
<222> LOCATION: (17)..(17)
<223> OTHER INFORMATION: Xaa is Ile, Lys, Gln, Arg or Glu
<220> FEATURE:
<221> NAME/KEY: VARIANT
<222> LOCATION: (19)..(19)
<223> OTHER INFORMATION: Xaa is Gln, Ala, Glu or Lys
<220> FEATURE:
<221> NAME/KEY: VARIANT
<222> LOCATION: (20)..(20)
<223> OTHER INFORMATION: Xaa is Gln, Lys or Arg
<220> FEATURE:
<221> NAME/KEY: VARIANT
<222> LOCATION: (21)..(21)
<223> OTHER INFORMATION: Xaa is Asp, Ala or Glu
<220> FEATURE:
<221> NAME/KEY: VARIANT
<222> LOCATION: (22)..(22)
<223> OTHER INFORMATION: Xaa is Phe or 1Nal
<220> FEATURE:
<221> NAME/KEY: VARIANT
<222> LOCATION: (23)..(23)
<223> OTHER INFORMATION: Xaa is Val, Ile or Leu
<220> FEATURE:
<221> NAME/KEY: VARIANT
<222> LOCATION: (24)..(24)
<223> OTHER INFORMATION: Xaa is Asn, Glu, Arg or Lys
<220> FEATURE:
<221> NAME/KEY: VARIANT
<222> LOCATION: (27)..(27)
<223> OTHER INFORMATION: Xaa is Leu, Val, Ile, Lys, Glu or Ser
<220> FEATURE:
<221> NAME/KEY: VARIANT
<222> LOCATION: (28)..(28)
<223> OTHER INFORMATION: Xaa is Ala, Ser, Arg or Aib
<220> FEATURE:
<221> NAME/KEY: VARIANT
<222> LOCATION: (29)..(29)
<223> OTHER INFORMATION: Xaa is Gln, Aib, Glu, Lys, Gly or Tyr
<220> FEATURE:
<221> NAME/KEY: VARIANT
<222> LOCATION: (30)..(30)
<223> OTHER INFORMATION: Xaa is Lys, Gly, Pro or absent
<220> FEATURE:
<221> NAME/KEY: VARIANT
<222> LOCATION: (31)..(31)
<223> OTHER INFORMATION: Xaa is Gly, Pro, Ser, Glu or absent
<220> FEATURE:
<221> NAME/KEY: VARIANT
<222> LOCATION: (32)..(32)
<223> OTHER INFORMATION: Xaa is Lys, Ser or absent
<220> FEATURE:
<221> NAME/KEY: VARIANT
<222> LOCATION: (33)..(33)
<223> OTHER INFORMATION: Xaa is Lys, Ser, Glu or absent
<220> FEATURE:
<221> NAME/KEY: VARIANT
```

```
<222> LOCATION: (34)..(34)
<223> OTHER INFORMATION: Xaa is Asn, Gly, Ala, Lys or absent
<220> FEATURE:
<221> NAME/KEY: VARIANT
<222> LOCATION: (35)..(35)
<223> OTHER INFORMATION: Xaa is Asp, Ala, Pro, Glu or absent
<220> FEATURE:
<221> NAME/KEY: VARIANT
<222> LOCATION: (36)..(36)
<223> OTHER INFORMATION: Xaa is Trp, Pro, Lys or absent
<220> FEATURE:
<221> NAME/KEY: VARIANT
<222> LOCATION: (37)..(37)
<223> OTHER INFORMATION: Xaa is Lys, Pro, Glu or absent
<220> FEATURE:
<221> NAME/KEY: VARIANT
<222> LOCATION: (38)..(38)
<223> OTHER INFORMATION: Xaa is His, Pro, Ser, Lys or absent
<220> FEATURE:
<221> NAME/KEY: VARIANT
<222> LOCATION: (39)..(39)
<223> OTHER INFORMATION: Xaa is Asn, Ser or absent
<220> FEATURE:
<221> NAME/KEY: VARIANT
<222> LOCATION: (40)..(40)
<223> OTHER INFORMATION: Xaa is Ile or absent
<220> FEATURE:
<221> NAME/KEY: VARIANT
<222> LOCATION: (41)..(41)
<223> OTHER INFORMATION: Xaa is Thr or absent
<220> FEATURE:
<221> NAME/KEY: VARIANT
<222> LOCATION: (42)..(42)
<223> OTHER INFORMATION: Xaa is Gln or absent

<400> SEQUENCE: 59

Xaa Xaa Xaa Gly Thr Phe Xaa Ser Xaa Xaa Xaa Ile Xaa Xaa Xaa Xaa
1               5                   10                  15

Xaa Ala Xaa Xaa Xaa Xaa Xaa Xaa Trp Leu Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 60
<211> LENGTH: 40
<212> TYPE: PRT
<213> ORGANISM: Artificial sequence
<220> FEATURE:
<223> OTHER INFORMATION: Synthetic sequence: GIP Analogue: General
      Formula II of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: VARIANT
<222> LOCATION: (2)..(2)
<223> OTHER INFORMATION: Xaa is Aib or Gly
<220> FEATURE:
<221> NAME/KEY: VARIANT
<222> LOCATION: (7)..(7)
<223> OTHER INFORMATION: Xaa is Thr, Ile or Ser
<220> FEATURE:
<221> NAME/KEY: VARIANT
<222> LOCATION: (10)..(10)
<223> OTHER INFORMATION: Xaa is Tyr, Leu or Ser
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (13)..(13)
<223> OTHER INFORMATION: Xaa is Ala, Tyr or Aib
<220> FEATURE:
```

-continued

```
<221> NAME/KEY: VARIANT
<222> LOCATION: (14)..(14)
<223> OTHER INFORMATION: Xaa is Leu
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Ser, Glu or Lys
<220> FEATURE:
<221> NAME/KEY: VARIANT
<222> LOCATION: (17)..(17)
<223> OTHER INFORMATION: Xaa is Ile or Lys
<220> FEATURE:
<221> NAME/KEY: VARIANT
<222> LOCATION: (19)..(19)
<223> OTHER INFORMATION: Xaa is Gln, Lys, Ala or Glu
<220> FEATURE:
<221> NAME/KEY: VARIANT
<222> LOCATION: (20)..(20)
<223> OTHER INFORMATION: Xaa is Lys or Arg
<220> FEATURE:
<221> NAME/KEY: VARIANT
<222> LOCATION: (21)..(21)
<223> OTHER INFORMATION: Xaa is Ala or Glu
<220> FEATURE:
<221> NAME/KEY: VARIANT
<222> LOCATION: (23)..(23)
<223> OTHER INFORMATION: Xaa is Val or Ile
<220> FEATURE:
<221> NAME/KEY: VARIANT
<222> LOCATION: (24)..(24)
<223> OTHER INFORMATION: Xaa is Asn or Glu
<220> FEATURE:
<221> NAME/KEY: VARIANT
<222> LOCATION: (27)..(27)
<223> OTHER INFORMATION: Xaa is Leu, Glu, Ser, Lys or Val
<220> FEATURE:
<221> NAME/KEY: VARIANT
<222> LOCATION: (28)..(28)
<223> OTHER INFORMATION: Xaa is Aib, Ala, Ser or Arg
<220> FEATURE:
<221> NAME/KEY: VARIANT
<222> LOCATION: (29)..(29)
<223> OTHER INFORMATION: Xaa is Aib, Glu, Gly or Lys
<220> FEATURE:
<221> NAME/KEY: VARIANT
<222> LOCATION: (30)..(30)
<223> OTHER INFORMATION: Xaa is Lys, Gly or absent
<220> FEATURE:
<221> NAME/KEY: VARIANT
<222> LOCATION: (31)..(40)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 60

Tyr Xaa Glu Gly Thr Phe Xaa Ser Asp Xaa Xaa Ile Xaa Xaa Xaa Xaa
1               5                   10                  15

Xaa Ala Xaa Xaa Xaa Phe Xaa Xaa Trp Leu Xaa Xaa Xaa Xaa Xaa Xaa
                20                  25                  30

Xaa Xaa Xaa Xaa Xaa Xaa Xaa Xaa
        35                  40

<210> SEQ ID NO 61
<211> LENGTH: 42
<212> TYPE: PRT
<213> ORGANISM: Artificial sequence
<220> FEATURE:
<223> OTHER INFORMATION: Synthetic sequence: GIP Analogue: General
      Formula I' of PCT/EP2013/059319
<220> FEATURE:
<221> NAME/KEY: SITE
```

```
<222> LOCATION: (1)..(1)
<223> OTHER INFORMATION: Linked to R1, wherein R1 is Hy-, Ac or pGlu
<220> FEATURE:
<221> NAME/KEY: VARIANT
<222> LOCATION: (2)..(2)
<223> OTHER INFORMATION: Xaa is Ala, Aib or Gly
<220> FEATURE:
<221> NAME/KEY: VARIANT
<222> LOCATION: (3)..(3)
<223> OTHER INFORMATION: Xaa is Glu or Asp
<220> FEATURE:
<221> NAME/KEY: VARIANT
<222> LOCATION: (7)..(7)
<223> OTHER INFORMATION: Xaa is Thr, Ser or Ile
<220> FEATURE:
<221> NAME/KEY: VARIANT
<222> LOCATION: (9)..(9)
<223> OTHER INFORMATION: Xaa is Asp or Glu
<220> FEATURE:
<221> NAME/KEY: VARIANT
<222> LOCATION: (10)..(10)
<223> OTHER INFORMATION: Xaa is Tyr, Leu or Ser
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (12)..(12)
<223> OTHER INFORMATION: Xaa is Ile or Lys
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (14)..(14)
<223> OTHER INFORMATION: Xaa is Met, Leu or Ser
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Lys, Gly, Ser or Glu
<220> FEATURE:
<221> NAME/KEY: VARIANT
<222> LOCATION: (19)..(19)
<223> OTHER INFORMATION: Xaa is Gln, Ala, Glu or Lys
<220> FEATURE:
<221> NAME/KEY: VARIANT
<222> LOCATION: (20)..(20)
<223> OTHER INFORMATION: Xaa is Gln, Lys, Arg or His
<220> FEATURE:
<221> NAME/KEY: VARIANT
<222> LOCATION: (21)..(21)
<223> OTHER INFORMATION: Xaa is Asp, Ala or Glu
<220> FEATURE:
<221> NAME/KEY: VARIANT
<222> LOCATION: (22)..(22)
<223> OTHER INFORMATION: Xaa is Phe or 1Nal
<220> FEATURE:
<221> NAME/KEY: VARIANT
<222> LOCATION: (23)..(23)
<223> OTHER INFORMATION: Xaa is Val, Ile or Leu
<220> FEATURE:
<221> NAME/KEY: VARIANT
<222> LOCATION: (24)..(24)
<223> OTHER INFORMATION: Xaa is Asn, Glu, Arg or Lys
<220> FEATURE:
<221> NAME/KEY: VARIANT
<222> LOCATION: (27)..(27)
<223> OTHER INFORMATION: Xaa is Leu, Val, Ile, Lys, Glu or Ser
<220> FEATURE:
<221> NAME/KEY: VARIANT
<222> LOCATION: (28)..(28)
<223> OTHER INFORMATION: Xaa is Ala, Ser, Arg or Aib
<220> FEATURE:
```

```
<221> NAME/KEY: VARIANT
<222> LOCATION: (29)..(29)
<223> OTHER INFORMATION: Xaa is Gln, Aib, Lys, Gly or Ala
<220> FEATURE:
<221> NAME/KEY: VARIANT
<222> LOCATION: (30)..(30)
<223> OTHER INFORMATION: Xaa is Lys, Gly, Pro or absent
<220> FEATURE:
<221> NAME/KEY: VARIANT
<222> LOCATION: (31)..(31)
<223> OTHER INFORMATION: Xaa is Gly, Pro, Ser, Glu or absent
<220> FEATURE:
<221> NAME/KEY: VARIANT
<222> LOCATION: (32)..(32)
<223> OTHER INFORMATION: Xaa is Lys, Ser or absent
<220> FEATURE:
<221> NAME/KEY: VARIANT
<222> LOCATION: (33)..(33)
<223> OTHER INFORMATION: Xaa is Lys, Ser, Glu or absent
<220> FEATURE:
<221> NAME/KEY: VARIANT
<222> LOCATION: (34)..(34)
<223> OTHER INFORMATION: Xaa is Asn, Gly, Ala, Lys or absent
<220> FEATURE:
<221> NAME/KEY: VARIANT
<222> LOCATION: (35)..(35)
<223> OTHER INFORMATION: Xaa is Asp, Ala, Pro, Glu or absent
<220> FEATURE:
<221> NAME/KEY: VARIANT
<222> LOCATION: (36)..(36)
<223> OTHER INFORMATION: Xaa is Trp, Pro, Lys or absent
<220> FEATURE:
<221> NAME/KEY: VARIANT
<222> LOCATION: (37)..(37)
<223> OTHER INFORMATION: Xaa is Lys, Pro, Glu or absent
<220> FEATURE:
<221> NAME/KEY: VARIANT
<222> LOCATION: (38)..(38)
<223> OTHER INFORMATION: Xaa is His, Pro, Ser, Lys or absent
<220> FEATURE:
<221> NAME/KEY: VARIANT
<222> LOCATION: (39)..(39)
<223> OTHER INFORMATION: Xaa is Asn, Ser or absent
<220> FEATURE:
<221> NAME/KEY: VARIANT
<222> LOCATION: (40)..(40)
<223> OTHER INFORMATION: Xaa is Ile or absent
<220> FEATURE:
<221> NAME/KEY: VARIANT
<222> LOCATION: (41)..(41)
<223> OTHER INFORMATION: Xaa is Thr or absent
<220> FEATURE:
<221> NAME/KEY: VARIANT
<222> LOCATION: (42)..(42)
<223> OTHER INFORMATION: Xaa is Gln or absent

<400> SEQUENCE: 61

Tyr Xaa Xaa Gly Thr Phe Xaa Ser Xaa Xaa Xaa Xaa Xaa Xaa Xaa
1               5                   10                  15

Lys Ala Xaa Xaa Xaa Xaa Xaa Xaa Trp Leu Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 62
<211> LENGTH: 42
<212> TYPE: PRT
<213> ORGANISM: Artificial sequence
<220> FEATURE:
<223> OTHER INFORMATION: Synthetic sequence: GIP Analogue: General
      Formula I(a)' of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
```

```
<220> FEATURE:
<221> NAME/KEY: VARIANT
<222> LOCATION: (2)..(2)
<223> OTHER INFORMATION: Xaa is Ala, Aib or Gly
<220> FEATURE:
<221> NAME/KEY: VARIANT
<222> LOCATION: (3)..(3)
<223> OTHER INFORMATION: Xaa is Glu or Asp
<220> FEATURE:
<221> NAME/KEY: VARIANT
<222> LOCATION: (7)..(7)
<223> OTHER INFORMATION: Xaa is Thr, Ser or Ile
<220> FEATURE:
<221> NAME/KEY: VARIANT
<222> LOCATION: (9)..(9)
<223> OTHER INFORMATION: Xaa is Asp or Glu
<220> FEATURE:
<221> NAME/KEY: VARIANT
<222> LOCATION: (10)..(10)
<223> OTHER INFORMATION: Xaa is Tyr, Leu or Ser
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (12)..(12)
<223> OTHER INFORMATION: Xaa is Ile or Lys
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (14)..(14)
<223> OTHER INFORMATION: Xaa is Leu or Ser
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Lys, Gly, Ser or Glu
<220> FEATURE:
<221> NAME/KEY: VARIANT
<222> LOCATION: (19)..(19)
<223> OTHER INFORMATION: Xaa is Gln, Ala, Glu or Lys
<220> FEATURE:
<221> NAME/KEY: VARIANT
<222> LOCATION: (20)..(20)
<223> OTHER INFORMATION: Xaa is Gln, Lys, Arg or His
<220> FEATURE:
<221> NAME/KEY: VARIANT
<222> LOCATION: (21)..(21)
<223> OTHER INFORMATION: Xaa is Asp, Ala or Glu
<220> FEATURE:
<221> NAME/KEY: VARIANT
<222> LOCATION: (22)..(22)
<223> OTHER INFORMATION: Xaa is Phe or 1Nal
<220> FEATURE:
<221> NAME/KEY: VARIANT
<222> LOCATION: (23)..(23)
<223> OTHER INFORMATION: Xaa is Val, Ile or Leu
<220> FEATURE:
<221> NAME/KEY: VARIANT
<222> LOCATION: (24)..(24)
<223> OTHER INFORMATION: Xaa is Asn, Glu, Arg or Lys
<220> FEATURE:
<221> NAME/KEY: VARIANT
<222> LOCATION: (27)..(27)
<223> OTHER INFORMATION: Xaa is Leu, Val, Ile, Lys, Glu or Ser
<220> FEATURE:
<221> NAME/KEY: VARIANT
<222> LOCATION: (28)..(28)
<223> OTHER INFORMATION: Xaa is Ala, Ser, Arg or Aib
<220> FEATURE:
<221> NAME/KEY: VARIANT
<222> LOCATION: (29)..(29)
```

-continued

```
<223> OTHER INFORMATION: Xaa is Gln, Aib, Lys, Gly or Ala
<220> FEATURE:
<221> NAME/KEY: VARIANT
<222> LOCATION: (30)..(30)
<223> OTHER INFORMATION: Xaa is Lys, Gly, Pro or absent
<220> FEATURE:
<221> NAME/KEY: VARIANT
<222> LOCATION: (31)..(31)
<223> OTHER INFORMATION: Xaa is Gly, Pro, Ser, Glu or absent
<220> FEATURE:
<221> NAME/KEY: VARIANT
<222> LOCATION: (32)..(32)
<223> OTHER INFORMATION: Xaa is Lys, Ser or absent
<220> FEATURE:
<221> NAME/KEY: VARIANT
<222> LOCATION: (33)..(33)
<223> OTHER INFORMATION: Xaa is Lys, Ser, Glu or absent
<220> FEATURE:
<221> NAME/KEY: VARIANT
<222> LOCATION: (34)..(34)
<223> OTHER INFORMATION: Xaa is Asn, Gly, Ala, Lys or absent
<220> FEATURE:
<221> NAME/KEY: VARIANT
<222> LOCATION: (35)..(35)
<223> OTHER INFORMATION: Xaa is Asp, Ala, Pro, Glu or absent
<220> FEATURE:
<221> NAME/KEY: VARIANT
<222> LOCATION: (36)..(36)
<223> OTHER INFORMATION: Xaa is Trp, Pro, Lys or absent
<220> FEATURE:
<221> NAME/KEY: VARIANT
<222> LOCATION: (37)..(37)
<223> OTHER INFORMATION: Xaa is Lys, Pro, Glu or absent
<220> FEATURE:
<221> NAME/KEY: VARIANT
<222> LOCATION: (38)..(38)
<223> OTHER INFORMATION: Xaa is His, Pro, Ser, Lys or absent
<220> FEATURE:
<221> NAME/KEY: VARIANT
<222> LOCATION: (39)..(39)
<223> OTHER INFORMATION: Xaa is Asn, Ser or absent
<220> FEATURE:
<221> NAME/KEY: VARIANT
<222> LOCATION: (40)..(40)
<223> OTHER INFORMATION: Xaa is Ile or absent
<220> FEATURE:
<221> NAME/KEY: VARIANT
<222> LOCATION: (41)..(41)
<223> OTHER INFORMATION: Xaa is Thr or absent
<220> FEATURE:
<221> NAME/KEY: VARIANT
<222> LOCATION: (42)..(42)
<223> OTHER INFORMATION: Xaa is Gln or absent

<400> SEQUENCE: 62

Tyr Xaa Xaa Gly Thr Phe Xaa Ser Xaa Xaa Xaa Xaa Xaa Xaa Xaa
1               5                   10                  15

Lys Ala Xaa Xaa Xaa Xaa Xaa Xaa Trp Leu Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 63
<211> LENGTH: 42
<212> TYPE: PRT
<213> ORGANISM: Artificial sequence
<220> FEATURE:
<223> OTHER INFORMATION: Synthetic sequence: GIP Analogue: General
      Formula I(b)' of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: VARIANT
```

```
<222> LOCATION: (2)..(2)
<223> OTHER INFORMATION: Xaa is Ala, Aib or Gly
<220> FEATURE:
<221> NAME/KEY: VARIANT
<222> LOCATION: (3)..(3)
<223> OTHER INFORMATION: Xaa is Glu or Asp
<220> FEATURE:
<221> NAME/KEY: VARIANT
<222> LOCATION: (7)..(7)
<223> OTHER INFORMATION: Xaa is Thr or Ser
<220> FEATURE:
<221> NAME/KEY: VARIANT
<222> LOCATION: (9)..(9)
<223> OTHER INFORMATION: Xaa is Asp or Glu
<220> FEATURE:
<221> NAME/KEY: VARIANT
<222> LOCATION: (10)..(10)
<223> OTHER INFORMATION: Xaa is Tyr or Leu
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (12)..(12)
<223> OTHER INFORMATION: Xaa is Ile or Lys
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (14)..(14)
<223> OTHER INFORMATION: Xaa is Leu or Ser
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Lys, Ser or Glu
<220> FEATURE:
<221> NAME/KEY: VARIANT
<222> LOCATION: (19)..(19)
<223> OTHER INFORMATION: Xaa is Gln, Ala, Glu or Lys
<220> FEATURE:
<221> NAME/KEY: VARIANT
<222> LOCATION: (20)..(20)
<223> OTHER INFORMATION: Xaa is Gln, Lys, Arg or His
<220> FEATURE:
<221> NAME/KEY: VARIANT
<222> LOCATION: (21)..(21)
<223> OTHER INFORMATION: Xaa is Asp, Ala or Glu
<220> FEATURE:
<221> NAME/KEY: VARIANT
<222> LOCATION: (23)..(23)
<223> OTHER INFORMATION: Xaa is Val, Ile or Leu
<220> FEATURE:
<221> NAME/KEY: VARIANT
<222> LOCATION: (24)..(24)
<223> OTHER INFORMATION: Xaa is Asn, Glu, Arg or Lys
<220> FEATURE:
<221> NAME/KEY: VARIANT
<222> LOCATION: (27)..(27)
<223> OTHER INFORMATION: Xaa is Leu, Glu, Val or Ile
<220> FEATURE:
<221> NAME/KEY: VARIANT
<222> LOCATION: (28)..(28)
<223> OTHER INFORMATION: Xaa is Ala, Ser, Arg or Aib
<220> FEATURE:
<221> NAME/KEY: VARIANT
<222> LOCATION: (29)..(29)
<223> OTHER INFORMATION: Xaa is Gln, Gly, Aib or Ala
<220> FEATURE:
<221> NAME/KEY: VARIANT
<222> LOCATION: (30)..(30)
<223> OTHER INFORMATION: Xaa is Lys, Gly, Pro or absent
<220> FEATURE:
```

```
<221> NAME/KEY: VARIANT
<222> LOCATION: (31)..(31)
<223> OTHER INFORMATION: Xaa is Gly, Pro, Ser, Glu or absent
<220> FEATURE:
<221> NAME/KEY: VARIANT
<222> LOCATION: (32)..(32)
<223> OTHER INFORMATION: Xaa is Lys, Ser or absent
<220> FEATURE:
<221> NAME/KEY: VARIANT
<222> LOCATION: (33)..(33)
<223> OTHER INFORMATION: Xaa is Lys, Ser, Glu or absent
<220> FEATURE:
<221> NAME/KEY: VARIANT
<222> LOCATION: (34)..(34)
<223> OTHER INFORMATION: Xaa is Asn, Gly, Ala, Lys or absent
<220> FEATURE:
<221> NAME/KEY: VARIANT
<222> LOCATION: (35)..(35)
<223> OTHER INFORMATION: Xaa is Asp, Ala, Pro, Glu or absent
<220> FEATURE:
<221> NAME/KEY: VARIANT
<222> LOCATION: (36)..(36)
<223> OTHER INFORMATION: Xaa is Trp, Pro, Lys or absent
<220> FEATURE:
<221> NAME/KEY: VARIANT
<222> LOCATION: (37)..(37)
<223> OTHER INFORMATION: Xaa is Lys, Pro, Glu or absent
<220> FEATURE:
<221> NAME/KEY: VARIANT
<222> LOCATION: (38)..(38)
<223> OTHER INFORMATION: Xaa is His, Pro, Ser, Lys or absent
<220> FEATURE:
<221> NAME/KEY: VARIANT
<222> LOCATION: (39)..(39)
<223> OTHER INFORMATION: Xaa is Asn, Ser or absent
<220> FEATURE:
<221> NAME/KEY: VARIANT
<222> LOCATION: (40)..(40)
<223> OTHER INFORMATION: Xaa is Ile or absent
<220> FEATURE:
<221> NAME/KEY: VARIANT
<222> LOCATION: (41)..(41)
<223> OTHER INFORMATION: Xaa is Thr or absent
<220> FEATURE:
<221> NAME/KEY: VARIANT
<222> LOCATION: (42)..(42)
<223> OTHER INFORMATION: Xaa is Gln or absent

<400> SEQUENCE: 63

Tyr Xaa Xaa Gly Thr Phe Xaa Ser Xaa Xaa Xaa Xaa Xaa Xaa Xaa Xaa
1               5                   10                  15

Lys Ala Xaa Xaa Xaa Phe Xaa Xaa Trp Leu Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 64
<211> LENGTH: 40
<212> TYPE: PRT
<213> ORGANISM: Artificial sequence
<220> FEATURE:
<223> OTHER INFORMATION: Synthetic sequence: GIP Analogue: General
      Formula II' of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: VARIANT
<222> LOCATION: (2)..(2)
<223> OTHER INFORMATION: Xaa is Aib or Gly
<220> FEATURE:
<221> NAME/KEY: VARIANT
<222> LOCATION: (7)..(7)
<223> OTHER INFORMATION: Xaa is Thr, Ile or Ser
```

```
<220> FEATURE:
<221> NAME/KEY: VARIANT
<222> LOCATION: (10)..(10)
<223> OTHER INFORMATION: Xaa is Tyr or Leu
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (12)..(12)
<223> OTHER INFORMATION: Xaa is Ile or Lys
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Ser, Glu or Lys
<220> FEATURE:
<221> NAME/KEY: VARIANT
<222> LOCATION: (19)..(19)
<223> OTHER INFORMATION: Xaa is Gln or Ala
<220> FEATURE:
<221> NAME/KEY: VARIANT
<222> LOCATION: (20)..(20)
<223> OTHER INFORMATION: Xaa is Lys, His or Arg
<220> FEATURE:
<221> NAME/KEY: VARIANT
<222> LOCATION: (21)..(21)
<223> OTHER INFORMATION: Xaa is Ala, Asp or Glu
<220> FEATURE:
<221> NAME/KEY: VARIANT
<222> LOCATION: (23)..(23)
<223> OTHER INFORMATION: Xaa is Val or Ile
<220> FEATURE:
<221> NAME/KEY: VARIANT
<222> LOCATION: (24)..(24)
<223> OTHER INFORMATION: Xaa is Asn, Lys or Glu
<220> FEATURE:
<221> NAME/KEY: VARIANT
<222> LOCATION: (27)..(27)
<223> OTHER INFORMATION: Xaa is Leu, Glu, Val or Ile
<220> FEATURE:
<221> NAME/KEY: VARIANT
<222> LOCATION: (28)..(28)
<223> OTHER INFORMATION: Xaa is Aib, Ala, Ser or Arg
<220> FEATURE:
<221> NAME/KEY: VARIANT
<222> LOCATION: (29)..(29)
<223> OTHER INFORMATION: Xaa is Gln, Aib, Ala, Gly or Lys
<220> FEATURE:
<221> NAME/KEY: VARIANT
<222> LOCATION: (30)..(30)
<223> OTHER INFORMATION: Xaa is Lys, Gly or absent
<220> FEATURE:
<221> NAME/KEY: VARIANT
<222> LOCATION: (31)..(40)
<223> OTHER INFORMATION: Y1, which may be present or absent. If
      present, up to 2 residues may be present or absent, and Y1 is
      SEQ ID NO: 74, SEQ ID NO: 75, SEQ ID NO: 76, or SEQ ID NO: 77.

<400> SEQUENCE: 64

Tyr Xaa Glu Gly Thr Phe Xaa Ser Asp Xaa Xaa Xaa Xaa Leu Xaa Xaa
 1               5                  10                  15

Lys Ala Xaa Xaa Xaa Phe Xaa Xaa Trp Leu Xaa Xaa Xaa Xaa Xaa Xaa
             20                  25                  30

Xaa Xaa Xaa Xaa Xaa Xaa Xaa Xaa
         35                  40
```

```
<210> SEQ ID NO 65
<211> LENGTH: 40
<212> TYPE: PRT
<213> ORGANISM: Artificial sequence
<220> FEATURE:
<223> OTHER INFORMATION: Synthetic sequence: GIP Analogue: General
      Formula II(a)' of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: VARIANT
<222> LOCATION: (2)..(2)
<223> OTHER INFORMATION: Xaa is Aib or Gly
<220> FEATURE:
<221> NAME/KEY: VARIANT
<222> LOCATION: (7)..(7)
<223> OTHER INFORMATION: Xaa is Thr, Ile or Ser
<220> FEATURE:
<221> NAME/KEY: VARIANT
<222> LOCATION: (10)..(10)
<223> OTHER INFORMATION: Xaa is Tyr or Leu
<220> FEATURE:
<221> NAME/KEY: VARIANT
<222> LOCATION: (11)..(11)
<223> OTHER INFORMATION: Xaa is Ser or Leu
<220> FEATURE:
<221> NAME/KEY: VARIANT
<222> LOCATION: (13)..(13)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Ser, Glu or Lys
<220> FEATURE:
<221> NAME/KEY: VARIANT
<222> LOCATION: (19)..(19)
<223> OTHER INFORMATION: Xaa is Gln, Lys, Ala or Glu
<220> FEATURE:
<221> NAME/KEY: VARIANT
<222> LOCATION: (20)..(20)
<223> OTHER INFORMATION: Xaa is Lys, His or Arg
<220> FEATURE:
<221> NAME/KEY: VARIANT
<222> LOCATION: (21)..(21)
<223> OTHER INFORMATION: Xaa is Ala, Asp or Glu
<220> FEATURE:
<221> NAME/KEY: VARIANT
<222> LOCATION: (23)..(23)
<223> OTHER INFORMATION: Xaa is Val or Ile
<220> FEATURE:
<221> NAME/KEY: VARIANT
<222> LOCATION: (24)..(24)
<223> OTHER INFORMATION: Xaa is Asn, Lys or Glu
<220> FEATURE:
<221> NAME/KEY: VARIANT
<222> LOCATION: (27)..(27)
<223> OTHER INFORMATION: Xaa is Leu, Glu, Val or Ile
<220> FEATURE:
<221> NAME/KEY: VARIANT
<222> LOCATION: (28)..(28)
<223> OTHER INFORMATION: Xaa is Aib, Ala, Ser or Arg
<220> FEATURE:
<221> NAME/KEY: VARIANT
<222> LOCATION: (29)..(29)
<223> OTHER INFORMATION: Xaa is Gln, Aib, Ala, or Gly
<220> FEATURE:
<221> NAME/KEY: VARIANT
<222> LOCATION: (30)..(30)
<223> OTHER INFORMATION: Xaa is Lys, Gly or absent
<220> FEATURE:
<221> NAME/KEY: VARIANT
<222> LOCATION: (31)..(40)
<223> OTHER INFORMATION: Y1, which may be present or absent. If present,
``` up to 2 residues may be present or absent, and Y1 is SEQ ID NO: 74, SEQ ID NO: 75, SEQ ID NO: 76, or SEQ ID NO: 77.

<400> SEQUENCE: 65

Tyr Xaa Glu Gly Thr Phe Xaa Ser Asp Xaa Xaa Ile Xaa Leu Xaa Xaa
1               5                   10                  15

Lys Ala Xaa Xaa Xaa Phe Xaa Xaa Trp Leu Xaa Xaa Xaa Xaa Xaa
            20                  25                  30

Xaa Xaa Xaa Xaa Xaa Xaa Xaa Xaa
        35                  40

<210> SEQ ID NO 66
<211> LENGTH: 40
<212> TYPE: PRT
<213> ORGANISM: Artificial sequence
<220> FEATURE:
<223> OTHER INFORMATION: Synthetic sequence: GIP Analogue: General
      Formula II(b)' of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (7)..(7)
<223> OTHER INFORMATION: Xaa is Thr or Ser
<220> FEATURE:
<221> NAME/KEY: VARIANT
<222> LOCATION: (13)..(13)
<223> OTHER INFORMATION: Xaa is Ala or Tyr
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Lys, Glu or Ser
<220> FEATURE:
<221> NAME/KEY: VARIANT
<222> LOCATION: (20)..(20)
<223> OTHER INFORMATION: Xaa is Lys, His or Arg
<220> FEATURE:
<221> NAME/KEY: VARIANT
<222> LOCATION: (21)..(21)
<223> OTHER INFORMATION: Xaa is Ala, Asp or Glu
<220> FEATURE:
<221> NAME/KEY: VARIANT
<222> LOCATION: (23)..(23)
<223> OTHER INFORMATION: Xaa is Val or Ile
<220> FEATURE:
<221> NAME/KEY: VARIANT
<222> LOCATION: (27)..(27)
<223> OTHER INFORMATION: Xaa is Leu, Glu or Val
<220> FEATURE:
<221> NAME/KEY: VARIANT
<222> LOCATION: (28)..(28)
<223> OTHER INFORMATION: Xaa is Arg or Ser
<220> FEATURE:
<221> NAME/KEY: VARIANT
<222> LOCATION: (30)..(30)
<223> OTHER INFORMATION: Xaa is Lys, Gly or absent
<220> FEATURE:
<221> NAME/KEY: VARIANT
<222> LOCATION: (31)..(40)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 66

Tyr Ala Glu Gly Thr Phe Xaa Ser Asp Tyr Ser Ile Xaa Leu Xaa Xaa
1               5                   10                  15

Lys Ala Gln Xaa Xaa Phe Xaa Glu Trp Leu Xaa Xaa Ala Xaa Xaa Xaa
                20                  25                  30

Xaa Xaa Xaa Xaa Xaa Xaa Xaa Xaa
            35                  40

<210> SEQ ID NO 67
<211> LENGTH: 40
<212> TYPE: PRT
<213> ORGANISM: Artificial sequence
<220> FEATURE:
<223> OTHER INFORMATION: Synthetic sequence: GIP Analogue: General
      Formula II(c) of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (7)..(7)
<223> OTHER INFORMATION: Xaa is Thr or Ser
<220> FEATURE:
<221> NAME/KEY: VARIANT
<222> LOCATION: (13)..(13)
<223> OTHER INFORMATION: Xaa is Ala, Aib or Tyr
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Glu, Lys or Ser
<220> FEATURE:
<221> NAME/KEY: VARIANT
<222> LOCATION: (20)..(20)
<223> OTHER INFORMATION: Xaa is Lys, His or Arg
<220> FEATURE:
<221> NAME/KEY: VARIANT
<222> LOCATION: (21)..(21)
<223> OTHER INFORMATION: Xaa is Ala, Asp or Glu
<220> FEATURE:
<221> NAME/KEY: VARIANT
<222> LOCATION: (24)..(24)
<223> OTHER INFORMATION: Xaa is Glu or Asn
<220> FEATURE:
<221> NAME/KEY: VARIANT
<222> LOCATION: (27)..(27)
<223> OTHER INFORMATION: Xaa is Leu, Glu or Val
<220> FEATURE:
<221> NAME/KEY: VARIANT
<222> LOCATION: (29)..(29)
<223> OTHER INFORMATION: Xaa is Gln or Aib
<220> FEATURE:
<221> NAME/KEY: VARIANT
<222> LOCATION: (30)..(30)
<223> OTHER INFORMATION: Xaa is Lys, Gly or absent
<220> FEATURE:
<221> NAME/KEY: VARIANT
<222> LOCATION: (31)..(40)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 67

Tyr Ala Glu Gly Thr Phe Xaa Ser Asp Tyr Ser Ile Xaa Leu Xaa Xaa
1               5                   10                  15

Lys Ala Gln Xaa Xaa Phe Val Xaa Trp Leu Xaa Ala Xaa Xaa Xaa Xaa
                20                  25                  30

```
Xaa Xaa Xaa Xaa Xaa Xaa Xaa Xaa
        35                  40

<210> SEQ ID NO 68
<211> LENGTH: 40
<212> TYPE: PRT
<213> ORGANISM: Artificial sequence
<220> FEATURE:
<223> OTHER INFORMATION: Synthetic sequence: GIP Analogue: General
      Formula II(d) of PCT/EP2013/059319
<220> FEATURE:
<221> NAME/KEY: SITE
<222> LOCATION: (1)..(1)
<223> OTHER INFORMATION: Linked to R1, wherein R1 is Hy-, Ac or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (7)..(7)
<223> OTHER INFORMATION: Xaa is Thr or Ser
<220> FEATURE:
<221> NAME/KEY: VARIANT
<222> LOCATION: (13)..(13)
<223> OTHER INFORMATION: Xaa is Ala, Aib or Tyr
<220> FEATURE:
<221> NAME/KEY: VARIANT
<222> LOCATION: (15)..(15)
<223> OTHER INFORMATION: Xaa is Asp or Glu
<220> FEATURE:
<221> NAME/KEY: VARIANT
<222> LOCATION: (16)..(16)
<223> OTHER INFORMATION: Xaa is Glu, Lys or Ser
<220> FEATURE:
<221> NAME/KEY: VARIANT
<222> LOCATION: (20)..(20)
<223> OTHER INFORMATION: Xaa is Lys, His or Arg
<220> FEATURE:
<221> NAME/KEY: VARIANT
<222> LOCATION: (27)..(27)
<223> OTHER INFORMATION: Xaa is Leu, Glu or Val
<220> FEATURE:
<221> NAME/KEY: VARIANT
<222> LOCATION: (30)..(30)
<223> OTHER INFORMATION: Xaa is Lys, Gly or absent
<220> FEATURE:
<221> NAME/KEY: VARIANT
<222> LOCATION: (31)..(40)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 68

Tyr Ala Glu Gly Thr Phe Xaa Ser Asp Tyr Ser Ile Xaa Leu Xaa Xaa
1               5                   10                  15

Lys Ala Gln Xaa Ala Phe Val Glu Trp Leu Xaa Ala Gln Xaa Xaa Xaa
            20                  25                  30

Xaa Xaa Xaa Xaa Xaa Xaa Xaa Xaa
        35                  40

<210> SEQ ID NO 69
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: MOD_RES
<222> LOCATION: (2)..(2)
<223> OTHER INFORMATION: Aib
<220> FEATURE:
<221> NAME/KEY: SITE
```

```
<222> LOCATION: (17)..(17)
<223> OTHER INFORMATION: Lys(Hexadecanoyl-isoGlu)

<400> SEQUENCE: 69

Tyr Ala Glu Gly Thr Phe Thr Ser Asp Tyr Ser Ile Tyr Leu Asp Glu
1               5                   10                  15

Lys Ala Ala His Asp Phe Val Glu Trp Leu Leu Ser Ala
            20                  25

<210> SEQ ID NO 70
<211> LENGTH: 29
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (2)..(2)
<223> OTHER INFORMATION: Aib

<400> SEQUENCE: 70

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 71
<211> LENGTH: 29
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (2)..(2)
<223> OTHER INFORMATION: Aib

<400> SEQUENCE: 71

Tyr Ala Glu Gly Thr Phe Thr Ser Asp Tyr Ser Ile Tyr Leu Glu Lys
1               5                   10                  15

Lys Ala Ala Lys Glu Phe Val Glu Trp Leu Leu Ser Ala
            20                  25

<210> SEQ ID NO 72
<211> LENGTH: 29
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (2)..(2)
<223> OTHER INFORMATION: Aib

<400> SEQUENCE: 72

Tyr Ala Glu Gly Thr Phe Thr Ser Asp Tyr Ser Ile Tyr Leu Asp Glu
1               5                   10                  15

Lys Ala Ala Lys Glu Phe Ile Glu Trp Leu Glu Ser Ala
            20                  25

<210> SEQ ID NO 73
<211> LENGTH: 29
<212> TYPE: PRT
<213> ORGANISM: Artificial sequence
<220> FEATURE:
<223> OTHER INFORMATION: Synthetic sequence: GIP Analogue
<220> FEATURE:
```

```
<221> NAME/KEY: MOD_RES
<222> LOCATION: (2)..(2)
<223> OTHER INFORMATION: Aib

<400> SEQUENCE: 73

Tyr Ala Glu Gly Thr Phe Thr Ser Asp Tyr Ser Ile Tyr Leu Glu Lys
1               5                   10                  15

Lys Ala Ala His Asp Phe Val Glu Trp Leu Leu Ser Ala
            20                  25

<210> SEQ ID NO 74
<211> LENGTH: 10
<212> TYPE: PRT
<213> ORGANISM: Artificial sequence
<220> FEATURE:
<223> OTHER INFORMATION: Synthetic sequence: Y1 in SEQ ID NOs: 2, 34,
      60, 64 - 68, 79, 81, 83, and 87 - 91

<400> SEQUENCE: 74

Gly Pro Ser Ser Gly Ala Pro Pro Pro Ser
1               5                   10

<210> SEQ ID NO 75
<211> LENGTH: 9
<212> TYPE: PRT
<213> ORGANISM: Artificial sequence
<220> FEATURE:
<223> OTHER INFORMATION: Synthetic sequence: Y1 in SEQ ID NOs: 2, 34,
      60, 64 - 68, 79, 81, 83, and 87 - 91

<400> SEQUENCE: 75

Gly Pro Ser Ser Gly Ala Pro Pro Ser
1               5

<210> SEQ ID NO 76
<211> LENGTH: 9
<212> TYPE: PRT
<213> ORGANISM: Artificial sequence
<220> FEATURE:
<223> OTHER INFORMATION: Synthetic sequence: Y1 in SEQ ID NOs: 2, 34,
      60, 64 - 68, 79, 81, 83, and 87 - 91

<400> SEQUENCE: 76

Pro Ser Ser Gly Ala Pro Pro Pro Ser
1               5

<210> SEQ ID NO 77
<211> LENGTH: 8
<212> TYPE: PRT
<213> ORGANISM: Artificial sequence
<220> FEATURE:
<223> OTHER INFORMATION: Synthetic sequence: Y1 in SEQ ID NOs: 2, 34,
      60, 64 - 68, 79, 81, 83, and 87 - 91

<400> SEQUENCE: 77

Pro Ser Ser Gly Ala Pro Pro Ser
1               5

<210> SEQ ID NO 78
<211> LENGTH: 43
<212> TYPE: PRT
<213> ORGANISM: Artificial sequence
<220> FEATURE:
<223> OTHER INFORMATION: Synthetic sequence: GIP Analogue: General
      Formula I(b) of PCT/EP2013/059319
<220> FEATURE:
<221> NAME/KEY: VARIANT
<222> LOCATION: (1)..(1)
```

```
<223> OTHER INFORMATION: Xaa is Hy-, Ac or pGlu
<220> FEATURE:
<221> NAME/KEY: VARIANT
<222> LOCATION: (2)..(2)
<223> OTHER INFORMATION: Xaa is His or Tyr
<220> FEATURE:
<221> NAME/KEY: VARIANT
<222> LOCATION: (3)..(3)
<223> OTHER INFORMATION: Xaa is Ala, Aib or Gly
<220> FEATURE:
<221> NAME/KEY: VARIANT
<222> LOCATION: (4)..(4)
<223> OTHER INFORMATION: Xaa is Glu or Asp
<220> FEATURE:
<221> NAME/KEY: VARIANT
<222> LOCATION: (8)..(8)
<223> OTHER INFORMATION: Xaa is Thr or Ser
<220> FEATURE:
<221> NAME/KEY: VARIANT
<222> LOCATION: (10)..(10)
<223> OTHER INFORMATION: Xaa is Asp or Glu
<220> FEATURE:
<221> NAME/KEY: VARIANT
<222> LOCATION: (11)..(11)
<223> OTHER INFORMATION: Xaa is Tyr, Leu or Ser
<220> FEATURE:
<221> NAME/KEY: VARIANT
<222> LOCATION: (12)..(12)
<223> OTHER INFORMATION: Xaa is Ser or Leu
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Met, Leu or Ser
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Lys, Gly, Ser or Glu
<220> FEATURE:
<221> NAME/KEY: VARIANT
<222> LOCATION: (18)..(18)
<223> OTHER INFORMATION: Xaa is Ile, Lys, Gln, Arg or Glu
<220> FEATURE:
<221> NAME/KEY: VARIANT
<222> LOCATION: (20)..(20)
<223> OTHER INFORMATION: Xaa is Gln, Ala, Glu or Lys
<220> FEATURE:
<221> NAME/KEY: VARIANT
<222> LOCATION: (21)..(21)
<223> OTHER INFORMATION: Xaa is Gln, Lys or Arg
<220> FEATURE:
<221> NAME/KEY: VARIANT
<222> LOCATION: (22)..(22)
<223> OTHER INFORMATION: Xaa is Asp, Ala or Glu
<220> FEATURE:
<221> NAME/KEY: VARIANT
<222> LOCATION: (23)..(23)
<223> OTHER INFORMATION: Xaa is Phe or 1Nal
<220> FEATURE:
<221> NAME/KEY: VARIANT
<222> LOCATION: (24)..(24)
<223> OTHER INFORMATION: Xaa is Val, Ile or Leu
<220> FEATURE:
<221> NAME/KEY: VARIANT
<222> LOCATION: (25)..(25)
<223> OTHER INFORMATION: Xaa is Asn, Glu, Arg or Lys
<220> FEATURE:
<221> NAME/KEY: VARIANT
<222> LOCATION: (28)..(28)
<223> OTHER INFORMATION: Xaa is Leu, Val, Ile, Lys or Ser
<220> FEATURE:
<221> NAME/KEY: VARIANT
```

```
<222> LOCATION: (29)..(29)
<223> OTHER INFORMATION: Xaa is Ala or Aib
<220> FEATURE:
<221> NAME/KEY: VARIANT
<222> LOCATION: (30)..(30)
<223> OTHER INFORMATION: Xaa is Gln, Gly, Aib or Tyr
<220> FEATURE:
<221> NAME/KEY: VARIANT
<222> LOCATION: (31)..(31)
<223> OTHER INFORMATION: Xaa is Lys, Gly, Pro or absent
<220> FEATURE:
<221> NAME/KEY: VARIANT
<222> LOCATION: (32)..(32)
<223> OTHER INFORMATION: Xaa is Gly, Pro, Ser, Glu or absent
<220> FEATURE:
<221> NAME/KEY: VARIANT
<222> LOCATION: (33)..(33)
<223> OTHER INFORMATION: Xaa is Lys, Ser or absent
<220> FEATURE:
<221> NAME/KEY: VARIANT
<222> LOCATION: (34)..(34)
<223> OTHER INFORMATION: Xaa is Lys, Ser, Glu or absent
<220> FEATURE:
<221> NAME/KEY: VARIANT
<222> LOCATION: (35)..(35)
<223> OTHER INFORMATION: Xaa is Asn, Gly, Ala, Lys or absent
<220> FEATURE:
<221> NAME/KEY: VARIANT
<222> LOCATION: (36)..(36)
<223> OTHER INFORMATION: Xaa is Asp, Ala, Pro, Glu or absent
<220> FEATURE:
<221> NAME/KEY: VARIANT
<222> LOCATION: (37)..(37)
<223> OTHER INFORMATION: Xaa is Trp, Pro, Lys or absent
<220> FEATURE:
<221> NAME/KEY: VARIANT
<222> LOCATION: (38)..(38)
<223> OTHER INFORMATION: Xaa is Lys, Pro, Glu or absent
<220> FEATURE:
<221> NAME/KEY: VARIANT
<222> LOCATION: (39)..(39)
<223> OTHER INFORMATION: Xaa is His, Pro, Ser, Lys or absent
<220> FEATURE:
<221> NAME/KEY: VARIANT
<222> LOCATION: (40)..(40)
<223> OTHER INFORMATION: Xaa is Asn, Ser or absent
<220> FEATURE:
<221> NAME/KEY: VARIANT
<222> LOCATION: (41)..(41)
<223> OTHER INFORMATION: Xaa is Ile or absent
<220> FEATURE:
<221> NAME/KEY: VARIANT
<222> LOCATION: (42)..(42)
<223> OTHER INFORMATION: Xaa is Thr or absent
<220> FEATURE:
<221> NAME/KEY: VARIANT
<222> LOCATION: (43)..(43)
<223> OTHER INFORMATION: Xaa is Gln or absent

<400> SEQUENCE: 78

Xaa Xaa Xaa Xaa Gly Thr Phe Xaa Ser Xaa Xaa Xaa Ile Xaa Xaa Xaa
1               5                   10                  15

Xaa Xaa Ala Xaa Xaa Xaa Xaa Xaa Xaa Trp Leu Xaa Xaa Xaa Xaa Xaa
            20                  25                  30

Xaa Xaa Xaa Xaa Xaa Xaa Xaa Xaa Xaa Xaa Xaa
            35                  40

<210> SEQ ID NO 79
<211> LENGTH: 41
<212> TYPE: PRT
<213> ORGANISM: Artificial sequence
<220> FEATURE:
<223> OTHER INFORMATION: Synthetic sequence: GIP Analogue: General
      Formula II(b) of PCT/EP2013/059319
<220> FEATURE:
```

```
<221> NAME/KEY: VARIANT
<222> LOCATION: (1)..(1)
<223> OTHER INFORMATION: Xaa is Hy-, Ac or pGlu
<220> FEATURE:
<221> NAME/KEY: MOD_RES
<222> LOCATION: (3)..(3)
<223> OTHER INFORMATION: Aib
<220> FEATURE:
<221> NAME/KEY: VARIANT
<222> LOCATION: (8)..(8)
<223> OTHER INFORMATION: Xaa is Thr or Ser
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Leu
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (18)..(18)
<223> OTHER INFORMATION: Xaa is Ile or Lys
<220> FEATURE:
<221> NAME/KEY: VARIANT
<222> LOCATION: (21)..(21)
<223> OTHER INFORMATION: Xaa is Lys or Arg
<220> FEATURE:
<221> NAME/KEY: VARIANT
<222> LOCATION: (22)..(22)
<223> OTHER INFORMATION: Xaa is Ala or Glu
<220> FEATURE:
<221> NAME/KEY: VARIANT
<222> LOCATION: (24)..(24)
<223> OTHER INFORMATION: Xaa is Val or Ile
<220> FEATURE:
<221> NAME/KEY: VARIANT
<222> LOCATION: (25)..(25)
<223> OTHER INFORMATION: Xaa is Asn or Glu
<220> FEATURE:
<221> NAME/KEY: VARIANT
<222> LOCATION: (28)..(28)
<223> OTHER INFORMATION: Xaa is Leu or Val
<220> FEATURE:
<221> NAME/KEY: VARIANT
<222> LOCATION: (30)..(30)
<223> OTHER INFORMATION: Xaa is Aib or Gly
<220> FEATURE:
<221> NAME/KEY: VARIANT
<222> LOCATION: (31)..(31)
<223> OTHER INFORMATION: Xaa is Lys, Gly or absent
<220> FEATURE:
<221> NAME/KEY: VARIANT
<222> LOCATION: (32)..(41)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 79

Xaa Tyr Ala Glu Gly Thr Phe Xaa Ser Asp Tyr Ser Ile Xaa Xaa Xaa
1               5                   10                  15

Lys Xaa Ala Gln Xaa Xaa Phe Xaa Xaa Trp Leu Xaa Ala Xaa Xaa Xaa
            20                  25                  30

Xaa Xaa Xaa Xaa Xaa Xaa Xaa Xaa Xaa
        35                  40

<210> SEQ ID NO 80
<211> LENGTH: 43
<212> TYPE: PRT
<213> ORGANISM: Artificial sequence
<220> FEATURE:
```

```
<223> OTHER INFORMATION: Synthetic sequence: GIP Analogue: General
      Formula I(a) of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: VARIANT
<222> LOCATION: (2)..(2)
<223> OTHER INFORMATION: Xaa is His or Tyr
<220> FEATURE:
<221> NAME/KEY: VARIANT
<222> LOCATION: (3)..(3)
<223> OTHER INFORMATION: Xaa is Ala, Aib or Gly
<220> FEATURE:
<221> NAME/KEY: VARIANT
<222> LOCATION: (4)..(4)
<223> OTHER INFORMATION: Xaa is Glu or Asp
<220> FEATURE:
<221> NAME/KEY: VARIANT
<222> LOCATION: (8)..(8)
<223> OTHER INFORMATION: Xaa is Thr, Ser or Ile
<220> FEATURE:
<221> NAME/KEY: VARIANT
<222> LOCATION: (10)..(10)
<223> OTHER INFORMATION: Xaa is Asp or Glu
<220> FEATURE:
<221> NAME/KEY: VARIANT
<222> LOCATION: (11)..(11)
<223> OTHER INFORMATION: Xaa is Tyr, Leu or Ser
<220> FEATURE:
<221> NAME/KEY: VARIANT
<222> LOCATION: (12)..(12)
<223> OTHER INFORMATION: Xaa is Ser or Leu
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Met, Leu or Ser
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Lys, Gly, Ser or Glu
<220> FEATURE:
<221> NAME/KEY: VARIANT
<222> LOCATION: (18)..(18)
<223> OTHER INFORMATION: Xaa is Ile, Lys, Gln, Arg or Glu
<220> FEATURE:
<221> NAME/KEY: VARIANT
<222> LOCATION: (20)..(20)
<223> OTHER INFORMATION: Xaa is Gln, Ala, Glu or Lys
<220> FEATURE:
<221> NAME/KEY: VARIANT
<222> LOCATION: (21)..(21)
<223> OTHER INFORMATION: Xaa is Gln, Lys or Arg
<220> FEATURE:
<221> NAME/KEY: VARIANT
<222> LOCATION: (22)..(22)
<223> OTHER INFORMATION: Xaa is Asp, Ala or Glu
<220> FEATURE:
<221> NAME/KEY: VARIANT
<222> LOCATION: (23)..(23)
<223> OTHER INFORMATION: Xaa is Phe or 1Nal
<220> FEATURE:
<221> NAME/KEY: VARIANT
<222> LOCATION: (24)..(24)
<223> OTHER INFORMATION: Xaa is Val, Ile or Leu
<220> FEATURE:
<221> NAME/KEY: VARIANT
<222> LOCATION: (25)..(25)
<223> OTHER INFORMATION: Xaa is Asn, Glu, Arg or Lys
<220> FEATURE:
```

```
<221> NAME/KEY: VARIANT
<222> LOCATION: (28)..(28)
<223> OTHER INFORMATION: Xaa is Leu, Val, Ile, Lys, Glu or Ser
<220> FEATURE:
<221> NAME/KEY: VARIANT
<222> LOCATION: (29)..(29)
<223> OTHER INFORMATION: Xaa is Ala, Ser, Arg or Aib
<220> FEATURE:
<221> NAME/KEY: VARIANT
<222> LOCATION: (30)..(30)
<223> OTHER INFORMATION: Xaa is Gln, Aib, Glu, Lys or Tyr
<220> FEATURE:
<221> NAME/KEY: VARIANT
<222> LOCATION: (31)..(31)
<223> OTHER INFORMATION: Xaa is Lys, Gly, Pro or absent
<220> FEATURE:
<221> NAME/KEY: VARIANT
<222> LOCATION: (32)..(32)
<223> OTHER INFORMATION: Xaa is Gly, Pro, Ser, Glu or absent
<220> FEATURE:
<221> NAME/KEY: VARIANT
<222> LOCATION: (33)..(33)
<223> OTHER INFORMATION: Xaa is Lys, Ser or absent
<220> FEATURE:
<221> NAME/KEY: VARIANT
<222> LOCATION: (34)..(34)
<223> OTHER INFORMATION: Xaa is Lys, Ser, Glu or absent
<220> FEATURE:
<221> NAME/KEY: VARIANT
<222> LOCATION: (35)..(35)
<223> OTHER INFORMATION: Xaa is Asn, Gly, Ala, Lys or absent
<220> FEATURE:
<221> NAME/KEY: VARIANT
<222> LOCATION: (36)..(36)
<223> OTHER INFORMATION: Xaa is Asp, Ala, Pro, Glu or absent
<220> FEATURE:
<221> NAME/KEY: VARIANT
<222> LOCATION: (37)..(37)
<223> OTHER INFORMATION: Xaa is Trp, Pro, Lys or absent
<220> FEATURE:
<221> NAME/KEY: VARIANT
<222> LOCATION: (38)..(38)
<223> OTHER INFORMATION: Xaa is Lys, Pro, Glu or absent
<220> FEATURE:
<221> NAME/KEY: VARIANT
<222> LOCATION: (39)..(39)
<223> OTHER INFORMATION: Xaa is His, Pro, Ser, Lys or absent
<220> FEATURE:
<221> NAME/KEY: VARIANT
<222> LOCATION: (40)..(40)
<223> OTHER INFORMATION: Xaa is Asn, Ser or absent
<220> FEATURE:
<221> NAME/KEY: VARIANT
<222> LOCATION: (41)..(41)
<223> OTHER INFORMATION: Xaa is Ile or absent
<220> FEATURE:
<221> NAME/KEY: VARIANT
<222> LOCATION: (42)..(42)
<223> OTHER INFORMATION: Xaa is Thr or absent
<220> FEATURE:
<221> NAME/KEY: VARIANT
<222> LOCATION: (43)..(43)
<223> OTHER INFORMATION: Xaa is Gln or absent

<400> SEQUENCE: 80

Xaa Xaa Xaa Xaa Gly Thr Phe Xaa Ser Xaa Xaa Xaa Ile Xaa Xaa Xaa
1               5                   10                  15

Xaa Xaa Ala Xaa Xaa Xaa Xaa Xaa Xaa Trp Leu Xaa Xaa Xaa Xaa Xaa
            20                  25                  30

Xaa Xaa Xaa Xaa Xaa Xaa Xaa Xaa Xaa Xaa Xaa
            35                  40

<210> SEQ ID NO 81
<211> LENGTH: 41
<212> TYPE: PRT
```

```
<213> ORGANISM: Artificial sequence
<220> FEATURE:
<223> OTHER INFORMATION: Synthetic sequence: GIP Analogue: General
      Formula II(a) of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: VARIANT
<222> LOCATION: (3)..(3)
<223> OTHER INFORMATION: Xaa is Aib or Gly
<220> FEATURE:
<221> NAME/KEY: VARIANT
<222> LOCATION: (8)..(8)
<223> OTHER INFORMATION: Xaa is Thr, Ile or Ser
<220> FEATURE:
<221> NAME/KEY: VARIANT
<222> LOCATION: (11)..(11)
<223> OTHER INFORMATION: Xaa is Tyr, Leu or Ser
<220> FEATURE:
<221> NAME/KEY: VARIANT
<222> LOCATION: (12)..(12)
<223> OTHER INFORMATION: Xaa is Ser or Leu
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Leu
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Ser, Glu or Lys
<220> FEATURE:
<221> NAME/KEY: VARIANT
<222> LOCATION: (18)..(18)
<223> OTHER INFORMATION: Xaa is Ile or Lys
<220> FEATURE:
<221> NAME/KEY: VARIANT
<222> LOCATION: (20)..(20)
<223> OTHER INFORMATION: Xaa is Gln, Lys, Ala or Glu
<220> FEATURE:
<221> NAME/KEY: VARIANT
<222> LOCATION: (21)..(21)
<223> OTHER INFORMATION: Xaa is Lys or Arg
<220> FEATURE:
<221> NAME/KEY: VARIANT
<222> LOCATION: (22)..(22)
<223> OTHER INFORMATION: Xaa is Ala or Glu
<220> FEATURE:
<221> NAME/KEY: VARIANT
<222> LOCATION: (24)..(24)
<223> OTHER INFORMATION: Xaa is Val or Ile
<220> FEATURE:
<221> NAME/KEY: VARIANT
<222> LOCATION: (25)..(25)
<223> OTHER INFORMATION: Xaa is Asn or Glu
<220> FEATURE:
<221> NAME/KEY: VARIANT
<222> LOCATION: (28)..(28)
<223> OTHER INFORMATION: Xaa is Leu, Glu, Ser, Lys or Val
<220> FEATURE:
<221> NAME/KEY: VARIANT
<222> LOCATION: (29)..(29)
<223> OTHER INFORMATION: Xaa is Aib, Ala, Ser or Arg
<220> FEATURE:
<221> NAME/KEY: VARIANT
<222> LOCATION: (30)..(30)
<223> OTHER INFORMATION: Xaa is Aib, Glu or Lys
<220> FEATURE:
<221> NAME/KEY: VARIANT
<222> LOCATION: (31)..(31)
```

-continued

```
<223> OTHER INFORMATION: Xaa is Lys, Gly or absent
<220> FEATURE:
<221> NAME/KEY: VARIANT
<222> LOCATION: (32)..(41)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 81

Xaa Tyr Xaa Glu Gly Thr Phe Xaa Ser Asp Xaa Xaa Ile Xaa Xaa Xaa
1               5                   10                  15

Xaa Xaa Ala Xaa Xaa Xaa Phe Xaa Xaa Trp Leu Xaa Xaa Xaa Xaa Xaa
            20                  25                  30

Xaa Xaa Xaa Xaa Xaa Xaa Xaa Xaa Xaa
        35                  40

<210> SEQ ID NO 82
<211> LENGTH: 43
<212> TYPE: PRT
<213> ORGANISM: Artificial sequence
<220> FEATURE:
<223> OTHER INFORMATION: Synthetic sequence: GIP Analogue: General
      Formula I of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: VARIANT
<222> LOCATION: (2)..(2)
<223> OTHER INFORMATION: Xaa is His or Tyr
<220> FEATURE:
<221> NAME/KEY: VARIANT
<222> LOCATION: (3)..(3)
<223> OTHER INFORMATION: Xaa is Ala, Aib or Gly
<220> FEATURE:
<221> NAME/KEY: VARIANT
<222> LOCATION: (4)..(4)
<223> OTHER INFORMATION: Xaa is Glu or Asp
<220> FEATURE:
<221> NAME/KEY: VARIANT
<222> LOCATION: (8)..(8)
<223> OTHER INFORMATION: Xaa is Thr, Ser or Ile
<220> FEATURE:
<221> NAME/KEY: VARIANT
<222> LOCATION: (10)..(10)
<223> OTHER INFORMATION: Xaa is Asp or Glu
<220> FEATURE:
<221> NAME/KEY: VARIANT
<222> LOCATION: (11)..(11)
<223> OTHER INFORMATION: Xaa is Tyr, Leu or Ser
<220> FEATURE:
<221> NAME/KEY: VARIANT
<222> LOCATION: (12)..(12)
<223> OTHER INFORMATION: Xaa is Ser or Leu
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Met, Leu or Ser
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Lys, Gly, Ser or Glu
<220> FEATURE:
<221> NAME/KEY: VARIANT
<222> LOCATION: (18)..(18)
<223> OTHER INFORMATION: Xaa is Ile, Lys, Gln, Arg or Glu
```

```
<220> FEATURE:
<221> NAME/KEY: VARIANT
<222> LOCATION: (20)..(20)
<223> OTHER INFORMATION: Xaa is Gln, Ala, Glu or Lys
<220> FEATURE:
<221> NAME/KEY: VARIANT
<222> LOCATION: (21)..(21)
<223> OTHER INFORMATION: Xaa is Gln, Lys or Arg
<220> FEATURE:
<221> NAME/KEY: VARIANT
<222> LOCATION: (22)..(22)
<223> OTHER INFORMATION: Xaa is Asp, Ala or Glu
<220> FEATURE:
<221> NAME/KEY: VARIANT
<222> LOCATION: (23)..(23)
<223> OTHER INFORMATION: Xaa is Phe or 1Nal
<220> FEATURE:
<221> NAME/KEY: VARIANT
<222> LOCATION: (24)..(24)
<223> OTHER INFORMATION: Xaa is Val, Ile or Leu
<220> FEATURE:
<221> NAME/KEY: VARIANT
<222> LOCATION: (25)..(25)
<223> OTHER INFORMATION: Xaa is Asn, Glu, Arg or Lys
<220> FEATURE:
<221> NAME/KEY: VARIANT
<222> LOCATION: (28)..(28)
<223> OTHER INFORMATION: Xaa is Leu, Val, Ile, Lys, Glu or Ser
<220> FEATURE:
<221> NAME/KEY: VARIANT
<222> LOCATION: (29)..(29)
<223> OTHER INFORMATION: Xaa is Ala, Ser, Arg or Aib
<220> FEATURE:
<221> NAME/KEY: VARIANT
<222> LOCATION: (30)..(30)
<223> OTHER INFORMATION: Xaa is Gln, Aib, Glu, Lys, Gly or Tyr
<220> FEATURE:
<221> NAME/KEY: VARIANT
<222> LOCATION: (31)..(31)
<223> OTHER INFORMATION: Xaa is Lys, Gly, Pro or absent
<220> FEATURE:
<221> NAME/KEY: VARIANT
<222> LOCATION: (32)..(32)
<223> OTHER INFORMATION: Xaa is Gly, Pro, Ser, Glu or absent
<220> FEATURE:
<221> NAME/KEY: VARIANT
<222> LOCATION: (33)..(33)
<223> OTHER INFORMATION: Xaa is Lys, Ser or absent
<220> FEATURE:
<221> NAME/KEY: VARIANT
<222> LOCATION: (34)..(34)
<223> OTHER INFORMATION: Xaa is Lys, Ser, Glu or absent
<220> FEATURE:
<221> NAME/KEY: VARIANT
<222> LOCATION: (35)..(35)
<223> OTHER INFORMATION: Xaa is Asn, Gly, Ala, Lys or absent
<220> FEATURE:
<221> NAME/KEY: VARIANT
<222> LOCATION: (36)..(36)
<223> OTHER INFORMATION: Xaa is Asp, Ala, Pro, Glu or absent
<220> FEATURE:
<221> NAME/KEY: VARIANT
<222> LOCATION: (37)..(37)
<223> OTHER INFORMATION: Xaa is Trp, Pro, Lys or absent
<220> FEATURE:
<221> NAME/KEY: VARIANT
<222> LOCATION: (38)..(38)
<223> OTHER INFORMATION: Xaa is Lys, Pro, Glu or absent
<220> FEATURE:
<221> NAME/KEY: VARIANT
<222> LOCATION: (39)..(39)
<223> OTHER INFORMATION: Xaa is His, Pro, Ser, Lys or absent
<220> FEATURE:
<221> NAME/KEY: VARIANT
<222> LOCATION: (40)..(40)
<223> OTHER INFORMATION: Xaa is Asn, Ser or absent
<220> FEATURE:
<221> NAME/KEY: VARIANT
<222> LOCATION: (41)..(41)
```

-continued

```
<223> OTHER INFORMATION: Xaa is Ile or absent
<220> FEATURE:
<221> NAME/KEY: VARIANT
<222> LOCATION: (42)..(42)
<223> OTHER INFORMATION: Xaa is Thr or absent
<220> FEATURE:
<221> NAME/KEY: VARIANT
<222> LOCATION: (43)..(43)
<223> OTHER INFORMATION: Xaa is Gln or absent

<400> SEQUENCE: 82

Xaa Xaa Xaa Xaa Gly Thr Phe Xaa Ser Xaa Xaa Xaa Ile Xaa Xaa Xaa
1               5                   10                  15

Xaa Xaa Ala Xaa Xaa Xaa Xaa Xaa Xaa Trp Leu Xaa Xaa Xaa Xaa Xaa
            20                  25                  30

Xaa Xaa Xaa Xaa Xaa Xaa Xaa Xaa Xaa Xaa Xaa
        35                  40

<210> SEQ ID NO 83
<211> LENGTH: 41
<212> TYPE: PRT
<213> ORGANISM: Artificial sequence
<220> FEATURE:
<223> OTHER INFORMATION: Synthetic sequence: GIP Analogue: General
      Formula II of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: VARIANT
<222> LOCATION: (3)..(3)
<223> OTHER INFORMATION: Xaa is Aib or Gly
<220> FEATURE:
<221> NAME/KEY: VARIANT
<222> LOCATION: (8)..(8)
<223> OTHER INFORMATION: Xaa is Thr, Ile or Ser
<220> FEATURE:
<221> NAME/KEY: VARIANT
<222> LOCATION: (11)..(11)
<223> OTHER INFORMATION: Xaa is Tyr, Leu or Ser
<220> FEATURE:
<221> NAME/KEY: VARIANT
<222> LOCATION: (12)..(12)
<223> OTHER INFORMATION: Xaa is Ser or Leu
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Leu
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Ser, Glu or Lys
<220> FEATURE:
<221> NAME/KEY: VARIANT
<222> LOCATION: (18)..(18)
<223> OTHER INFORMATION: Xaa is Ile or Lys
<220> FEATURE:
<221> NAME/KEY: VARIANT
<222> LOCATION: (20)..(20)
<223> OTHER INFORMATION: Xaa is Gln, Lys, Ala or Glu
<220> FEATURE:
<221> NAME/KEY: VARIANT
<222> LOCATION: (21)..(21)
<223> OTHER INFORMATION: Xaa is Lys or Arg
<220> FEATURE:
<221> NAME/KEY: VARIANT
```

```
<222> LOCATION: (22)..(22)
<223> OTHER INFORMATION: Xaa is Ala or Glu
<220> FEATURE:
<221> NAME/KEY: VARIANT
<222> LOCATION: (24)..(24)
<223> OTHER INFORMATION: Xaa is Val or Ile
<220> FEATURE:
<221> NAME/KEY: VARIANT
<222> LOCATION: (25)..(25)
<223> OTHER INFORMATION: Xaa is Asn or Glu
<220> FEATURE:
<221> NAME/KEY: VARIANT
<222> LOCATION: (28)..(28)
<223> OTHER INFORMATION: Xaa is Leu, Glu, Ser, Lys or Val
<220> FEATURE:
<221> NAME/KEY: VARIANT
<222> LOCATION: (29)..(29)
<223> OTHER INFORMATION: Xaa is Aib, Ala, Ser or Arg
<220> FEATURE:
<221> NAME/KEY: VARIANT
<222> LOCATION: (30)..(30)
<223> OTHER INFORMATION: Xaa is Aib, Glu, Gly or Lys
<220> FEATURE:
<221> NAME/KEY: VARIANT
<222> LOCATION: (31)..(31)
<223> OTHER INFORMATION: Xaa is Lys, Gly or absent
<220> FEATURE:
<221> NAME/KEY: VARIANT
<222> LOCATION: (32)..(41)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 83

Xaa Tyr Xaa Glu Gly Thr Phe Xaa Ser Asp Xaa Xaa Ile Xaa Xaa Xaa
1               5                   10                  15

Xaa Xaa Ala Xaa Xaa Xaa Phe Xaa Xaa Trp Leu Xaa Xaa Xaa Xaa Xaa
            20                  25                  30

Xaa Xaa Xaa Xaa Xaa Xaa Xaa Xaa Xaa
        35                  40

<210> SEQ ID NO 84
<211> LENGTH: 43
<212> TYPE: PRT
<213> ORGANISM: Artificial sequence
<220> FEATURE:
<223> OTHER INFORMATION: Synthetic sequence: GIP Analogue: General
      Formula I' of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: VARIANT
<222> LOCATION: (3)..(3)
<223> OTHER INFORMATION: Xaa is Ala, Aib or Gly
<220> FEATURE:
<221> NAME/KEY: VARIANT
<222> LOCATION: (4)..(4)
<223> OTHER INFORMATION: Xaa is Glu or Asp
<220> FEATURE:
<221> NAME/KEY: VARIANT
<222> LOCATION: (8)..(8)
<223> OTHER INFORMATION: Xaa is Thr, Ser or Ile
<220> FEATURE:
<221> NAME/KEY: VARIANT
<222> LOCATION: (10)..(10)
<223> OTHER INFORMATION: Xaa is Asp or Glu
<220> FEATURE:
<221> NAME/KEY: VARIANT
<222> LOCATION: (11)..(11)
<223> OTHER INFORMATION: Xaa is Tyr, Leu or Ser
<220> FEATURE:
<221> NAME/KEY: VARIANT
<222> LOCATION: (12)..(12)
```

```
<223> OTHER INFORMATION: Xaa is Ser or Leu
<220> FEATURE:
<221> NAME/KEY: VARIANT
<222> LOCATION: (13)..(13)
<223> OTHER INFORMATION: Xaa is Ile or Lys
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Met, Leu or Ser
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Lys, Gly, Ser or Glu
<220> FEATURE:
<221> NAME/KEY: VARIANT
<222> LOCATION: (20)..(20)
<223> OTHER INFORMATION: Xaa is Gln, Ala, Glu or Lys
<220> FEATURE:
<221> NAME/KEY: VARIANT
<222> LOCATION: (21)..(21)
<223> OTHER INFORMATION: Xaa is Gln, Lys, Arg or His
<220> FEATURE:
<221> NAME/KEY: VARIANT
<222> LOCATION: (22)..(22)
<223> OTHER INFORMATION: Xaa is Asp, Ala or Glu
<220> FEATURE:
<221> NAME/KEY: VARIANT
<222> LOCATION: (23)..(23)
<223> OTHER INFORMATION: Xaa is Phe or 1Nal
<220> FEATURE:
<221> NAME/KEY: VARIANT
<222> LOCATION: (24)..(24)
<223> OTHER INFORMATION: Xaa is Val, Ile or Leu
<220> FEATURE:
<221> NAME/KEY: VARIANT
<222> LOCATION: (25)..(25)
<223> OTHER INFORMATION: Xaa is Asn, Glu, Arg or Lys
<220> FEATURE:
<221> NAME/KEY: VARIANT
<222> LOCATION: (28)..(28)
<223> OTHER INFORMATION: Xaa is Leu, Val, Ile, Lys, Glu or Ser
<220> FEATURE:
<221> NAME/KEY: VARIANT
<222> LOCATION: (29)..(29)
<223> OTHER INFORMATION: Xaa is Ala, Ser, Arg or Aib
<220> FEATURE:
<221> NAME/KEY: VARIANT
<222> LOCATION: (30)..(30)
<223> OTHER INFORMATION: Xaa is Gln, Aib, Lys, Gly or Ala
<220> FEATURE:
<221> NAME/KEY: VARIANT
<222> LOCATION: (31)..(31)
<223> OTHER INFORMATION: Xaa is Lys, Gly, Pro or absent
<220> FEATURE:
<221> NAME/KEY: VARIANT
<222> LOCATION: (32)..(32)
<223> OTHER INFORMATION: Xaa is Gly, Pro, Ser, Glu or absent
<220> FEATURE:
<221> NAME/KEY: VARIANT
<222> LOCATION: (33)..(33)
<223> OTHER INFORMATION: Xaa is Lys, Ser or absent
<220> FEATURE:
<221> NAME/KEY: VARIANT
<222> LOCATION: (34)..(34)
<223> OTHER INFORMATION: Xaa is Lys, Ser, Glu or absent
<220> FEATURE:
<221> NAME/KEY: VARIANT
<222> LOCATION: (35)..(35)
<223> OTHER INFORMATION: Xaa is Asn, Gly, Ala, Lys or absent
<220> FEATURE:
<221> NAME/KEY: VARIANT
```

```
<222> LOCATION: (36)..(36)
<223> OTHER INFORMATION: Xaa is Asp, Ala, Pro, Glu or absent
<220> FEATURE:
<221> NAME/KEY: VARIANT
<222> LOCATION: (37)..(37)
<223> OTHER INFORMATION: Xaa is Trp, Pro, Lys or absent
<220> FEATURE:
<221> NAME/KEY: VARIANT
<222> LOCATION: (38)..(38)
<223> OTHER INFORMATION: Xaa is Lys, Pro, Glu or absent
<220> FEATURE:
<221> NAME/KEY: VARIANT
<222> LOCATION: (39)..(39)
<223> OTHER INFORMATION: Xaa is His, Pro, Ser, Lys or absent
<220> FEATURE:
<221> NAME/KEY: VARIANT
<222> LOCATION: (40)..(40)
<223> OTHER INFORMATION: Xaa is Asn, Ser or absent
<220> FEATURE:
<221> NAME/KEY: VARIANT
<222> LOCATION: (41)..(41)
<223> OTHER INFORMATION: Xaa is Ile or absent
<220> FEATURE:
<221> NAME/KEY: VARIANT
<222> LOCATION: (42)..(42)
<223> OTHER INFORMATION: Xaa is Thr or absent
<220> FEATURE:
<221> NAME/KEY: VARIANT
<222> LOCATION: (43)..(43)
<223> OTHER INFORMATION: Xaa is Gln or absent

<400> SEQUENCE: 84

Xaa Tyr Xaa Xaa Gly Thr Phe Xaa Ser Xaa Xaa Xaa Xaa Xaa Xaa
1               5                   10                  15

Xaa Lys Ala Xaa Xaa Xaa Xaa Xaa Xaa Trp Leu Xaa Xaa Xaa Xaa Xaa
            20                  25                  30

Xaa Xaa Xaa Xaa Xaa Xaa Xaa Xaa Xaa Xaa Xaa
        35                  40

<210> SEQ ID NO 85
<211> LENGTH: 43
<212> TYPE: PRT
<213> ORGANISM: Artificial sequence
<220> FEATURE:
<223> OTHER INFORMATION: Synthetic sequence: GIP Analogue: General
      Formula I(a)' of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: VARIANT
<222> LOCATION: (3)..(3)
<223> OTHER INFORMATION: Xaa is Ala, Aib or Gly
<220> FEATURE:
<221> NAME/KEY: VARIANT
<222> LOCATION: (4)..(4)
<223> OTHER INFORMATION: Xaa is Glu or Asp
<220> FEATURE:
<221> NAME/KEY: VARIANT
<222> LOCATION: (8)..(8)
<223> OTHER INFORMATION: Xaa is Thr, Ser or Ile
<220> FEATURE:
<221> NAME/KEY: VARIANT
<222> LOCATION: (10)..(10)
<223> OTHER INFORMATION: Xaa is Asp or Glu
<220> FEATURE:
<221> NAME/KEY: VARIANT
<222> LOCATION: (11)..(11)
<223> OTHER INFORMATION: Xaa is Tyr, Leu or Ser
<220> FEATURE:
<221> NAME/KEY: VARIANT
<222> LOCATION: (12)..(12)
<223> OTHER INFORMATION: Xaa is Ser or Leu
<220> FEATURE:
```

```
<221> NAME/KEY: VARIANT
<222> LOCATION: (13)..(13)
<223> OTHER INFORMATION: Xaa is Ile or Lys
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Leu or Ser
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Lys, Gly, Ser or Glu
<220> FEATURE:
<221> NAME/KEY: VARIANT
<222> LOCATION: (20)..(20)
<223> OTHER INFORMATION: Xaa is Gln, Ala, Glu or Lys
<220> FEATURE:
<221> NAME/KEY: VARIANT
<222> LOCATION: (21)..(21)
<223> OTHER INFORMATION: Xaa is Gln, Lys, Arg or His
<220> FEATURE:
<221> NAME/KEY: VARIANT
<222> LOCATION: (22)..(22)
<223> OTHER INFORMATION: Xaa is Asp, Ala or Glu
<220> FEATURE:
<221> NAME/KEY: VARIANT
<222> LOCATION: (23)..(23)
<223> OTHER INFORMATION: Xaa is Phe or 1Nal
<220> FEATURE:
<221> NAME/KEY: VARIANT
<222> LOCATION: (24)..(24)
<223> OTHER INFORMATION: Xaa is Val, Ile or Leu
<220> FEATURE:
<221> NAME/KEY: VARIANT
<222> LOCATION: (25)..(25)
<223> OTHER INFORMATION: Xaa is Asn, Glu, Arg or Lys
<220> FEATURE:
<221> NAME/KEY: VARIANT
<222> LOCATION: (28)..(28)
<223> OTHER INFORMATION: Xaa is Leu, Val, Ile, Lys, Glu or Ser
<220> FEATURE:
<221> NAME/KEY: VARIANT
<222> LOCATION: (29)..(29)
<223> OTHER INFORMATION: Xaa is Ala, Ser, Arg or Aib
<220> FEATURE:
<221> NAME/KEY: VARIANT
<222> LOCATION: (30)..(30)
<223> OTHER INFORMATION: Xaa is Gln, Aib, Lys, Gly or Ala
<220> FEATURE:
<221> NAME/KEY: VARIANT
<222> LOCATION: (31)..(31)
<223> OTHER INFORMATION: Xaa is Lys, Gly, Pro or absent
<220> FEATURE:
<221> NAME/KEY: VARIANT
<222> LOCATION: (32)..(32)
<223> OTHER INFORMATION: Xaa is Gly, Pro, Ser, Glu or absent
<220> FEATURE:
<221> NAME/KEY: VARIANT
<222> LOCATION: (33)..(33)
<223> OTHER INFORMATION: Xaa is Lys, Ser or absent
<220> FEATURE:
<221> NAME/KEY: VARIANT
<222> LOCATION: (34)..(34)
<223> OTHER INFORMATION: Xaa is Lys, Ser, Glu or absent
<220> FEATURE:
<221> NAME/KEY: VARIANT
<222> LOCATION: (35)..(35)
<223> OTHER INFORMATION: Xaa is Asn, Gly, Ala, Lys or absent
<220> FEATURE:
<221> NAME/KEY: VARIANT
<222> LOCATION: (36)..(36)
<223> OTHER INFORMATION: Xaa is Asp, Ala, Pro, Glu or absent
```

-continued

```
<220> FEATURE:
<221> NAME/KEY: VARIANT
<222> LOCATION: (37)..(37)
<223> OTHER INFORMATION: Xaa is Trp, Pro, Lys or absent
<220> FEATURE:
<221> NAME/KEY: VARIANT
<222> LOCATION: (38)..(38)
<223> OTHER INFORMATION: Xaa is Lys, Pro, Glu or absent
<220> FEATURE:
<221> NAME/KEY: VARIANT
<222> LOCATION: (39)..(39)
<223> OTHER INFORMATION: Xaa is His, Pro, Ser, Lys or absent
<220> FEATURE:
<221> NAME/KEY: VARIANT
<222> LOCATION: (40)..(40)
<223> OTHER INFORMATION: Xaa is Asn, Ser or absent
<220> FEATURE:
<221> NAME/KEY: VARIANT
<222> LOCATION: (41)..(41)
<223> OTHER INFORMATION: Xaa is Ile or absent
<220> FEATURE:
<221> NAME/KEY: VARIANT
<222> LOCATION: (42)..(42)
<223> OTHER INFORMATION: Xaa is Thr or absent
<220> FEATURE:
<221> NAME/KEY: VARIANT
<222> LOCATION: (43)..(43)
<223> OTHER INFORMATION: Xaa is Gln or absent

<400> SEQUENCE: 85

Xaa Tyr Xaa Xaa Gly Thr Phe Xaa Ser Xaa Xaa Xaa Xaa Xaa Xaa
1               5                   10                  15

Xaa Lys Ala Xaa Xaa Xaa Xaa Xaa Xaa Trp Leu Xaa Xaa Xaa Xaa Xaa
                20                  25                  30

Xaa Xaa Xaa Xaa Xaa Xaa Xaa Xaa Xaa Xaa Xaa
        35                  40

<210> SEQ ID NO 86
<211> LENGTH: 43
<212> TYPE: PRT
<213> ORGANISM: Artificial sequence
<220> FEATURE:
<223> OTHER INFORMATION: Synthetic sequence: GIP Analogue: General
      Formula I(b)' of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: VARIANT
<222> LOCATION: (3)..(3)
<223> OTHER INFORMATION: Xaa is Ala, Aib or Gly
<220> FEATURE:
<221> NAME/KEY: VARIANT
<222> LOCATION: (4)..(4)
<223> OTHER INFORMATION: Xaa is Glu or Asp
<220> FEATURE:
<221> NAME/KEY: VARIANT
<222> LOCATION: (8)..(8)
<223> OTHER INFORMATION: Xaa is Thr or Ser
<220> FEATURE:
<221> NAME/KEY: VARIANT
<222> LOCATION: (10)..(10)
<223> OTHER INFORMATION: Xaa is Asp or Glu
<220> FEATURE:
<221> NAME/KEY: VARIANT
<222> LOCATION: (11)..(11)
<223> OTHER INFORMATION: Xaa is Tyr or Leu
<220> FEATURE:
<221> NAME/KEY: VARIANT
<222> LOCATION: (12)..(12)
<223> OTHER INFORMATION: Xaa is Ser or Leu
<220> FEATURE:
<221> NAME/KEY: VARIANT
<222> LOCATION: (13)..(13)
```

```
<223> OTHER INFORMATION: Xaa is Ile or Lys
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (15)..(15)
<223> OTHER INFORMATION: Xaa is Leu or Ser
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Lys, Ser or Glu
<220> FEATURE:
<221> NAME/KEY: VARIANT
<222> LOCATION: (20)..(20)
<223> OTHER INFORMATION: Xaa is Gln, Ala, Glu or Lys
<220> FEATURE:
<221> NAME/KEY: VARIANT
<222> LOCATION: (21)..(21)
<223> OTHER INFORMATION: Xaa is Gln, Lys, Arg or His
<220> FEATURE:
<221> NAME/KEY: VARIANT
<222> LOCATION: (22)..(22)
<223> OTHER INFORMATION: Xaa is Asp, Ala or Glu
<220> FEATURE:
<221> NAME/KEY: VARIANT
<222> LOCATION: (24)..(24)
<223> OTHER INFORMATION: Xaa is Val, Ile or Leu
<220> FEATURE:
<221> NAME/KEY: VARIANT
<222> LOCATION: (25)..(25)
<223> OTHER INFORMATION: Xaa is Asn, Glu, Arg or Lys
<220> FEATURE:
<221> NAME/KEY: VARIANT
<222> LOCATION: (28)..(28)
<223> OTHER INFORMATION: Xaa is Leu, Glu, Val or Ile
<220> FEATURE:
<221> NAME/KEY: VARIANT
<222> LOCATION: (29)..(29)
<223> OTHER INFORMATION: Xaa is Ala, Ser, Arg or Aib
<220> FEATURE:
<221> NAME/KEY: VARIANT
<222> LOCATION: (30)..(30)
<223> OTHER INFORMATION: Xaa is Gln, Gly, Aib or Ala
<220> FEATURE:
<221> NAME/KEY: VARIANT
<222> LOCATION: (31)..(31)
<223> OTHER INFORMATION: Xaa is Lys, Gly, Pro or absent
<220> FEATURE:
<221> NAME/KEY: VARIANT
<222> LOCATION: (32)..(32)
<223> OTHER INFORMATION: Xaa is Gly, Pro, Ser, Glu or absent
<220> FEATURE:
<221> NAME/KEY: VARIANT
<222> LOCATION: (33)..(33)
<223> OTHER INFORMATION: Xaa is Lys, Ser or absent
<220> FEATURE:
<221> NAME/KEY: VARIANT
<222> LOCATION: (34)..(34)
<223> OTHER INFORMATION: Xaa is Lys, Ser, Glu or absent
<220> FEATURE:
<221> NAME/KEY: VARIANT
<222> LOCATION: (35)..(35)
<223> OTHER INFORMATION: Xaa is Asn, Gly, Ala, Lys or absent
<220> FEATURE:
<221> NAME/KEY: VARIANT
<222> LOCATION: (36)..(36)
<223> OTHER INFORMATION: Xaa is Asp, Ala, Pro, Glu or absent
<220> FEATURE:
<221> NAME/KEY: VARIANT
<222> LOCATION: (37)..(37)
<223> OTHER INFORMATION: Xaa is Trp, Pro, Lys or absent
<220> FEATURE:
<221> NAME/KEY: VARIANT
```

```
<222> LOCATION: (38)..(38)
<223> OTHER INFORMATION: Xaa is Lys, Pro, Glu or absent
<220> FEATURE:
<221> NAME/KEY: VARIANT
<222> LOCATION: (39)..(39)
<223> OTHER INFORMATION: Xaa is His, Pro, Ser, Lys or absent
<220> FEATURE:
<221> NAME/KEY: VARIANT
<222> LOCATION: (40)..(40)
<223> OTHER INFORMATION: Xaa is Asn, Ser or absent
<220> FEATURE:
<221> NAME/KEY: VARIANT
<222> LOCATION: (41)..(41)
<223> OTHER INFORMATION: Xaa is Ile or absent
<220> FEATURE:
<221> NAME/KEY: VARIANT
<222> LOCATION: (42)..(42)
<223> OTHER INFORMATION: Xaa is Thr or absent
<220> FEATURE:
<221> NAME/KEY: VARIANT
<222> LOCATION: (43)..(43)
<223> OTHER INFORMATION: Xaa is Gln or absent

<400> SEQUENCE: 86

Xaa Tyr Xaa Xaa Gly Thr Phe Xaa Ser Xaa Xaa Xaa Xaa Xaa Xaa
1               5                   10                  15

Xaa Lys Ala Xaa Xaa Xaa Phe Xaa Xaa Trp Leu Xaa Xaa Xaa Xaa Xaa
                20                  25                  30

Xaa Xaa Xaa Xaa Xaa Xaa Xaa Xaa Xaa Xaa Xaa
        35                  40

<210> SEQ ID NO 87
<211> LENGTH: 41
<212> TYPE: PRT
<213> ORGANISM: Artificial sequence
<220> FEATURE:
<223> OTHER INFORMATION: Synthetic sequence: GIP Analogue: General
      Formula II' of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: VARIANT
<222> LOCATION: (3)..(3)
<223> OTHER INFORMATION: Xaa is Aib or Gly
<220> FEATURE:
<221> NAME/KEY: VARIANT
<222> LOCATION: (8)..(8)
<223> OTHER INFORMATION: Xaa is Thr, Ile or Ser
<220> FEATURE:
<221> NAME/KEY: VARIANT
<222> LOCATION: (11)..(11)
<223> OTHER INFORMATION: Xaa is Tyr or Leu
<220> FEATURE:
<221> NAME/KEY: VARIANT
<222> LOCATION: (12)..(12)
<223> OTHER INFORMATION: Xaa is Ser or Leu
<220> FEATURE:
<221> NAME/KEY: VARIANT
<222> LOCATION: (13)..(13)
<223> OTHER INFORMATION: Xaa is Ile or Lys
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Ser, Glu or Lys
<220> FEATURE:
```

```
<221> NAME/KEY: VARIANT
<222> LOCATION: (20)..(20)
<223> OTHER INFORMATION: Xaa is Gln or Ala
<220> FEATURE:
<221> NAME/KEY: VARIANT
<222> LOCATION: (21)..(21)
<223> OTHER INFORMATION: Xaa is Lys, His or Arg
<220> FEATURE:
<221> NAME/KEY: VARIANT
<222> LOCATION: (22)..(22)
<223> OTHER INFORMATION: Xaa is Ala, Asp or Glu
<220> FEATURE:
<221> NAME/KEY: VARIANT
<222> LOCATION: (24)..(24)
<223> OTHER INFORMATION: Xaa is Val or Ile
<220> FEATURE:
<221> NAME/KEY: VARIANT
<222> LOCATION: (25)..(25)
<223> OTHER INFORMATION: Xaa is Asn, Lys or Glu
<220> FEATURE:
<221> NAME/KEY: VARIANT
<222> LOCATION: (28)..(28)
<223> OTHER INFORMATION: Xaa is Leu, Glu, Val or Ile
<220> FEATURE:
<221> NAME/KEY: VARIANT
<222> LOCATION: (29)..(29)
<223> OTHER INFORMATION: Xaa is Aib, Ala, Ser or Arg
<220> FEATURE:
<221> NAME/KEY: VARIANT
<222> LOCATION: (30)..(30)
<223> OTHER INFORMATION: Xaa is Gln, Aib, Ala, Gly or Lys
<220> FEATURE:
<221> NAME/KEY: VARIANT
<222> LOCATION: (31)..(31)
<223> OTHER INFORMATION: Xaa is Lys, Gly or absent
<220> FEATURE:
<221> NAME/KEY: VARIANT
<222> LOCATION: (32)..(41)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 87

Xaa Tyr Xaa Glu Gly Thr Phe Xaa Ser Asp Xaa Xaa Xaa Xaa Leu Xaa
1               5                   10                  15

Xaa Lys Ala Xaa Xaa Xaa Phe Xaa Xaa Trp Leu Xaa Xaa Xaa Xaa Xaa
            20                  25                  30

Xaa Xaa Xaa Xaa Xaa Xaa Xaa Xaa Xaa
        35                  40

<210> SEQ ID NO 88
<211> LENGTH: 41
<212> TYPE: PRT
<213> ORGANISM: Artificial sequence
<220> FEATURE:
<223> OTHER INFORMATION: Synthetic sequence: GIP Analogue: General
      Formula II(a)' of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: VARIANT
<222> LOCATION: (3)..(3)
<223> OTHER INFORMATION: Xaa is Aib or Gly
<220> FEATURE:
<221> NAME/KEY: VARIANT
<222> LOCATION: (8)..(8)
<223> OTHER INFORMATION: Xaa is Thr, Ile or Ser
<220> FEATURE:
<221> NAME/KEY: VARIANT
<222> LOCATION: (11)..(11)
<223> OTHER INFORMATION: Xaa is Tyr or Leu
<220> FEATURE:
<221> NAME/KEY: VARIANT
```

```
<222> LOCATION: (12)..(12)
<223> OTHER INFORMATION: Xaa is Ser or Leu
<220> FEATURE:
<221> NAME/KEY: VARIANT
<222> LOCATION: (14)..(14)
<223> OTHER INFORMATION: Xaa is Ala, Tyr or Aib
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Ser, Glu or Lys
<220> FEATURE:
<221> NAME/KEY: VARIANT
<222> LOCATION: (20)..(20)
<223> OTHER INFORMATION: Xaa is Gln, Lys, Ala or Glu
<220> FEATURE:
<221> NAME/KEY: VARIANT
<222> LOCATION: (21)..(21)
<223> OTHER INFORMATION: Xaa is Lys, His or Arg
<220> FEATURE:
<221> NAME/KEY: VARIANT
<222> LOCATION: (22)..(22)
<223> OTHER INFORMATION: Xaa is Ala, Asp or Glu
<220> FEATURE:
<221> NAME/KEY: VARIANT
<222> LOCATION: (24)..(24)
<223> OTHER INFORMATION: Xaa is Val or Ile
<220> FEATURE:
<221> NAME/KEY: VARIANT
<222> LOCATION: (25)..(25)
<223> OTHER INFORMATION: Xaa is Asn, Lys or Glu
<220> FEATURE:
<221> NAME/KEY: VARIANT
<222> LOCATION: (28)..(28)
<223> OTHER INFORMATION: Xaa is Leu, Glu, Val or Ile
<220> FEATURE:
<221> NAME/KEY: VARIANT
<222> LOCATION: (29)..(29)
<223> OTHER INFORMATION: Xaa is Aib, Ala, Ser or Arg
<220> FEATURE:
<221> NAME/KEY: VARIANT
<222> LOCATION: (30)..(30)
<223> OTHER INFORMATION: Xaa is Gln, Aib, Ala, or Gly
<220> FEATURE:
<221> NAME/KEY: VARIANT
<222> LOCATION: (31)..(31)
<223> OTHER INFORMATION: Xaa is Lys, Gly or absent
<220> FEATURE:
<221> NAME/KEY: VARIANT
<222> LOCATION: (32)..(41)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 88

Xaa Tyr Xaa Glu Gly Thr Phe Xaa Ser Asp Xaa Xaa Ile Xaa Leu Xaa
1               5                   10                  15

Xaa Lys Ala Xaa Xaa Xaa Phe Xaa Xaa Trp Leu Xaa Xaa Xaa Xaa Xaa
            20                  25                  30

Xaa Xaa Xaa Xaa Xaa Xaa Xaa Xaa Xaa
        35                  40

<210> SEQ ID NO 89
<211> LENGTH: 41
<212> TYPE: PRT
<213> ORGANISM: Artificial sequence
<220> FEATURE:
<223> OTHER INFORMATION: Synthetic sequence: GIP Analogue: General
      Formula II(b)' of PCT/EP2013/059319
<220> FEATURE:
<221> NAME/KEY: VARIANT
<222> LOCATION: (1)..(1)
```

```
<223> OTHER INFORMATION: Xaa is Hy-, Ac or pGlu
<220> FEATURE:
<221> NAME/KEY: MOD_RES
<222> LOCATION: (3)..(3)
<223> OTHER INFORMATION: Aib
<220> FEATURE:
<221> NAME/KEY: VARIANT
<222> LOCATION: (8)..(8)
<223> OTHER INFORMATION: Xaa is Thr or Ser
<220> FEATURE:
<221> NAME/KEY: VARIANT
<222> LOCATION: (14)..(14)
<223> OTHER INFORMATION: Xaa is Ala or Tyr
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Lys, Glu or Ser
<220> FEATURE:
<221> NAME/KEY: VARIANT
<222> LOCATION: (21)..(21)
<223> OTHER INFORMATION: Xaa is Lys, His or Arg
<220> FEATURE:
<221> NAME/KEY: VARIANT
<222> LOCATION: (22)..(22)
<223> OTHER INFORMATION: Xaa is Ala, Asp or Glu
<220> FEATURE:
<221> NAME/KEY: VARIANT
<222> LOCATION: (24)..(24)
<223> OTHER INFORMATION: Xaa is Val or Ile
<220> FEATURE:
<221> NAME/KEY: VARIANT
<222> LOCATION: (28)..(28)
<223> OTHER INFORMATION: Xaa is Leu, Glu or Val
<220> FEATURE:
<221> NAME/KEY: VARIANT
<222> LOCATION: (29)..(29)
<223> OTHER INFORMATION: Xaa is Arg or Ser
<220> FEATURE:
<221> NAME/KEY: VARIANT
<222> LOCATION: (31)..(31)
<223> OTHER INFORMATION: Xaa is Lys, Gly or absent
<220> FEATURE:
<221> NAME/KEY: VARIANT
<222> LOCATION: (32)..(41)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 89

Xaa Tyr Ala Glu Gly Thr Phe Xaa Ser Asp Tyr Ser Ile Xaa Leu Xaa
1               5                   10                  15

Xaa Lys Ala Gln Xaa Xaa Phe Xaa Glu Trp Leu Xaa Xaa Ala Xaa Xaa
            20                  25                  30

Xaa Xaa Xaa Xaa Xaa Xaa Xaa Xaa Xaa
        35                  40

<210> SEQ ID NO 90
<211> LENGTH: 41
<212> TYPE: PRT
<213> ORGANISM: Artificial sequence
<220> FEATURE:
<223> OTHER INFORMATION: Synthetic sequence: GIP Analogue: General
      Formula II(c) of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: MOD_RES
<222> LOCATION: (3)..(3)
<223> OTHER INFORMATION: Aib
```

-continued

```
<220> FEATURE:
<221> NAME/KEY: VARIANT
<222> LOCATION: (8)..(8)
<223> OTHER INFORMATION: Xaa is Thr or Ser
<220> FEATURE:
<221> NAME/KEY: VARIANT
<222> LOCATION: (14)..(14)
<223> OTHER INFORMATION: Xaa is Ala, Aib or Tyr
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Glu, Lys or Ser
<220> FEATURE:
<221> NAME/KEY: VARIANT
<222> LOCATION: (21)..(21)
<223> OTHER INFORMATION: Xaa is Lys, His or Arg
<220> FEATURE:
<221> NAME/KEY: VARIANT
<222> LOCATION: (22)..(22)
<223> OTHER INFORMATION: Xaa is Ala, Asp or Glu
<220> FEATURE:
<221> NAME/KEY: VARIANT
<222> LOCATION: (25)..(25)
<223> OTHER INFORMATION: Xaa is Glu or Asn
<220> FEATURE:
<221> NAME/KEY: VARIANT
<222> LOCATION: (28)..(28)
<223> OTHER INFORMATION: Xaa is Leu, Glu or Val
<220> FEATURE:
<221> NAME/KEY: VARIANT
<222> LOCATION: (30)..(30)
<223> OTHER INFORMATION: Xaa is Gln or Aib
<220> FEATURE:
<221> NAME/KEY: VARIANT
<222> LOCATION: (31)..(31)
<223> OTHER INFORMATION: Xaa is Lys, Gly or absent
<220> FEATURE:
<221> NAME/KEY: VARIANT
<222> LOCATION: (32)..(41)
<223> OTHER INFORMATION: Y1, which may be present or absent. If present,
      up to 2 residues may be present or absent, and Y1 is SEQ ID NO:
      74, SEQ ID NO: 75, SEQ ID NO: 76, or SEQ ID NO: 77.

<400> SEQUENCE: 90

Xaa Tyr Ala Glu Gly Thr Phe Xaa Ser Asp Tyr Ser Ile Xaa Leu Xaa
1               5                   10                  15

Xaa Lys Ala Gln Xaa Xaa Phe Val Xaa Trp Leu Xaa Ala Xaa Xaa Xaa
                20                  25                  30

Xaa Xaa Xaa Xaa Xaa Xaa Xaa Xaa Xaa
            35                  40

<210> SEQ ID NO 91
<211> LENGTH: 41
<212> TYPE: PRT
<213> ORGANISM: Artificial sequence
<220> FEATURE:
<223> OTHER INFORMATION: Synthetic sequence: GIP Analogue: General
      Formula II(d) of PCT/EP2013/059319
<220> FEATURE:
<221> NAME/KEY: VARIANT
<222> LOCATION: (1)..(1)
<223> OTHER INFORMATION: Xaa is Hy-, Ac or pGlu
<220> FEATURE:
<221> NAME/KEY: MOD_RES
<222> LOCATION: (3)..(3)
<223> OTHER INFORMATION: Aib
<220> FEATURE:
<221> NAME/KEY: VARIANT
<222> LOCATION: (8)..(8)
<223> OTHER INFORMATION: Xaa is Thr or Ser
<220> FEATURE:
```

```
<221> NAME/KEY: VARIANT
<222> LOCATION: (14)..(14)
<223> OTHER INFORMATION: Xaa is Ala, Aib or Tyr
<220> FEATURE:
<221> NAME/KEY: VARIANT
<222> LOCATION: (16)..(16)
<223> OTHER INFORMATION: Xaa is Asp or Glu
<220> FEATURE:
<221> NAME/KEY: VARIANT
<222> LOCATION: (17)..(17)
<223> OTHER INFORMATION: Xaa is Glu, Lys or Ser
<220> FEATURE:
<221> NAME/KEY: VARIANT
<222> LOCATION: (21)..(21)
<223> OTHER INFORMATION: Xaa is Lys, His or Arg
<220> FEATURE:
<221> NAME/KEY: VARIANT
<222> LOCATION: (28)..(28)
<223> OTHER INFORMATION: Xaa is Leu, Glu or Val
<220> FEATURE:
<221> NAME/KEY: VARIANT
<222> LOCATION: (31)..(31)
<223> OTHER INFORMATION: Xaa is Lys, Gly or absent
<220> FEATURE:
<221> NAME/KEY: VARIANT
<222> LOCATION: (32)..(41)
<223> OTHER INFORMATION: Y1, which may be present or absent. If
      present, up to 2 residues may be present or absent, and Y1 is
      SEQ ID NO: 74, SEQ ID NO: 75, SEQ ID NO: 76, or SEQ ID NO: 77.

<400> SEQUENCE: 91

Xaa Tyr Ala Glu Gly Thr Phe Xaa Ser Asp Tyr Ser Ile Xaa Leu Xaa
1               5                   10                  15

Xaa Lys Ala Gln Xaa Ala Phe Val Glu Trp Leu Xaa Ala Gln Xaa Xaa
            20                  25                  30

Xaa Xaa Xaa Xaa Xaa Xaa Xaa Xaa Xaa
            35                  40

<210> SEQ ID NO 92
<211> LENGTH: 31
<212> TYPE: PRT
<213> ORGANISM: Artificial sequence
<220> FEATURE:
<223> OTHER INFORMATION: Synthetic sequence: GIP Analogue
<220> FEATURE:
<221> NAME/KEY: SITE
<222> LOCATION: (1)..(1)
<223> OTHER INFORMATION: Xaa is pGlu
<220> FEATURE:
<221> NAME/KEY: MOD_RES
<222> LOCATION: (30)..(30)
<223> OTHER INFORMATION: Aib

<400> SEQUENCE: 92

Xaa Tyr Ala Glu Gly Thr Phe Thr Ser Asp Tyr Ser Ile Tyr Leu Asp
1               5                   10                  15

Lys Lys Ala Gln Arg Ala Phe Val Asn Trp Leu Leu Ala Ala Lys
            20                  25                  30

<210> SEQ ID NO 93
<211> LENGTH: 29
<212> TYPE: PRT
<213> ORGANISM: Artificial Sequence
<220> FEATURE:
<223> OTHER INFORMATION: Synthetic Construct

<400> SEQUENCE: 93

Tyr Ala Glu Gly Thr Phe Thr Ser Asp Tyr Ser Ile Tyr Leu Glu Lys
1               5                   10                  15

Lys Ala Ala His Asp Phe Val Glu Trp Leu Leu Ser Ala
            20                  25
```

<210> SEQ ID NO 94
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 94

Tyr Xaa Glu Gly Thr Phe Ile Ser Asp Tyr Ser Ile Tyr Leu Glu Lys
1               5                   10                  15

Lys Ala Ala Lys Glu Phe Val Asn Trp Leu Leu Ala Gln Lys
            20                  25                  30

<210> SEQ ID NO 95
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (13)..(13)
<223> OTHER INFORMATION: Xaa is 2-Aminoisobutyric acid (Aib)
<220> FEATURE:
<221> NAME/KEY: SITE
<222> LOCATION: (39)..(39)
<223> OTHER INFORMATION: Linked to R2, wherein R2 is -NH2

<400> SEQUENCE: 95

Tyr Xaa Glu Gly Thr Phe Thr Ser Asp Tyr Ser Ile Xaa Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 96
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)

```
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 96

Tyr Xaa Glu Gly Thr Phe Thr Ser Asp Tyr Ser Ile Ala Leu Asp Lys
1               5                   10                  15

Ile Ala Gln Arg Ala Phe Val Asn Trp Leu Val Ala Xaa Lys
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 97

Tyr Xaa Glu Gly Thr Phe Ile Ser Asp Tyr Ser Ile Tyr Leu Glu Lys
1               5                   10                  15

Ile Ala Ala Lys Glu Phe Val Asn Trp Leu Leu Ala Gln Lys
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 98

Tyr Xaa Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Xaa Lys
            20                  25                  30
```

```
<210> SEQ ID NO 99
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is pGlu
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 99

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Xaa Lys
            20                  25                  30

<210> SEQ ID NO 100
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 100

Tyr Gly Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Xaa Lys
            20                  25                  30

<210> SEQ ID NO 101
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2
```

<400> SEQUENCE: 101

Tyr Xaa Glu Gly Thr Phe Ser Ser Asp Tyr Ser Ile Tyr Leu Asp Lys
1               5                   10                  15

Lys Ala Gln Arg Ala Phe Val Asn Trp Leu Leu Ala Xaa Lys
            20                  25                  30

<210> SEQ ID NO 102
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 102

Tyr Xaa Glu Gly Thr Phe Thr Ser Asp Leu Ser Ile Tyr Leu Asp Lys
1               5                   10                  15

Lys Ala Gln Arg Ala Phe Val Asn Trp Leu Leu Ala Xaa Lys
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 103

Tyr Xaa Glu Gly Thr Phe Thr Ser Asp Tyr Leu Ile Tyr Leu Asp Lys
1               5                   10                  15

Lys Ala Gln Arg Ala Phe Val Asn Trp Leu Leu Ala Xaa Lys
            20                  25                  30

<210> SEQ ID NO 104
<211> LENGTH: 30
<212> TYPE: PRT
<213> ORGANISM: Artificial Sequence
<220> FEATURE:
<223> OTHER INFORMATION: synthetic construct

```
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 104

Tyr Xaa Glu Gly Thr Phe Thr Ser Asp Tyr Ser Ile Ala Leu Asp Lys
1               5                   10                  15

Lys Ala Gln Arg Ala Phe Val Asn Trp Leu Leu Ala Xaa Lys
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 105

Tyr Xaa Glu Gly Thr Phe Thr Ser Asp Tyr Ser Ile Tyr Ser Asp Lys
1               5                   10                  15

Lys Ala Gln Arg Ala Phe Val Asn Trp Leu Leu Ala Xaa Lys
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
```

<223> OTHER INFORMATION: Linked to R2, wherein R2 is -NH2

<400> SEQUENCE: 106

Tyr Xaa Glu Gly Thr Phe Thr Ser Asp Tyr Ser Ile Tyr Leu Glu Lys
1               5                   10                  15

Lys Ala Gln Arg Ala Phe Val Asn Trp Leu Leu Ala Xaa Lys
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 107

Tyr Xaa Glu Gly Thr Phe Thr Ser Asp Tyr Ser Ile Ala Leu Glu Lys
1               5                   10                  15

Lys Ala Gln Arg Ala Phe Val Asn Trp Leu Leu Ala Xaa Lys
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 108

Tyr Xaa Glu Gly Thr Phe Thr Ser Asp Tyr Ser Ile Tyr Leu Asp Ser
1               5                   10                  15

Lys Ala Gln Arg Ala Phe Val Asn Trp Leu Leu Ala Xaa Lys
            20                  25                  30

<210> SEQ ID NO 109
<211> LENGTH: 30
<212> TYPE: PRT
<213> ORGANISM: Artificial Sequence

```
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 109

Tyr Xaa Glu Gly Thr Phe Thr Ser Asp Tyr Ser Ile Tyr Leu Asp Glu
 1               5                  10                  15

Lys Ala Gln Arg Ala Phe Val Asn Trp Leu Leu Ala Xaa Lys
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 110

Tyr Xaa Glu Gly Thr Phe Thr Ser Asp Tyr Ser Ile Tyr Leu Asp Ser
 1               5                  10                  15

Lys Ala Lys Arg Ala Phe Val Asn Trp Leu Leu Ala Xaa Lys
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
```

```
<221> NAME/KEY: SITE
<222> LOCATION: (30)..(30)
<223> OTHER INFORMATION: Linked to R2, wherein R2 is -NH2

<400> SEQUENCE: 111

Tyr Xaa Glu Gly Thr Phe Thr Ser Asp Tyr Ser Ile Tyr Leu Asp Lys
1               5                   10                  15

Lys Ala Gln Lys Glu Phe Val Asn Trp Leu Leu Ala Xaa Lys
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 112

Tyr Xaa Glu Gly Thr Phe Thr Ser Asp Tyr Ser Ile Tyr Leu Asp Lys
1               5                   10                  15

Lys Ala Gln Arg Ala Phe Val Lys Trp Leu Leu Ala Xaa Lys
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: synthetic construct'
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 113

Tyr Xaa Glu Gly Thr Phe Thr Ser Asp Tyr Ser Ile Tyr Leu Asp Lys
1               5                   10                  15

Lys Ala Gln Arg Ala Phe Val Asn Trp Leu Val Ala Xaa Lys
            20                  25                  30

<210> SEQ ID NO 114
<211> LENGTH: 30
```

```
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 114

Tyr Xaa Glu Gly Thr Phe Thr Ser Asp Tyr Ser Ile Tyr Leu Asp Lys
 1               5                  10                  15

Lys Ala Gln Arg Ala Phe Val Asn Trp Leu Lys Ala Xaa Lys
             20                  25                  30

<210> SEQ ID NO 115
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (28)..(28)
<223> OTHER INFORMATION: Xaa is 2-Aminoisobutyric acid (Aib)
<220> FEATURE:
<221> NAME/KEY: SITE
<222> LOCATION: (29)..(29)
<223> OTHER INFORMATION: Linked to R2, wherein R2 is -NH2

<400> SEQUENCE: 115

Tyr Xaa Glu Gly Thr Phe Thr Ser Asp Tyr Ser Ile Tyr Leu Asp Lys
 1               5                  10                  15

Lys Ala Gln Arg Ala Phe Val Asn Trp Leu Leu Xaa Lys
             20                  25

<210> SEQ ID NO 116
<211> LENGTH: 36
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
```

```
<223> OTHER INFORMATION: Xaa is 2-Aminoisobutyric acid (Aib)
<220> FEATURE:
<221> NAME/KEY: MISC_FEATURE
<222> LOCATION: (33)..(33)
<223> OTHER INFORMATION: Xaa is beta-(1-naphthyl)-alanine (1Nal)
<220> FEATURE:
<221> NAME/KEY: SITE
<222> LOCATION: (36)..(36)
<223> OTHER INFORMATION: Linked to R2, wherein R2 is -NH2

<400> SEQUENCE: 116

Tyr Xaa Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Xaa Lys Tyr Gly
            20                  25                  30

Xaa Leu Asp Phe
        35

<210> SEQ ID NO 117
<211> LENGTH: 34
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (31)..(31)
<223> OTHER INFORMATION: Xaa is beta-(1-naphthyl)-alanine (1Nal)
<220> FEATURE:
<221> NAME/KEY: SITE
<222> LOCATION: (34)..(34)
<223> OTHER INFORMATION: Linked to R2, wherein R2 is -NH2

<400> SEQUENCE: 117

Tyr Xaa Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Tyr Gly Xaa Leu
            20                  25                  30

Asp Phe

<210> SEQ ID NO 118
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2
```

<400> SEQUENCE: 118

Tyr Xaa Glu Gly Thr Phe Thr Ser Asp Tyr Ser Ile Tyr Leu Asp Lys
1               5                   10                  15

Lys Ala Glu Lys Ala Phe Val Asn Trp Leu Leu Ala Xaa Lys
            20                  25                  30

<210> SEQ ID NO 119
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (39)..(39)
<223> OTHER INFORMATION: Linked to R2, wherein R2 is -NH2

<400> SEQUENCE: 119

Tyr Xaa Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Xaa Gly Pro Ser
            20                  25                  30

Ser Gly Ala Pro Pro Pro Ser
        35

<210> SEQ ID NO 120
<211> LENGTH: 38
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (38)..(38)
<223> OTHER INFORMATION: Linked to R2, wherein R2 is -NH2

<400> SEQUENCE: 120

Tyr Xaa Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Xaa Gly Pro Ser
            20                  25                  30

Ser Gly Ala Pro Pro Ser
        35

```
<210> SEQ ID NO 121
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 121

Tyr Xaa Glu Gly Thr Phe Thr Ser Asp Tyr Ser Ile Tyr Leu Glu Lys
 1               5                  10                  15

Lys Ala Ala Lys Glu Phe Val Asn Trp Leu Leu Ala Gln Lys
            20                  25                  30

<210> SEQ ID NO 122
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: 15-carboxy-pentadecanoyl-isoGlu
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 122

Tyr Xaa Glu Gly Thr Phe Thr Ser Asp Tyr Ser Ile Tyr Leu Asp Lys
 1               5                  10                  15

Lys Ala Gln Arg Ala Phe Val Asn Trp Leu Leu Ala Xaa Lys
            20                  25                  30

<210> SEQ ID NO 123
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
```

```
<221> NAME/KEY: MISC_FEATURE
<222> LOCATION: (13)..(13)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (39)..(39)
<223> OTHER INFORMATION: Linked to R2, wherein R2 is -NH2

<400> SEQUENCE: 123

Tyr Xaa Glu Gly Thr Phe Thr Ser Asp Tyr Ser Ile Xaa Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 124
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (39)..(39)
<223> OTHER INFORMATION: Linked to R2, wherein R2 is -NH2

<400> SEQUENCE: 124

Tyr Xaa Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 125
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
```

```
<222> LOCATION: (29)..(29)
<223> OTHER INFORMATION: Linked to R2, wherein R2 is -NH2

<400> SEQUENCE: 125

Tyr Xaa Glu Gly Thr Phe Thr Ser Asp Tyr Ser Ile Tyr Leu Asp Glu
1               5                   10                  15

Lys Ala Ala Lys Glu Phe Ile Glu Trp Leu Glu Ser Ala
            20                  25

<210> SEQ ID NO 126
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (39)..(39)
<223> OTHER INFORMATION: Linked to R2, wherein R2 is -NH2

<400> SEQUENCE: 126

Tyr Xaa Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Xaa Lys Pro Ser
            20                  25                  30

Ser Gly Ala Pro Pro Pro Ser
        35

<210> SEQ ID NO 127
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (39)..(39)
<223> OTHER INFORMATION: Linked to R2, wherein R2 is -NH2

<400> SEQUENCE: 127
```

```
Tyr Xaa Glu Gly Thr Phe Thr Ser Asp Tyr Ser Ile Ala Leu Asp Lys
1               5                   10                  15

Lys Ala Gln Arg Ala Phe Val Asn Trp Leu Val Ala Xaa Lys Pro Ser
            20                  25                  30

Ser Gly Ala Pro Pro Ser
        35
```

<210> SEQ ID NO 128
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (29)..(29)
<223> OTHER INFORMATION: Linked to R2, wherein R2 is -NH2

<400> SEQUENCE: 128

```
Tyr Xaa Glu Gly Thr Phe Thr Ser Asp Tyr Ser Ile Tyr Leu Glu Lys
1               5                   10                  15

Lys Ala Ala Lys Asp Phe Val Glu Trp Leu Leu Ser Ala
            20                  25
```

<210> SEQ ID NO 129
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (29)..(29)
<223> OTHER INFORMATION: Linked to R2, wherein R2 is -NH2

<400> SEQUENCE: 129

```
Tyr Xaa Glu Gly Thr Phe Thr Ser Asp Tyr Ser Ile Tyr Leu Glu Lys
1               5                   10                  15

Lys Ala Ala His Asp Phe Val Glu Trp Leu Leu Ser Ala
            20                  25
```

<210> SEQ ID NO 130
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE

```
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (29)..(29)
<223> OTHER INFORMATION: Linked to R2, wherein R2 is -NH2

<400> SEQUENCE: 130

Tyr Xaa Glu Gly Thr Phe Thr Ser Asp Tyr Ser Ile Tyr Leu Glu Lys
1               5                   10                  15

Lys Ala Gln Lys Glu Phe Val Glu Trp Leu Leu Ser Ala
            20                  25

<210> SEQ ID NO 131
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (29)..(29)
<223> OTHER INFORMATION: Linked to R2, wherein R2 is -NH2

<400> SEQUENCE: 131

Tyr Xaa Glu Gly Thr Phe Thr Ser Asp Tyr Ser Ile Tyr Leu Asp Glu
1               5                   10                  15

Lys Ala Ala Lys Asp Phe Val Glu Trp Leu Leu Ser Ala
            20                  25

<210> SEQ ID NO 132
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (29)..(29)
<223> OTHER INFORMATION: Linked to R2, wherein R2 is -NH2

<400> SEQUENCE: 132

Tyr Xaa Glu Gly Thr Phe Thr Ser Asp Tyr Ser Ile Tyr Leu Glu Ser
1               5                   10                  15

Lys Ala Ala His Asp Phe Val Glu Trp Leu Leu Ser Ala
            20                  25

<210> SEQ ID NO 133
<211> LENGTH: 29
<212> TYPE: PRT
<213> ORGANISM: Artificial Sequence
<220> FEATURE:
<223> OTHER INFORMATION: synthetic construct
<220> FEATURE:
```

```
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (29)..(29)
<223> OTHER INFORMATION: Linked to R2, wherein R2 is -NH2

<400> SEQUENCE: 133

Tyr Xaa Glu Gly Thr Phe Thr Ser Asp Tyr Ser Ile Tyr Leu Asp Lys
1               5                   10                  15

Lys Ala Ala His Asp Phe Val Glu Trp Leu Leu Ser Ala
            20                  25

<210> SEQ ID NO 134
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (29)..(29)
<223> OTHER INFORMATION: Linked to R2, wherein R2 is -NH2

<400> SEQUENCE: 134

Tyr Xaa Glu Gly Thr Phe Thr Ser Asp Tyr Ser Ile Tyr Leu Glu Lys
1               5                   10                  15

Lys Ala Ala Lys Glu Phe Val Glu Trp Leu Leu Ser Ala
            20                  25

<210> SEQ ID NO 135
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (29)..(29)
<223> OTHER INFORMATION: Linked to R2, wherein R2 is -NH2

<400> SEQUENCE: 135

Tyr Xaa Glu Gly Thr Phe Thr Ser Asp Tyr Ser Ile Tyr Leu Asp Ser
1               5                   10                  15

Lys Ala Ala His Asp Phe Val Glu Trp Leu Leu Arg Ala
            20                  25

<210> SEQ ID NO 136
<211> LENGTH: 29
```

```
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (29)..(29)
<223> OTHER INFORMATION: Linked to R2, wherein R2 is -NH2

<400> SEQUENCE: 136

Tyr Xaa Glu Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 137
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (29)..(29)
<223> OTHER INFORMATION: Linked to R2, wherein R2 is -NH2

<400> SEQUENCE: 137

Tyr Xaa Glu Gly Thr Phe Thr Ser Asp Tyr Ser Ile Tyr Leu Glu Lys
1               5                   10                  15

Lys Ala Ala Lys Glu Phe Val Glu Trp Leu Leu Ser Ala
            20                  25

<210> SEQ ID NO 138
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
```

```
<223> OTHER INFORMATION: Hexadecanoyl-isoGlu
<220> FEATURE:
<221> NAME/KEY: SITE
<222> LOCATION: (29)..(29)
<223> OTHER INFORMATION: Linked to R2, wherein R2 is -NH2

<400> SEQUENCE: 138

Tyr Xaa Glu Gly Thr Phe Thr Ser Asp Tyr Ser Ile Tyr Leu Asp Ser
1               5                   10                  15

Lys Ala Ala His Asp Phe Val Glu Trp Leu Leu Arg Ala
            20                  25

<210> SEQ ID NO 139
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (29)..(29)
<223> OTHER INFORMATION: Linked to R2, wherein R2 is -NH2

<400> SEQUENCE: 139

Tyr Xaa Glu Gly Thr Phe Thr Ser Asp Tyr Ser Ile Tyr Leu Asp Glu
1               5                   10                  15

Lys Ala Ala Lys Asp Phe Val Glu Trp Leu Glu Ser Ala
            20                  25

<210> SEQ ID NO 140
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (29)..(29)
<223> OTHER INFORMATION: Linked to R2, wherein R2 is -NH2

<400> SEQUENCE: 140

Tyr Xaa Glu Gly Thr Phe Thr Ser Asp Tyr Ser Lys Tyr Leu Asp Glu
1               5                   10                  15

Lys Ala Ala Lys Asp Phe Ile Glu Trp Leu Glu Ser Ala
            20                  25
```

-continued

```
<210> SEQ ID NO 141
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (29)..(29)
<223> OTHER INFORMATION: Linked to R2, wherein R2 is -NH2

<400> SEQUENCE: 141

Tyr Xaa Glu Gly Thr Phe Thr Ser Asp Tyr Ser Ile Tyr Leu Asp Glu
1               5                   10                  15

Lys Ala Ala Lys Asp Phe Ile Glu Trp Leu Glu Ser Ala
            20                  25

<210> SEQ ID NO 142
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (29)..(29)
<223> OTHER INFORMATION: Linked to R2, wherein R2 is -NH2

<400> SEQUENCE: 142

Tyr Xaa Glu Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 143
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
```

```
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (29)..(29)
<223> OTHER INFORMATION: Linked to R2, wherein R2 is -NH2

<400> SEQUENCE: 143

Tyr Xaa Glu Gly Thr Phe Thr Ser Asp Tyr Ser Ile Tyr Leu Asp Glu
1               5                   10                  15

Lys Ala Ala Lys Asp Phe Val Glu Trp Leu Leu Ser Ala
            20                  25

<210> SEQ ID NO 144
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (39)..(39)
<223> OTHER INFORMATION: Linked to R2, wherein R2 is -NH2

<400> SEQUENCE: 144

Tyr Xaa Glu Gly Thr Phe Thr Ser Asp Tyr Ser Ile Tyr Leu Asp Ser
1               5                   10                  15

Lys Ala Ala His Asp Phe Val Glu Trp Leu Leu Ser Ala Gly Pro Ser
            20                  25                  30

Ser Gly Ala Pro Pro Pro Ser
        35

<210> SEQ ID NO 145
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (39)..(39)
<223> OTHER INFORMATION: Linked to R2, wherein R2 is -NH2

<400> SEQUENCE: 145

Tyr Xaa Glu Gly Thr Phe Thr Ser Asp Tyr Ser Ile Tyr Leu Glu Lys
1               5                   10                  15
```

Lys Ala Ala Lys Glu Phe Val Glu Trp Leu Leu Ser Ala Gly Pro Ser
            20                  25                  30

Ser Gly Ala Pro Pro Pro Ser
        35

<210> SEQ ID NO 146
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: SITE
<222> LOCATION: (39)..(39)
<223> OTHER INFORMATION: Linked to R2, wherein R2 is -NH2

<400> SEQUENCE: 146

Tyr Xaa Glu Gly Thr Phe Thr Ser Asp Tyr Ser Ile Tyr Leu Asp Ser
1               5                   10                  15

Lys Ala Ala His Asp Phe Val Glu Trp Leu Leu Ser Ala Gly Pro Ser
            20                  25                  30

Ser Gly Ala Pro Pro Pro Ser
        35

<210> SEQ ID NO 147
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MOD_RES
<222> LOCATION: (17)..(17)
<223> OTHER INFORMATION: Hexadecanoyl-isoGlu
<220> FEATURE:
<221> NAME/KEY: SITE
<222> LOCATION: (29)..(29)
<223> OTHER INFORMATION: Linked to R2, wherein R2 is -NH2

<400> SEQUENCE: 147

Tyr Xaa Glu Gly Thr Phe Thr Ser Asp Tyr Ser Ile Tyr Leu Asp Glu
1               5                   10                  15

Lys Ala Ala His Asp Phe Val Glu Trp Leu Leu Ser Ala
            20                  25

<210> SEQ ID NO 148
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE

```
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 148

Tyr Xaa Glu Gly Thr Phe Thr Ser Asp Ser Ser Ile Tyr Leu Asp Lys
1               5                   10                  15

Lys Ala Gln Arg Ala Phe Val Asn Trp Leu Leu Ala Xaa Lys
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(1)
<223> OTHER INFORMATION: Linked to R1, wherein R1 is Hydrogen (Hy-)
<220> FEATURE:
<221> NAME/KEY: MISC_FEATURE
<222> LOCATION: (2)..(2)
<223> OTHER INFORMATION: Xaa is 2-Aminoisobutyric acid (Aib)
<220> FEATURE:
<221> NAME/KEY: MISC_FEATURE
<222> LOCATION: (29)..(29)
<223> OTHER INFORMATION: Xaa is 2-Aminoisobutyric acid (Aib)
<220> FEATURE:
<221> NAME/KEY: SITE
<222> LOCATION: (30)..(30)
<223> OTHER INFORMATION: Linked to R2, wherein R2 is -NH2

<400> SEQUENCE: 149

Tyr Xaa Glu Gly Thr Phe Thr Ser Asp Tyr Ser Ile Tyr Leu Asp Lys
1               5                   10                  15

Lys Ala Gln Arg Ala Phe Val Asn Trp Leu Ser Ala Xaa Lys
            20                  25                  30
```

GIP-GLP-1 DUAL AGONIST COMPOUNDS AND METHODS

BACKGROUND OF THE INVENTION

Diabetes and obesity are increasing health problems globally and are associated with various other diseases, particularly cardiovascular diseases (CVD), obstructive sleep apnea, stroke, peripheral artery disease, microvascular complications and osteoarthritis. There are 246 million people worldwide with diabetes, and by 2025 it is estimated that 380 million will have diabetes. Many have additional cardiovascular risk factors including high/aberrant LDL and triglycerides and low HDL. Cardiovascular diseases account for about 50% of the mortality in people with diabetes, and the morbidity and mortality rates relating to obesity and diabetes underscore the medical need for efficacious treatment options.

Incretins are gastrointestinal hormones that regulate blood glucose by enhancing glucose-stimulated insulin secretion (Drucker, D J and Nauck, M A, Lancet 368: 1696-705 (2006)). To date there are two known incretins: glucagon-like peptide-1 (GLP-1), and glucose-dependent insulinotropic polypeptide (GIP). The incretin GLP-1 is derived from the pre-proglucagon gene. Pre-proglucagon is a 158-amino acid precursor polypeptide that is processed in different tissues to form a number of different proglucagon-derived peptides, including glucagon, GLP-1, glucagon-like peptide-2 (GLP-2) and oxyntomodulin (OXM). Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GIP is a 42-amino acid peptide derived by proteolytic processing from a 133-amino acid precursor, pre-pro-GIP. All the peptides are involved in a wide variety of physiological functions, including glucose homeostasis, insulin secretion, gastric emptying, and intestinal growth, as well as the regulation of food intake.

The discovery of the incretins has led to the development of two new classes of drugs for the treatment of diabetes mellitus. Thus, injectable GLP-1 receptor agonists, and small molecule compounds (oral DPP-4 inhibitors) that inhibit enzymatic inactivation of both endogenous GLP-1 and GIP, are now on the market (GLP-1 receptor agonists: Byetta™, Bydureon™ and Victoza™ and DPP-4 inhibitors: Januvia™, Galvus™, Onglyza™ and Trajenta™). Apart from the acute effects of GLP-1 and GIP on insulin secretion, the incretins have some long-term effects. Evidence from several laboratories shows that GLP-1 receptor agonists protect pancreatic β-cells by inhibiting apoptosis and enhancing proliferation. For instance, a study by Farilla et al. showed that GLP-1 has anti-apoptotic effects in human islets (Farilla, L, Endocrinology 144: 5149-58 (2003)). Such effects have not been reported for GIP until recently. Weidenmaier et al. reported that a DPP-4 resistant GIP analogue had anti-apoptotic effects (Weidenmaier, S D, PLOS One 5(3): e9590 (2010)). Interestingly, in mouse models of diabetes and obesity, the combination of the GLP-1 receptor agonist Liraglutide and GIP showed superior glucose-lowering and insulinotropic effects compared to treatment with Liraglutide and GIP alone (Gault, V A, Clinical Science 121: 107-117 (2011)).

Chronic treatment with GLP-1 receptor agonists causes significant weight loss in diabetic humans. Interestingly, extended use of DPP-4 inhibitors in similar patients does not consistently change body weight. Evidence suggests (Matthias Tschöp oral presentation at ADA (American Diabetes Association), 2011) that body weight loss associated with GLP-1 agonist treatment is enhanced when GLP-1 and GIP are co-administered. In rodents, co-administration of GLP-1 and GIP results in greater body weight loss than GLP-1 treatment alone. Thus, in addition to improving blood glucose control, GIP may also enhance GLP-1-mediated body weight loss.

SUMMARY OF THE INVENTION

Broadly, the present invention concerns truncated GIP analogues which comprise one or more substitutions as compared to wild-type GIP and which may have the property of an altered, preferably increased GLP-1 activity, e.g., as assessed in in vitro efficacy assays. In the present invention it has been found that GIP-GLP1 dual acting receptor agonists are superior to existing and marketed GLP-1 analogues because the dual agonists offer improved glycemic control, and enhanced body weight loss. The GIP-GLP1 dual agonists (also known as GIP analogues) may thus be used as therapeutics for type 2 diabetes mellitus, obesity and related disorders.

More particularly, preferred GIP analogues of the present invention comprise non-conservative substitutions at one or more of amino acid positions 1, 2, 3, 7, 9, 13, 14, 15, 17, 19, 20, 21, 22, 23, 24, 27, 28, 29, and 30 of the wild-type GIP sequence in combination with Ile, Gln, Lys, Arg or Glu in position 17, optionally in combination with further conservative or non-conservative substitutions at one or more of amino acid positions 10, 11, and 16; and acylation of one or more of amino acid positions 15, 16, 17, 19, 20, 24, 27, 28 and 30 and/or a substitution or deletion of one or more of amino acids corresponding to positions 30 to 42 of the wild-type GIP sequence.

In some embodiments, a GIP analogue of the invention is represented by the general Formula I:

(I)
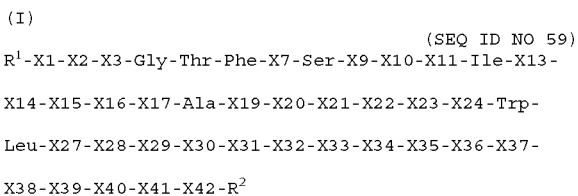

(SEQ ID NO 59)
R¹-X1-X2-X3-Gly-Thr-Phe-X7-Ser-X9-X10-X11-Ile-X13-

X14-X15-X16-X17-Ala-X19-X20-X21-X22-X23-X24-Trp-

Leu-X27-X28-X29-X30-X31-X32-X33-X34-X35-X36-X37-

X38-X39-X40-X41-X42-R² or a pharmaceutically acceptable salt or solvate thereof,
wherein
R¹ is Hy-, Ac or pGlu;
X1 is: His or Tyr;
X2 is Ala, Aib or Gly;
X3 is Glu or Asp;
X7 is Thr, Ser or Ile;
X9 is Asp, Glu;
X10 is Tyr, Leu or Ser;
X11 is Ser or Leu;
X13 is Ala, Tyr or Aib;
X14 is Met, Leu or Ser;
X15 is Asp or Glu;
X16 is Lys, Gly, Ser or Glu;
X17 is Ile, Lys, Gln, Arg or Glu;
X19 is Gln, Ala, Glu or Lys;
X20 is Gln, Lys or Arg;
X21 is Asp, Ala or Glu;
X22 is Phe or 1Nal;
X23 is Val, Ile or Leu;
X24 is Asn, Glu, Arg or Lys;

X27 is Leu, Val, Ile, Lys, Glu or Ser;
X28 is Ala, Ser, Arg or Aib;
X29 is Gln, Aib, Glu, Lys, Gly or Tyr;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
$R^2$ is —NH$_2$ or —OH.

In some embodiments, a GIP analogue of the invention is represented by the general Formula I':

(I')
(SEQ ID NO 61)
R$^1$-Tyr-X2-X3-Gly-Thr-Phe-X7-Ser-X9-X10-X11-X12-

X13-X14-X15-X16-Lys-Ala-X19-X20-X21-X22-X23-X24-

Trp-Leu-X27-X28-X29-X30-X31-X32-X33-X34-X35-X36-

X37-X38-X39-X40-X41-X42-R$^2$ or a pharmaceutically acceptable salt or solvate thereof,
wherein
$R^1$ is Hy-, Ac or pGlu;
X2 is Ala, Aib or Gly;
X3 is Glu or Asp;
X7 is Thr, Ser or Ile;
X9 is Asp or Glu;
X10 is Tyr, Leu or Ser;
X11 is Ser or Leu;
X12 is Ile or Lys;
X13 is Ala, Tyr or Aib;
X14 is Met, Leu or Ser;
X15 is Asp or Glu;
X16 is Lys, Gly, Ser or Glu;
X19 is Gln, Ala, Glu or Lys;
X20 is Gln, Lys, Arg or His;
X21 is Asp, Ala or Glu;
X22 is Phe or 1Nal;
X23 is Val, Ile or Leu;
X24 is Asn, Glu, Arg or Lys;
X27 is Leu, Val, Ile, Lys, Glu or Ser;
X28 is Ala, Ser, Arg or Aib;
X29 is Gln, Aib, Lys, Gly or Ala;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
$R^2$ is —NH$_2$ or —OH.

In other embodiments, a GIP analogue of the invention is represented by the general Formula I(a):

(I(a))
(SEQ ID NO 33)
R$^1$-X1-X2-X3-Gly-Thr-Phe-X7-Ser-X9-X10-X11-Ile-X13-

X14-X15-X16-X17-Ala-X19-X20-X21-X22-X23-X24-Trp-

Leu-X27-X28-X29-X30-X31-X32-X33-X34-X35-X36-X37-

X38-X39-X40-X41-X42-R$^2$ or a pharmaceutically acceptable salt or solvate thereof,
wherein
$R^1$ is Hy-, Ac or pGlu;
X1 is His or Tyr;
X2 is Ala, Aib or Gly;
X3 is Glu or Asp;
X7 is Thr, Ser or Ile;
X9 is Asp or Glu;
X10 is Tyr, Leu or Ser;
X11 is Ser or Leu;
X13 is Ala, Tyr or Aib;
X14 is Met, Leu or Ser;
X15 is Asp or Glu;
X16 is Lys, Gly, Ser or Glu;
X17 is Ile, Lys, Gln, Arg or Glu;
X19 is Gln, Ala, Glu or Lys;
X20 is Gln, Lys or Arg;
X21 is Asp, Ala or Glu;
X22 is Phe or 1Nal;
X23 is Val, Ile or Leu;
X24 is Asn, Glu, Arg or Lys;
X27 is Leu, Val, Ile, Lys, Glu or Ser;
X28 is Ala, Ser, Arg or Aib;
X29 is Gln, Aib, Glu, Lys or Tyr;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
$R^2$ is —NH$_2$ or —OH.

In other embodiments, a GIP analogue of the invention is represented by the general Formula I(a)':

(I(a)')
(SEQ ID NO 62)
R$^1$-Tyr-X2-X3-Gly-Thr-Phe-X7-Ser-X9-X10-X11-X12-

X13-X14-X15-X16-Lys-Ala-X19-X20-X21-X22-X23-X24-

Trp-Leu-X27-X28-X29-X30-X31-X32-X33-X34-X35-X36-

X37-X38-X39-X40-X41-X42-R$^2$ or a pharmaceutically acceptable salt or solvate thereof,
wherein
$R^1$ is Hy-, Ac or pGlu;
X2 is Ala, Aib or Gly;
X3 is Glu or Asp;

X7 is Thr, Ser or Ile;
X9 is Asp or Glu;
X10 is Tyr, Leu or Ser;
X11 is Ser or Leu;
X12 is Ile or Lys;
X13 is Ala, Tyr or Aib;
X14 is Leu or Ser;
X15 is Asp or Glu;
X16 is Lys, Gly, Ser or Glu;
X17 is Ile, Gln, Arg or Glu;
X19 is Gln, Ala, Glu or Lys;
X20 is Gln, Lys, Arg or His;
X21 is Asp, Ala or Glu;
X22 is Phe or 1Nal;
X23 is Val, Ile or Leu;
X24 is Asn, Glu, Arg or Lys;
X27 is Leu, Val, Ile, Lys, Glu or Ser;
X28 is Ala, Ser, Arg or Aib;
X29 is Gln, Aib, Lys, Gly or Ala;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
$R^2$ is —$NH_2$ or —OH.

In other embodiments, a GIP analogue of the invention is represented by the general Formula I(b):

(I(b))
(SEQ ID NO 1)
$R^1$-X1-X2-X3-Gly-Thr-Phe-X7-Ser-X9-X10-X11-Ile-X13-

X14-X15-X16-X17-Ala-X19-X20-X21-X22-X23-X24-Trp-

Leu-X27-X28-X29-X30-X31-X32-X33-X34-X35-X36-X37-

X38-X39-X40-X41-X42-$R^2$ or a pharmaceutically acceptable salt or solvate thereof, wherein
$R^1$ is Hy-, Ac or pGlu;
X1 is His or Tyr;
X2 is Ala, Aib or Gly;
X3 is Glu or Asp;
X7 is Thr or Ser;
X9 is Asp or Glu;
X10 is Tyr, Leu or Ser;
X11 is Ser or Leu;
X13 is Ala, Tyr or Aib;
X14 is Met, Leu or Ser;
X15 is Asp or Glu;
X16 is Lys, Gly, Ser or Glu;
X17 is Ile, Lys, Gln, Arg or Glu;
X19 is Gln, Ala, Glu or Lys;
X20 is Gln, Lys or Arg;
X21 is Asp, Ala or Glu;
X22 is Phe or 1Nal;
X23 is Val, Ile or Leu;
X24 is Asn, Glu, Arg or Lys;
X27 is Leu, Val, Ile, Lys or Ser;

X28 is Ala or Aib;
X29 is Gln, Gly, Aib or Tyr;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
$R^2$ is —$NH_2$ or —OH.

In other embodiments, a GIP analogue of the invention is represented by the general Formula I(b)':

(I(b)')
(SEQ ID NO 63)
$R^1$-Tyr-X2-X3-Gly-Thr-Phe-X7-Ser-X9-X10-X11-X12-

X13-X14-X15-X16-Lys-Ala-X19-X20-X21-Phe-X23-X24-

Trp-Leu-X27-X28-X29-X30-X31-X32-X33-X34-X35-X36-

X37-X38-X39-X40-X41-X42-$R^2$ or a pharmaceutically acceptable salt or solvate thereof, wherein
$R^1$ is Fly-, Ac or pGlu;
X2 is Ala, Aib or Gly;
X3 is Glu or Asp;
X7 is Thr or Ser;
X9 is Asp or Glu;
X10 is Tyr or Leu;
X11 is Ser or Leu;
X12 is Ile or Lys;
X13 is Ala, Tyr or Aib;
X14 is Leu or Ser;
X15 is Asp or Glu;
X16 is Lys, Ser or Glu;
X19 is Gln, Ala, Glu or Lys;
X20 is Gln, Lys, Arg or His;
X21 is Asp, Ala or Glu;
X23 is Val, Ile or Leu;
X24 is Asn, Glu, Arg or Lys;
X27 is Leu, Glu, Val or Ile;
X28 is Ala, Ser, Arg or Aib;
X29 is Gln, Gly, Aib or Ala;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
$R^2$ is —$NH_2$ or —OH.

In some embodiments, a GIP analogue of the invention is represented by the general Formula II:

(II)
(SEQ ID NO 60)
R¹-Tyr-X2-Glu-Gly-Thr-Phe-X7-Ser-Asp-X10-X11-Ile-X13-X14-X15-X16-X17-Ala-X19-X20-X21-Phe-X23-X24-Trp-Leu-X27-X28-X29-X30-Y1-R² wherein
R¹ is Hy-, Ac or pGlu;
X2 is Aib or Gly;
X7 is Thr, Ile or Ser;
X10 is Tyr, Leu or Ser
X11 is Ser or Leu;
X13 is Ala, Tyr or Aib;
X14 is Leu;
X15 is Asp or Glu;
X16 is Ser, Glu or Lys;
X17 is Ile or Lys;
X19 is Gln, Lys, Ala or Glu;
X20 is Lys or Arg;
X21 is Ala or Glu;
X23 is Val or Ile;
X24 is Asn or Glu;
X27 is Leu, Glu, Ser, Lys or Val;
X28 is Aib, Ala, Ser or Arg;
X29 is Aib, Glu, Gly or Lys;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
R² is —NH₂ or —OH.

In some embodiments, a GIP analogue of the invention is represented by the general Formula II':

(II')
(SEQ ID NO 64)
R¹-Tyr-X2-Glu-Gly-Thr-Phe-X7-Ser-Asp-X10-X11-X12-X13-Leu-X15-X16-Lys-Ala-X19-X20-X21-Phe-X23-X24-Trp-Leu-X27-X28-X29-X30-Y1-R² wherein
R¹ is Hy-, Ac or pGlu;
X2 is Aib or Gly;
X7 is Thr, Ile or Ser;
X10 is Tyr or Leu;
X11 is Ser or Leu;
X12 is Ile or Lys;
X13 is Ala, Tyr or Aib;
X15 is Asp or Glu;
X16 is Ser, Glu or Lys;
X19 is Gln or Ala;
X20 is Lys, His or Arg;
X21 is Ala, Asp or Glu;
X23 is Val or Ile;
X24 is Asn, Lys or Glu;
X27 is Leu, Glu, Val or Ile;
X28 is Aib, Ala, Ser or Arg;
X29 is Gln, Aib, Ala, Gly or Lys;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
R² is —NH₂ or —OH.

In other embodiments, a GIP analogue of the invention is represented by the general Formula II(a):

(II(a))
(SEQ ID NO 34)
R¹-Tyr-X2-Glu-Gly-Thr-Phe-X7-Ser-Asp-X10-X11-Ile-X13-X14-X15-X16-X17-Ala-X19-X20-X21-Phe-X23-X24-Trp-Leu-X27-X28-X29-X30-Y1-R² wherein
R¹ is Hy-, Ac or pGlu;
X2 is Aib or Gly;
X7 is Thr, Ile or Ser;
X10 is Tyr, Leu or Ser
X11 is Ser or Leu;
X13 is Ala, Tyr or Aib;
X14 is Leu;
X15 is Asp or Glu;
X16 is Ser, Glu or Lys;
X17 is Ile or Lys;
X19 is Gln, Lys, Ala or Glu;
X20 is Lys or Arg;
X21 is Ala or Glu;
X23 is Val or Ile;
X24 is Asn or Glu;
X27 is Leu, Glu, Ser, Lys or Val;
X28 is Aib, Ala, Ser or Arg;
X29 is Aib, Glu or Lys;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
R² is —NH₂ or —OH.

In other embodiments, a GIP analogue of the invention is represented by the general Formula II(a)':

(II(a)')
(SEQ ID NO 65)
R¹-Tyr-X2-Glu-Gly-Thr-Phe-X7-Ser-Asp-X10-X11-Ile-X13-Leu-X15-X16-Lys-Ala-X19-X20-X21-Phe-X23-X24-Trp-Leu-X27-X28-X29-X30-Y1-R² wherein
R¹ is Hy-, Ac or pGlu;
X2 is Aib or Gly;
X7 is Thr, Ile or Ser;
X10 is Tyr or Leu;
X11 is Ser or Leu;
X13 is Ala, Tyr or Aib;
X15 is Asp or Glu;
X16 is Ser, Glu or Lys;
X19 is Gln, Lys, Ala or Glu;
X20 is Lys, His or Arg;
X21 is Ala, Asp or Glu;
X23 is Val or Ile;
X24 is Asn, Lys or Glu;
X27 is Leu, Glu, Val or Ile;
X28 is Aib, Ala, Ser or Arg;
X29 is Gln, Aib, Ala, or Gly;
X30 is Lys, Gly or absent;

Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

In other embodiments, a GIP analogue of the invention is represented by the general Formula II(b):

(II(b))
(SEQ ID NO 2)
$R^1$-Tyr-Aib-Glu-Gly-Thr-Phe-X7-Ser-Asp-Tyr-Ser-Ile-

X13-X14-X15-Lys-X17-Ala-Gln-X20-X21-Phe-X23-X24-

Trp-Leu-X27-Ala-X29-X30-Y1-$R^2$ or a pharmaceutically acceptable salt or solvate thereof, wherein
$R^1$ is Hy-, Ac or pGlu;
X7 is Thr or Ser;
X13 is Ala, Tyr or Aib;
X14 is Leu;
X15 is Asp or Glu;
X17 is Ile or Lys;
X20 is Lys or Arg;
X21 is Ala or Glu;
X23 is Val or Ile;
X24 is Asn or Glu;
X27 is Leu or Val;
X29 is Aib or Gly;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

In other embodiments, a GIP analogue of the invention is represented by the general Formula II(b)':

(II(b)')
(SEQ ID NO: 66)
$R^1$-Tyr-Aib-Glu-Gly-Thr-Phe-X7-Ser-Asp-Tyr-Ser-

Ile-X13-Leu-X15-X16-Lys-Ala-Gln-X20-X21-Phe-X23-

Glu-Trp-Leu-X27-X28-Ala-X30-Y1-$R^2$ or a pharmaceutically acceptable salt or solvate thereof, wherein
$R^1$ is Hy-, Ac or pGlu;
X7 is Thr or Ser;
X13 is Ala or Tyr;
X15 is Asp or Glu;
X16 is Lys or Ser;
X20 is Lys, His or Arg;
X21 is Ala, Asp or Glu;
X23 is Val or Ile;
X27 is Leu, Glu or Val;
X28 is Arg or Ser;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

In other embodiments, a GIP analogue of the invention is represented by the general Formula II(c):

(II(c))
(SEQ ID NO: 67)
$R^1$-Tyr-Aib-Glu-Gly-Thr-Phe-X7-Ser-Asp-Tyr-Ser-Ile-

X13-Leu-X15-X16-Lys-Ala-Gln-X20-X21-Phe-Val-X24-

Trp-Leu-X27-Ala-X29-X30-Y1-$R^2$ or a pharmaceutically acceptable salt or solvate thereof, wherein
$R^1$ is Hy-, Ac or pGlu;
X7 is Thr or Ser;
X13 is Aib or Tyr;
X15 is Asp or Glu;
X16 is Glu, Lys or Ser;
X20 is Lys, His or Arg;
X21 is Ala, Asp or Glu;
X24 is Glu or Asn;
X27 is Leu, Glu or Val;
X29 is Gln or Aib;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

In other embodiments, a GIP analogue of the invention is represented by the general Formula II(d):

(II(d))
(SEQ ID NO: 68)
$R^1$-Tyr-Aib-Glu-Gly-Thr-Phe-X7-Ser-Asp-Tyr-Ser-Ile-

X13-Leu-X15-X16-Lys-Ala-Gln-X20-Ala-Phe-Val-Glu-

Trp-Leu-X27-Ala-Gln-X30-Y1-$R^2$ or a pharmaceutically acceptable salt or solvate thereof, wherein
$R^1$ is Hy-, Ac or pGlu;
X7 is Thr or Ser;
X13 is Aib or Tyr;
X15 is Asp or Glu;
X16 is Glu, Lys or Ser;
X20 is Lys, His or Arg;
X27 is Leu, Glu or Val;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

Without wishing to be bound by any particular theory, the Isoleucine at position 7 of native GIP appears to provide significant selectivity for the GIP receptor. A small polar residue (e.g. Thr or Ser) at position 7 may increase potency and/or selectivity at the GLP-1 receptor.

Without wishing to be bound by any particular theory, it is believed that substitution of Met found in position 14 of native GIP with a hydrophobic residue like leucine is important for enhancing GLP-1 receptor activity and so increase potency and/or selectivity at the GLP-1 receptor. The substitution of Met at position 14 with leucine also reduces the potential for oxidation, so increasing the chemical stability of the compounds. The non-conservative and non-obvious substitution of Ile for Lys in position 17 may enhance GLP-1 receptor activity and in addition provide a handle for acylation to prolong half life of the peptide.

Without wishing to be bound by any particular theory, the histidine at position 18 of native GIP appears to provide significant selectivity for the GIP receptor. A non-conservative substitution of histidine in position 18 with a small hydrophobic residue (e.g. Ala) may increase potency and/or selectivity at the GLP-1 receptor.

Without wishing to be bound by any particular theory, it is believed that a truncation of the C-terminal of native GIP may be performed without affecting the GIP receptor activity. The truncation can be of any length (1-13 amino acids) down to a 29 amino acid GIP peptide.

Without wishing to be bound by any particular theory, the addition of Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76) or Pro-Ser-Ser-Gly-Ala-Pro-Pro-Ser (SEQ ID NO:77) at or after position 29 or at or after position 30 of a native GIP or a GIP analogue may increase GLP1 receptor activity.

Aib in amino acid position 2 may render GIP peptide having from 42 amino acids down to 29 amino acids resistant to DPP-IV cleavage.

Aib in amino acid position 13 and/or 29 will enhance the stability of the peptide towards enzymatic degradation. In addition, without wishing to be bound by any particular theory, the Aib mayenhance the helicity of the peptide and hence enhance the GLP-1 receptor activity. Furthermore. Nal1 in position 22 may also render the peptide stable to enzymatic degradation.

In a preferred embodiment, the GIP analogue of the invention comprises: Glu at position 24 and/or Ala at position 21, truncated or full length, which may be combined with any of the following:
Thr at position 7, Leu at position 14, truncated or full length;
Thr at position 7, Leu at position 14, Ala at position 18, truncated or full length;
Thr at position 7, Leu at position 14, Lys at position 17, truncated or full length;
Thr at position 7, Leu at position 14, Lys at position 17, Ala at position 18, truncated or full length;
Aib at position 2. Thr at position 7, Leu at position 14. Lys at position 17. Ala at position 18, truncated or full length;
Aib at position 2, Thr at position 7, Leu at position 14, Lys at position 17, Ala at position 18, (Aib at position 13 and/or 29), truncated or full length;
Thr at position 7, Leu at position 14, Ala at position 19, truncated or full length;
Thr at position 7, Leu at position 14, Lys at position 17, Ala at position 19, truncated or full length;
Aib at position 2, Thr at position 7. Leu at position 14, Lys at position 17. Ala at position 18, Ala at position 19, truncated or full length;
Aib at position 2, Thr at position 7, Leu at position 14, Lys at position 17, Ala at position 18, Ala at position 19, (Aib at position 13 and/or 29), truncated or full length;
Thr at position 7, Leu at position 14, Gln at position 19, truncated or full length;
Thr at position 7. Leu at position 14. Lys at position 17, Gln at position 19, truncated or full length;
Aib at position 2, Thr at position 7, Leu at position 14, Lys at position 17, Ala at position 18, Gln at position 19, truncated or full length; or
Aib at position 2, Thr at position 7, Leu at position 14, Lys at position 17, Ala at position 18, Gln at position 19, (Aib at position 13 and/or 29), truncated or full length.
Aib at position 2, Thr at position 7, Leu at position 14, Lys at position 17, Ala at position 18, Ala at position 19, truncated or full length;
Aib at position 2, Thr at position 7, Leu at position 14, Lys at position 17, Ala at position 18, Ala at position 19, Leu at position 27, Ser at position 28 and Ala at position 29, truncated or full length; or
Aib at position 2, Thr at position 7, Leu at position 14, Lys at position 17, Ala at position 18. Ala at position 19. Glu at position 27. Ser at position 28 and Ala at position 29, truncated or full length.

Some embodiments of the invention are:
1. A GIP analogue represented by the general Formula I:

(I)
(SEQ ID NO 59)
$R^1$-X1-X2-X3-Gly-Thr-Phe-X7-Ser-X9-X10-X11-Ile-

X13-X14-X15-X16-X17-Ala-X19-X20-X21-X22-X23-X24-

Trp-Leu-X27-X28-X29-X30-X31-X32-X33-X34-X35-

X36-X37-X38-X39-X40-X41-X42-$R^2$ or a pharmaceutically acceptable salt or solvate thereof, wherein
$R^1$ is Hy-, Ac or pGlu;
X1 is His or Tyr;
X2 is Ala, Aib or Gly;
X3 is Glu or Asp;
X7 is Thr, Ser or Ile;
X9 is Asp or Glu;
X10 is Tyr, Leu or Ser;
X11 is Ser or Leu;
X13 is Ala, Tyr or Aib;
X14 is Met, Leu or Ser;
X15 is Asp or Glu;
X16 is Lys, Gly, Ser or Glu;
X17 is Ile, Lys, Gln, Arg or Glu;
X19 is Gln, Ala, Glu or Lys;
X20 is Gln, Lys or Arg;
X21 is Asp, Ala or Glu;
X22 is Phe or 1Nal;
X23 is Val, Ile or Leu;
X24 is Asn, Glu, Arg or Lys;
X27 is Leu, Val, Ile, Lys, Glu or Ser;
X28 is Ala, Ser, Arg or Aib;
X29 is Gln, Aib, Glu, Lys, Gly or Tyr;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
$R^2$ is —NH$_2$ or —OH.
2. The GIP analogue of embodiment 1, wherein the GIP analogue is represented by the general Formula I(a):

(I(a))
(SEQ ID NO 33)
R¹-X1-X2-X3-Gly-Thr-Phe-X7-Ser-X9-X10-X11-Ile-X13-

X14-X15-X16-X17-Ala-X19-X20-X21-X22-X23-X24-Trp-

Leu-X27-X28-X29-X30-X31-X32-X33-X34-X35-X36-X37-

X38-X39-X40-X41-X42-R² or a pharmaceutically acceptable salt or solvate thereof, wherein
R¹ is Hy-, Ac or pGlu;
X1 is His or Tyr;
X2 is Ala, Aib or Gly;
X3 is Glu or Asp;
X7 is Thr, Ser or Ile;
X9 is Asp or Glu;
X10 is Tyr, Leu or Ser;
X11 is Ser or Leu;
X13 is Ala, Tyr or Aib;
X14 is Met, Leu or Ser;
X15 is Asp or Glu;
X16 is Lys, Gly, Ser or Glu;
X17 is Ile, Lys, Gln, Arg or Glu;
X19 is Gln, Ala, Glu or Lys;
X20 is Gln, Lys or Arg;
X21 is Asp, Ala or Glu;
X22 is Phe or 1Nal;
X23 is Val, Ile or Leu;
X24 is Asn, Glu, Arg or Lys;
X27 is Leu, Val, Ile, Lys, Glu or Ser;
X28 is Ala, Ser, Arg or Aib;
X29 is Gln, Aib, Glu, Lys or Tyr;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
R² is —NH₂ or —OH.

3. The GIP analogue of embodiment 1, wherein the GIP analogue is represented by the general Formula I(b):

(I(b))
(SEQ ID NO 1)
R¹-X1-X2-X3-Gly-Thr-Phe-X7-Ser-X9-X10-X11-Ile-X13-

X14-X15-X16-X17-Ala-X19-X20-X21-X22-X23-X24-Trp-

Leu-X27-X28-X29-X30-X31-X32-X33-X34-X35-X36-X37-

X38-X39-X40-X41-X42-R² or a pharmaceutically acceptable salt or solvate thereof, wherein
R¹ is Hy-, Ac or pGlu;
X1 is His or Tyr;
X2 is Ala, Aib or Gly;
X3 is Glu or Asp;
X7 is Thr or Ser;
X9 is Asp or Glu;
X10 is Tyr, Leu or Ser;
X11 is Ser or Leu;
X13 is Ala, Tyr or Aib;
X14 is Met, Leu or Ser;
X15 is Asp or Glu;
X16 is Lys, Gly, Ser or Glu;
X17 is Ile, Lys, Gln, Arg or Glu;
X19 is Gln, Ala, Glu or Lys;
X20 is Gln, Lys or Arg;
X21 is Asp, Ala or Glu;
X22 is Phe or 1Nal;
X23 is Val, Ile or Leu;
X24 is Asn, Glu, Arg or Lys;
X27 is Leu, Val, Ile, Lys or Ser;
X28 is Ala or Aib;
X29 is Gln, Gly, Aib or Tyr;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
R² is —NH₂ or —OH.

4. A GIP analogue represented by the general Formula II:

(II)
(SEQ ID NO 60)
R¹-Tyr-X2-Glu-Gly-Thr-Phe-X7-Ser-Asp-X10-X11-Ile-

X13-X14-X15-X16-X17-Ala-X19-X20-X21-Phe-X23-X24-

Trp-Leu-X27-X28-X29-X30-Y1-R² wherein
R¹ is Hy-, Ac or pGlu;
X2 is Aib or Gly;
X7 is Thr, Ile or Ser;
X10 is Tyr, Leu or Ser
X11 is Ser or Leu;
X13 is Ala, Tyr or Aib;
X14 is Leu;
X15 is Asp or Glu;
X16 is Ser, Glu or Lys;
X17 is Ile or Lys;
X19 is Gln, Lys, Ala or Glu;
X20 is Lys or Arg;
X21 is Ala or Glu;
X23 is Val or Ile;
X24 is Asn or Glu;
X27 is Leu, Glu, Ser, Lys or Val;
X28 is Aib, Ala, Ser or Arg;
X29 is Aib, Glu, Gly or Lys;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
R² is —NH₂ or —OH.

5. The GIP analogue of embodiment 4, wherein the GIP analogue is represented by the general Formula II(a):

(II(a))
(SEQ ID NO 34)
R¹-Tyr-X2-Glu-Gly-Thr-Phe-X7-Ser-Asp-X10-X11-Ile-

X13-X14-X15-X16-X17-Ala-X19-X20-X21-Phe-X23-X24-

Trp-Leu-X27-X28-X29-X30-Y1-R² wherein
R¹ is Hy-, Ac or pGlu;
X2 is Aib or Gly;
X7 is Thr, Ile or Ser;
X10 is Tyr, Leu or Ser
X11 is Ser or Leu;
X13 is Ala, Tyr or Aib;
X14 is Leu;
X15 is Asp or Glu;
X16 is Ser, Glu or Lys;
X17 is Ile or Lys;
X19 is Gln, Lys, Ala or Glu;
X20 is Lys or Arg;
X21 is Ala or Glu;
X23 is Val or Ile;
X24 is Asn or Glu;
X27 is Leu, Glu, Ser, Lys or Val;
X28 is Aib, Ala, Ser or Arg;
X29 is Aib, Glu or Lys;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
R² is —NH₂ or —OH.

6. The GIP analogue of embodiment 4, wherein the GIP analogue is represented by the general Formula II(b):

(II(b))
(SEQ ID NO 2)
R¹-Tyr-Aib-Glu-Gly-Thr-Phe-X7-Ser-Asp-Tyr-Ser-Ile-

X13-X14-X15-Lys-X17-Ala-Gln-X20-X21-Phe-X23-X24-

Trp-Leu-X27-Ala-X29-X30-Y1-R² or a pharmaceutically acceptable salt or solvate thereof,
wherein
R¹ is Hy-, Ac or pGlu;
X7 is Thr or Ser;
X13 is Ala, Tyr or Aib;
X14 is Leu;
X15 is Asp or Glu;
X17 is Ile or Lys;
X20 is Lys or Arg;
X21 is Ala or Glu;
X23 is Val or Ile;
X24 is Asn or Glu;
X27 is Leu or Val;
X29 is Aib or Gly;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
R² is —NH₂ or —OH.

7. A GIP analogue represented by the general Formula I':

(I')
(SEQ ID NO 61)
R¹-Tyr-X2-X3-Gly-Thr-Phe-X7-Ser-X9-X10-X11-X12-

X13-X14-X15-X16-Lys-Ala-X19-X20-X21-X22-X23-X24-

Trp-Leu-X27-X28-X29-X30-X31-X32-X33-X34-X35-X36-

X37-X38-X39-X40-X41-X42-R² or a pharmaceutically acceptable salt or solvate thereof,
wherein
R¹ is Hy-, Ac or pGlu;
X2 is Ala, Aib or Gly;
X3 is Glu or Asp;
X7 is Thr, Ser or Ile;
X9 is Asp or Glu;
X10 is Tyr, Leu or Ser;
X11 is Ser or Leu;
X12 is Ile or Lys;
X13 is Ala, Tyr or Aib;
X14 is Met, Leu or Ser;
X15 is Asp or Glu;
X16 is Lys, Gly, Ser or Glu;
X19 is Gln, Ala, Glu or Lys;
X20 is Gln, Lys, Arg or His;
X21 is Asp, Ala or Glu;
X22 is Phe or 1Nal;
X23 is Val, Ile or Leu;
X24 is Asn, Glu, Arg or Lys;
X27 is Leu, Val, Ile, Lys, Glu or Ser;
X28 is Ala, Ser, Arg or Aib;
X29 is Gln, Aib, Lys, Gly or Ala;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
R² is —NH₂ or —OH.

8. The GIP analogue of embodiment 7, wherein the GIP analogue is represented by the general Formula I(a)':

(I(a)')
(SEQ ID NO 62)
R¹-Tyr-X2-X3-Gly-Thr-Phe-X7-Ser-X9-X10-X11-X12-

X13-X14-X15-X16-Lys-Ala-X19-X20-X21-X22-X23-X24-

Trp-Leu-X27-X28-X29-X30-X31-X32-X33-X34-X35-X36-

X37-X38-X39-X40-X41-X42-R² or a pharmaceutically acceptable salt or solvate thereof,
wherein
R¹ is Hy-, Ac or pGlu;
X2 is Ala, Aib or Gly;
X3 is Glu or Asp;
X7 is Thr, Ser or Ile;

X9 is Asp or Glu;
X10 is Tyr, Leu or Ser;
X11 is Ser or Leu;
X12 is Ile or Lys;
X13 is Ala, Tyr or Aib;
X14 is Leu or Ser;
X15 is Asp or Glu;
X16 is Lys, Gly, Ser or Glu;
X19 is Gln, Ala, Glu or Lys;
X20 is Gln, Lys, Arg or His;
X21 is Asp, Ala or Glu;
X22 is Phe or 1Nal;
X23 is Val, Ile or Leu;
X24 is Asn, Glu, Arg or Lys;
X27 is Leu, Val, Ile, Lys, Glu or Ser;
X28 is Ala, Ser, Arg or Aib;
X29 is Gln, Aib, Lys, Gly or Ala;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
$R^2$ is —NH$_2$ or —OH.

9. The GIP analogue of embodiment 7, wherein the GIP analogue is represented by the general Formula I(b)':

(I(b)')  (SEQ ID NO 63)
$R^1$-Tyr-X2-X3-Gly-Thr-Phe-X7-Ser-X9-X10-X11-X12-

X13-X14-X15-X16-Lys-Ala-X19-X20-X21-Phe-X23-X24-

Trp-Leu-X27-X28-X29-X30-X31-X32-X33-X34-X35-X36-

X37-X38-X39-X40-X41-X42-$R^2$ or a pharmaceutically acceptable salt or solvate thereof, wherein
$R^1$ is Hy-, Ac or pGlu;
X2 is Ala, Aib or Gly;
X3 is Glu or Asp;
X7 is Thr or Ser;
X9 is Asp or Glu;
X10 is Tyr or Leu;
X11 is Ser or Leu;
X12 is Ile or Lys;
X13 is Ala, Tyr or Aib;
X14 is Leu or Ser;
X15 is Asp or Glu;
X16 is Lys, Ser or Glu;
X19 is Gln, Ala, Glu or Lys;
X20 is Gln, Lys, Arg or His;
X21 is Asp, Ala or Glu;
X23 is Val, Ile or Leu;
X24 is Asn, Glu, Arg or Lys;
X27 is Leu, Glu, Val or Ile;
X28 is Ala, Ser, Arg or Aib;
X29 is Gln, Gly, Aib or Ala;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
$R^2$ is —NH$_2$ or —OH.

10. A GIP analogue represented by the general Formula II':

(II')  (SEQ ID NO 64)
$R^1$-Tyr-X2-Glu-Gly-Thr-Phe-X7-Ser-Asp-X10-X11-X12-

X13-Leu-X15-X16-Lys-Ala-X19-X20-X21-Phe-X23-X24-

Trp-Leu-X27-X28-X29-X30-Y1-$R^2$ wherein
$R^1$ is Hy-, Ac or pGlu;
X2 is Aib or Gly;
X7 is Thr, Ile or Ser;
X10 is Tyr or Leu;
X11 is Ser or Leu;
X12 is Ile or Lys;
X13 is Ala, Tyr or Aib;
X15 is Asp or Glu;
X16 is Ser, Glu or Lys;
X19 is Gln or Ala;
X20 is Lys, His or Arg;
X21 is Ala, Asp or Glu;
X23 is Val or Ile;
X24 is Asn, Lys or Glu;
X27 is Leu, Glu, Val or Ile;
X28 is Aib, Ala, Ser or Arg;
X29 is Gln, Aib, Ala, Gly or Lys;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

11. The GIP analogue of embodiment 10, wherein the GIP analogue is represented by the general Formula II(a)':

(II(a)')  (SEQ ID NO 65)
$R^1$-Tyr-X2-Glu-Gly-Thr-Phe-X7-Ser-Asp-X10-X11-Ile-

X13-Leu-X15-X16-Lys-Ala-X19-X20-X21-Phe-X23-X24-

Trp-Leu-X27-X28-X29-X30-Y1-$R^2$ wherein
$R^1$ is Hy-, Ac or pGlu;
X2 is Aib or Gly;
X7 is Thr, Ile or Ser;
X10 is Tyr or Leu;
X11 is Ser or Leu;
X13 is Ala, Tyr or Aib;
X15 is Asp or Glu;
X16 is Ser, Glu or Lys;
X19 is Gln, Lys, Ala or Glu;

X20 is Lys, His or Arg;
X21 is Ala, Asp or Glu;
X23 is Val or Ile;
X24 is Asn, Lys or Glu;
X27 is Leu, Glu, Val or Ile;
X28 is Aib, Ala, Ser or Arg;
X29 is Gln, Aib, Ala, or Gly;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

12. The GIP analogue of embodiment 10, wherein the GIP analogue is represented by the general Formula II(b)':

(II(b)')
(SEQ ID NO: 66)
$R^1$-Tyr-Aib-Glu-Gly-Thr-Phe-X7-Ser-Asp-Tyr-Ser-Ile-

X13-Leu-X15-X16-Lys-Ala-Gln-X20-X21-Phe-X23-Glu-

Trp-Leu-X27-X28-Ala-X30-Y1-$R^2$ or a pharmaceutically acceptable salt or solvate thereof, wherein
$R^1$ is Hy-, Ac or pGlu;
X7 is Thr or Ser;
X13 is Ala, Tyr or Aib;
X15 is Asp or Glu;
X16 is Lys, Glu or Ser;
X20 is Lys, His or Arg;
X21 is Ala, Asp or Glu;
X23 is Val or Ile;
X27 is Leu, Glu or Val;
X28 is Arg or Ser;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

13. The GIP analogue of embodiment 10, wherein the GIP analogue is represented by the general Formula II(c):

(II(c))
(SEQ ID NO: 67)
$R^1$-Tyr-Aib-Glu-Gly-Thr-Phe-X7-Ser-Asp-Tyr-Ser-Ile-

X13-Leu-X15-X16-Lys-Ala-Gln-X20-X21-Phe-Val-X24-

Trp-Leu-X27-Ala-X29-X30-Y1-$R^2$ or a pharmaceutically acceptable salt or solvate thereof, wherein
$R^1$ is Hy-, Ac or pGlu;
X7 is Thr or Ser;
X13 is Ala, Aib or Tyr;
X15 is Asp or Glu;
X16 is Glu, Lys or Ser;
X20 is Lys, His or Arg;
X21 is Ala, Asp or Glu;
X24 is Glu or Asn;
X27 is Leu, Glu or Val;
X29 is Gln or Aib;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

14. The GIP analogue of embodiment 13, wherein the GIP analogue is represented by the general Formula II(d):

(II(d))
(SEQ ID NO: 68)
$R^1$-Tyr-Aib-Glu-Gly-Thr-Phe-X7-Ser-Asp-Tyr-Ser-Ile-

X13-Leu-X15-X16-Lys-Ala-Gln-X20-Ala-Phe-Val-Glu-

Trp-Leu-X27-Ala-Gln-X30-Y1-$R^2$ or a pharmaceutically acceptable salt or solvate thereof, wherein
$R^1$ is Hy-, Ac or pGlu;
X7 is Thr or Ser;
X13 is Ala, Aib or Tyr;
X15 is Asp or Glu;
X16 is Glu, Lys or Ser;
X20 is Lys, His or Arg;
X27 is Leu, Glu or Val;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —NH$_2$ or —OH.

15. A GIP analogue compound according to any one of embodiments 1 to 14 wherein X24 is Glu and/or X21 is Ala.

16. A GIP analogue compound according to any one of embodiments 1 to 15, wherein X7 is Thr and X14 is Leu.

17. A GIP analogue according to any one of embodiments 1 to 15, wherein X7 is Thr, X14 is Leu and X18 is Ala.

18. A GIP analogue according to any one of embodiments 1 to 15, wherein X7 is Thr, X14 is Leu and X17 is Lys.

19. A GIP analogue according to any one of embodiments 1 to 15, wherein X7 is Thr, X14 is Leu, X17 is Lys and X18 is Ala.

20. A GIP analogue according to any one of embodiments 1 to 15, wherein X2 is Aib, X7 is Thr, X14 is Leu and X17 is Lys.

21. A GIP analogue according to any one of embodiments 1 to 15, wherein X2 is Aib, X7 is Thr, X14 is Leu, X17 is Lys, and X13 and/or X29 is Aib.

22. A GIP analogue according to any one of embodiments 1 to 15, wherein X2 is Aib, X7 is Thr, X14 is Leu, X17 is Lys, X27 is Leu or Glu and X28 is Ser.

23. A GIP analogue according to any one of embodiments 1 to 15, wherein X2 is Aib, X7 is Thr, X14 is Leu, X17 is Lys and X24 is Glu.

24. A GIP analogue according to any one of embodiments 1 to 15, wherein X2 is Aib, X7 is Thr, X14 is Leu, X17 is Lys, X24 is Glu and X29 is Gln.

25. A GIP analogue according to any one of claims 1 to 15, wherein X2 is Aib, X7 is Thr, X14 is Leu, X17 is Lys, X21 is Ala, X24 is Glu and X29 is Gln 26. A GIP analogue according to any one of embodiments 1 to 15, wherein X2 is Aib, X7 is Thr, X14 is Leu, X17 is Lys, X24 is Glu, X27 is Leu and X28 is Ser.

27. A GIP analogue according to any one of embodiments 1 to 15, wherein X2 is Aib, X7 is Thr, X14 is Leu, X17 is Lys, X24 is Glu, X27 is Glu and X28 is Ser.

28. A GIP analogue according to any one of claims 1 to 15, wherein X2 is Aib, X7 is Thr, X14 is Leu, X17 is Lys, X20 is His, X24 is Glu, X27 is Leu and X28 is Ser.

29. A GIP analogue selected from:

(SEQ ID NO: 94)
Hy-Y-Aib-EGTFISDYSIYLEKKAAKEFVNWLLAQK-NH$_2$;

(SEQ ID NO: 95)
Hy-Y-Aib-EGTFTSDYSI-Aib-LDKKAQRAFVEWLLAQGPSSGAPPPS-NH$_2$;

(SEQ ID NO: 96)
Hy-Y-Aib-EGTFTSDYSIALDKIAQRAFVNWLVA-Aib-K-NH$_2$;

(SEQ ID NO: 97)
Hy-Y-Aib-EGTFISDYSIYLEKIAAKEFVNWLLAQK-NH$_2$;

(SEQ ID NO: 98)
Hy-Y-Aib-EGTFTSDYSIYLDKKAQRAFVNWLLA-Aib-K-NH$_2$, (SEQ ID NO: 99)
pGlu-YAEGTFTSDYSIYLDKKAQRAFVNWLLA-Aib-K-NH$_2$;

(SEQ ID NO: 100)
Hy-YGEGTFTSDYSIYLDKKAQRAFVNWLLA-Aib-K-NH$_2$;

(SEQ ID NO: 101)
Hy-Y-Aib-EGTFSSDYSIYLDKKAQRAFVNWLLA-Aib-K-NH$_2$;

(SEQ ID NO: 102)
Hy-Y-Aib-EGTFTSDLSIYLDKKAQRAFVNWLLA-Aib-K-NH$_2$;

(SEQ ID NO: 103)
Hy-Y-Aib-EGTFTSDYLIYLDKKAQRAFVNWLLA-Aib-K-NH$_2$;

(SEQ ID NO: 104)
Hy-Y-Aib-EGTFTSDYSIALDKKAQRAFVNWLLA-Aib-K-NH$_2$;

(SEQ ID NO: 105)
Hy-Y-Aib-EGTFTSDYSIYSDKKAQRAFVNWLLA-Aib-K-NH$_2$;

(SEQ ID NO: 106)
Hy-Y-Aib-EGTFTSDYSIYLEKKAQRAFVNWLLA-Aib-K-NH$_2$;

(SEQ ID NO: 107)
Hy-Y-Aib-EGTFTSDYSIALEKKAQRAFVNWLLA-Aib-K-NH$_2$;

(SEQ ID NO: 108)
Hy-Y-Aib-EGTFTSDYSIYLDSKAQRAFVNWLLA-Aib-K-NH$_2$;

(SEQ ID NO: 109)
Hy-Y-Aib-EGTFTSDYSIYLDEKAQRAFVNWLLA-Aib-K-NH$_2$;

(SEQ ID NO: 110)
Hy-Y-Aib-EGTFTSDYSIYLDSKAKRAFVNWLLA-Aib-K-NH$_2$;

(SEQ ID NO: 111)
Hy-Y-Aib-EGTFTSDYSIYLDKKAQKEFVNWLLA-Aib-K-NH$_2$;

(SEQ ID NO: 112)
Hy-Y-Aib-EGTFTSDYSIYLDKKAQRAFVKWLLA-Aib-K-NH$_2$;

(SEQ ID NO: 113)
Hy-Y-Aib-EGTFTSDYSIYLDKKAQRAFVNWLVA-Aib-K-NH$_2$;

(SEQ ID NO: 114)
Hy-Y-Aib-EGTFTSDYSIYLDKKAQRAFVNWLKA-Aib-K-NH$_2$;

(SEQ ID NO: 115)
Hy-Y-Aib-EGTFTSDYSIYLDKKAQRAFVNWLL-Aib-K-NH$_2$;

(SEQ ID NO: 116)
Hy-Y-Aib-EGTFTSDYSIYLDKKAQRAFVNWLLA-Aib-KYG-1Nal-LDF-NH$_2$;

(SEQ ID NO: 117)
Hy-Y-Aib-EGTFTSDYSIYLDKKAQRAFVNWLLAYG-1Nal-LDF-NH$_2$;

(SEQ ID NO: 118)
Hy-Y-Aib-EGTFTSDYSIYLDKKAEKAFVNWLLA-Aib-K-NH$_2$;

(SEQ ID NO: 119)
Hy-Y-Aib-EGTFTSDYSIYLDKKAQRAFVNWLLA-Aib-GPSSGAPPPS-NH$_2$;

(SEQ ID NO: 120)
Hy-Y-Aib-EGTFTSDYSIYLDKKAQRAFVNWLLA-Aib-GPSSGAPPS-NH$_2$;

(SEQ ID NO: 121)
Hy-Y-Aib-EGTFTSDYSIYLEKKAAKEFVNWLLAQK-NH$_2$;

(SEQ ID NO: 122)
Hy-Y-Aib-EGTFTSDYSIYLDK-K(15-carboxy-pentadecanoyl-isoGlu)-AQRAFVNWLLA-Aib-K-NH$_2$;

(SEQ ID NO: 123)
Hy-Y-Aib-EGTFTSDYSI-Aib-LDK-K(Hexadecanoyl-isoGlu)-AQRAFVEWLLAQGPSSGAPPPS-NH$_2$;

(SEQ ID NO: 124)
Hy-Y-Aib-EGTFTSDYSIYLDK-K(hexadecanoyl-isoGlu)-AQRAFVEWLLAQGPSSGAPPPS-NH$_2$;

(SEQ ID NO: 125)
Hy-Y-Aib-EGTFTSDYSIYLDE-K(hexadecanoyl-isoGlu)-AAKEFIEWLESA-NH$_2$;

(SEQ ID NO: 126)
Hy-Y-Aib-EGTFTSDYSIYLDK-K(hexadecanoyl-isoGlu)-AQRAFVNWLLA-Aib-KPSSGAPPPS-NH$_2$;

(SEQ ID NO: 127)
Hy-Y-Aib-EGTFTSDYSIALDK-K(hexadecanoyl-isoGlu)-AQRAFVNWLVA-Aib-KPSSGAPPPS-NH$_2$;

(SEQ ID NO: 128)
Hy-Y-Aib-EGTFTSDYSIYLE-KKAAKDFVEWLLSA-NH$_2$;

(SEQ ID NO: 129)
Hy-Y-Aib-EGTFTSDYSIYLE-KKAAHDFVEWLLSA-NH$_2$;

(SEQ ID NO: 130)
Hy-Y-Aib-EGTFTSDYSIYLEKKAQKEFVEWLLSA-NH$_2$;

(SEQ ID NO: 131)
Hy-Y-Aib-EGTFTSDYSIYLDEKAAKDFVEWLLSA-NH$_2$;

(SEQ ID NO: 132)
Hy-Y-Aib-EGTFTSDYSIYLESKAAHDFVEWLLSA-NH$_2$;

(SEQ ID NO: 133)
Hy-Y-Aib-EGTFTSDYSIYLDKKAAHDFVEWLLSA-NH$_2$;

(SEQ ID NO: 134)
Hy-Y-Aib-EGTFTSDYSIYLEKKAAKEFVEWLLSA-NH$_2$;

(SEQ ID NO: 135)
Hy-Y-Aib-EGTFTSDYSIYLDSKAAHDFVEWLLRA-NH$_2$;

(SEQ ID NO: 136)
Hy-Y-Aib-EGTFTSDYSKYLDS-K(Hexadecanoyl-isoGlu)-AAHDFVEWLLSA-NH$_2$;

(SEQ ID NO: 137)
Hy-Y-Aib-EGTFTSDYSIYLEK-K(Hexadecanoyl-isoGlu)-AAKEFVEWLLSA-NH$_2$;

(SEQ ID NO: 138)
Hy-Y-Aib-EGTFTSDYSIYLDS-K(Hexadecanoyl-isoGlu)-AAHDFVEWLLRA-NH$_2$;

(SEQ ID NO: 139)
Hy-Y-Aib-EGTFTSDYSIYLDE-K(Hexadecanoyl-isoGlu)-AAKDFVEWLESA-NH$_2$;

(SEQ ID NO: 140)
Hy-Y-Aib-EGTFTSDYSKYLDE-K(Hexadecanoyl-isoGlu)-
AAKDFIEWLESA-NH₂;

(SEQ ID NO: 141)
Hy-Y-Aib-EGTFTSDYSIYLDE-K(Hexadecanoyl-isoGlu)-
AAKDFIEWLESA-NH₂;

(SEQ ID NO: 142)
Hy-Y-Aib-EGTFTSDYSKYLDS-K(Hexadecanoyl-isoGlu)-
AAHDFVEWLLRA-NH₂;

(SEQ ID NO: 143)
Hy-Y-Aib-EGTFTSDYSIYLDE-K(Hexadecanoyl-isoGlu)-
AAKDFVEWLLSA-NH₂;

(SEQ ID NO: 144)
Hy-Y-Aib-EGTFTSDYSIYLDS-K(Hexadecanoyl-isoGlu)-
AANDFVEWLLSAGPSSGAPPPS-NH₂;

(SEQ ID NO: 145)
Hy-Y-Aib-EGTFTSDYSIYLEK-K-(Hexadecanoyl-isoGlu)-
AAKEFVEWLLSAGPSSGAPPPS-NH₂;

(SEQ ID NO: 146)
Hy-Y-Aib-EGTFTSDYSIYLDSKAAHDFVEWLLSAGPSSGAPPPS-
NH₂;
and (SEQ ID NO: 147)
Hy-Y-Aib-EGTFTSDYSIYLDE-K(Hexadecanoyl-isoGlu)-
AAHDFVEWLLSA-NH₂;

or a pharmaceutically acceptable salt or solvate thereof.
30. A GIP analogue according to any one of the preceding embodiments with a lipophilic substituent conjugated to one or more of positions 15, 16, 17, 19, 20, 24, 27, 28 and 30.
31. A GIP analogue according to any one of the preceding embodiments for use in a therapeutic method.
32. A pharmaceutical composition comprising a GIP analogue of any one of the preceding embodiments, or a salt, solvate or derivative thereof, in admixture with a carrier.
33. The pharmaceutical composition of embodiment 32, wherein the GIP analogue is a pharmaceutically acceptable acid addition salt.
34. The pharmaceutical composition of embodiment 32 or embodiment 33, which is formulated as a liquid suitable for administration by injection or infusion, or which is formulated to cause slow release of said GIP analogue.
35. Use of a GIP analogue of any one of embodiments 1 to 30 for the preparation of a medicament for the treatment and/or prevention of metabolic diseases.
36. Use of a GIP analogue of any one of embodiments 1 to 30 for the preparation of a medicament for the treatment and/or prevention of diabetes or a diabetes related disorder.
37. Use of a GIP analogue of any one of embodiments 1 to 30 for the preparation of a medicament for the treatment and/or prevention of obesity or an obesity related disorder.
38. The use of embodiment 37, wherein the diabetes related disorder is selected from insulin resistance, glucose intolerance, increased fasting glucose, pre-diabetes, type 1 diabetes, type 2 diabetes, gestational diabetes hypertension, dyslipidemia, or a combination thereof.
39. The use of embodiment 37, wherein the diabetes related disorder is selected from atherosclerosis, arteriosclerosis, coronary heart disease, peripheral artery disease and stroke; or is associated with a condition selected from atherogenic dyslipidemia, blood fat disorders, elevated blood pressure, hypertension, a prothrombotic state, and proinflammatory state, or a combination thereof.
40. The use of embodiment 39, wherein the blood fat disorder is selected from high triglycerides, low HDL cholesterol, high LDL cholesterol, and plaque buildup in artery walls, or a combination thereof.
41. The use of embodiment 39, wherein the prothrombotic state is selected from high fibrinogen levels in the blood and high plasminogen activator inhibitor-1 levels in the blood.
42. The use of embodiment 39, wherein the proinflammatory state is an elevated C-reactive protein level in the blood.
43. The use of embodiment 37, wherein the obesity related disorder is selected from obesity linked inflammation, obesity linked gallbladder disease and obesity induced sleep apnea, or is associated with a condition selected from atherogenic dyslipidemia, blood fat disorders, elevated blood pressure, hypertension, a prothrombotic state, and a proinflammatory state, or a combination thereof.
44. A nucleic acid molecule comprising a nucleic acid sequence encoding a GIP analogue of any one of embodiments 1 to 30.
45. An expression vector comprising the nucleic acid sequence of embodiment 44, in combination with control sequences to direct its expression.
46. A host cell transformed with the expression vector of embodiment 45.
47. A method of producing the GIP analogue of any one of embodiments 1 to 30, the method comprising culturing the host cells of embodiment 46 under conditions suitable for expressing the GIP analogue and purifying the GIP analogue thus produced.
48. A nucleic acid molecule according to embodiment 44, an expression vector according to embodiment 45, or a host cell according to embodiment 46 for use in therapy.
49. Use of a nucleic acid molecule according to embodiment 44, an expression vector according to embodiment 45 or a host cell according to embodiment 46, in the preparation of a medicament for the treatment and/or prevention of a metabolic disorder.
50. The use of embodiment 49, wherein the metabolic disorder is selected from diabetes and obesity.
51. A method of treating a stomach and/or bowel-related disorder in a patient in need thereof by administering an effective amount a GIP analogue of any one of embodiments 1 to 30, a nucleic acid molecule according to embodiment 44, an expression vector according to embodiment 45, or a host cell according to embodiment 46.
52. A method of treatment and/or prevention of a metabolic disease or disorder in a patient in need thereof comprising administering to said patient an effective amount of the GIP analogue of any one of embodiments 1 to 30, a nucleic acid molecule according to embodiment 44, an expression vector according to embodiment 45, or a host cell according to embodiment 46.
53. The method of embodiment 52, wherein the metabolic disease or disorder is selected from diabetes and obesity.
54. A method of treatment and/or prevention of a diabetes related disorder in a patient in need thereof comprising the step of administering to said patient an effective amount of the GIP analogue of any one of embodiments 1 to 30, a nucleic acid molecule according to embodiment 44, an expression vector according to embodiment 45, or a host cell according to embodiment 46.
55. A method of treatment and/or prevention of an obesity related disorder in a patient in need thereof comprising the step of administering to said patient an effective amount of the GIP analogue of any one of embodiments 1 to 30, a nucleic acid molecule according to embodiment 44, an expression vector according to embodiment 45, or a host cell according to embodiment 46.

56. The method of embodiment 54, wherein the diabetes related disorder is selected from insulin resistance, glucose intolerance, increased fasting glucose, pre-diabetes, type 1 diabetes, type 2 diabetes, gestational diabetes hypertension, dyslipidemia, or a combination thereof.

57. The method of embodiment 54, wherein the diabetes related disorder is selected from atherosclerosis, arteriosclerosis, coronary heart disease, peripheral artery disease and stroke; or is associated with a condition selected from atherogenic dyslipidemia, blood fat disorders, elevated blood pressure, hypertension, a prothrombotic state, and a proinflammatory state, or a combination thereof.

58. The method of embodiment 57, wherein the blood fat disorder is selected from high triglyceride level, low HDL cholesterol level, high LDL cholesterol level, plaque buildup in artery walls, or a combination thereof.

59. The method of embodiment 57, wherein the prothrombotic state is selected from high fibrinogen levels in the blood and high plasminogen activator inhibitor-1 levels in the blood.

60. The method of embodiment 57, wherein the proinflammatory state is an elevated C-reactive protein level in the blood.

61. The method of embodiment 55, wherein the obesity related disorder is selected from obesity linked inflammation, obesity linked gallbladder disease and obesity induced sleep apnea.

62. A therapeutic kit comprising a GIP analogue according to any one of embodiments 1 to 30, a nucleic acid molecule according to embodiment 44, an expression vector according to embodiment 45, or a host cell according to embodiment 46, each optionally in combination with a pharmaceutically acceptable carrier.

63. A device comprising a GIP analogue according to any one of embodiments 1 to 30, a nucleic acid molecule according to embodiment 44, an expression vector according to embodiment 45, or a host cell according to embodiment 46, for delivery of the GIP analogue to a subject.

64. A pharmaceutical composition comprising the GIP analogue of any one of embodiments 1 to 30 for use in treating a stomach and bowel-related disorder in a patient in need thereof.

65. A pharmaceutical composition comprising the GIP analogue of any one of embodiments 1 to 30 for use in treatment and/or prevention of a metabolic disease or disorder in a patient in need thereof.

66. The pharmaceutical composition of embodiment 65, wherein the metabolic disorder is selected from diabetes and obesity.

67. A pharmaceutical composition comprising the GIP analogue of any one of embodiments 1 to 30 for use in treatment and/or prevention of a diabetes related disorder in a patient in need thereof.

68. A pharmaceutical composition comprising the GIP analogue of any one of embodiments 1 to 30 for use in treatment and/or prevention of an obesity related disorder in a patient in need thereof.

69. The pharmaceutical composition of embodiment 67, wherein the diabetes related disorder is selected from insulin resistance, glucose intolerance, increased fasting glucose, pre-diabetes, type 1 diabetes, type 2 diabetes, gestational diabetes hypertension and dyslipidemia, or a combination thereof.

70. The pharmaceutical composition of embodiment 67, wherein the diabetes related disorder is selected from atherosclerosis, arteriosclerosis, coronary heart disease, peripheral artery disease and stroke; or is associated with a condition selected from atherogenic dyslipidemia, blood fat disorders, elevated blood pressure, hypertension, a prothrombotic state, and a proinflammatory state, or a combination thereof.

71. The pharmaceutical composition of embodiment 70, wherein the blood fat disorder is selected from high triglyceride level, low HDL cholesterol level, high LDL cholesterol level, plaque buildup in artery walls, or a combination thereof.

72. The pharmaceutical composition of embodiment 70, wherein the prothrombotic state is selected from high fibrinogen levels in the blood, and high plasminogen activator inhibitor-1 levels in the blood.

73. The pharmaceutical composition of embodiment 70, wherein the proinflammatory state is an elevated C-reactive protein level in the blood.

74. The pharmaceutical composition of embodiment 68, wherein the obesity related disorder is selected from obesity linked inflammation, obesity linked gallbladder disease, and obesity induced sleep apnea.

In Formulae I, Ia, Ib, I', Ia' and Ib', residues X30 to X42 may be present or absent. They are not present or absent independently of one another. If any one of these residues is absent, then all residues C-terminus of that residue are also absent. Thus, the only combinations of residues which can be absent are X42; X41-X42; X40-X41-X42; X39-X40-X41-X42; X38-X39-X40-X41-X42; X37-X38-X39-X40-X41-X42; X36-X37-X38-X39-X40-X41-X42; X35-X36-X37-X38-X39-X40-X41-X42; X34-X35-X36-X37-X38-X39-X40-X41-X42; X33-X34-X35-X36-X37-X38-X39-X40-X41-X42; X32-X33-X34-X35-X36-X37-X38-X39-X40-X41-X42; X31-X32-X33-X34-X35-X36-X37-X38-X39-X40-X41-X42; X30-X31-X32-X33-X34-X35-X36-X37-X38-X39-X40-X41-X42. To put it another way, if residue XN is present (where N is an integer between 30 and 42) then residue X(N−1) is also present.

For all of the embodiments described above, it may be desirable that the amino acid sequence X1-X29 has no more than 6 amino acid differences from the sequence Y-Aib-EGTFTSDYSIYLDKKAQRAFVEWLLAQ (SEQ ID NO: 70). The amino acid sequence X1-X29 may, for example, have no more than 5, 4, 3, 2 or 1 amino acid differences from that sequence.

For all of the embodiments described above, it may be desirable that the amino acid sequence X1-X29 has no more than 6 amino acid differences from the sequence Y-Aib-EGTFTSDYSIYLEKKEFVEWLLSA (SEQ ID NO: 71). The amino acid sequence X1-X29 may, for example, have no more than 5, 4, 3, 2 or 1 amino acid differences from that sequence.

For all of the embodiments described above, it may be desirable that the amino acid sequence X1-X29 has no more than 5 amino acid differences from the sequence Y-Aib-EGTFTSDYSIYLDEKEFIEWLESA (SEQ ID NO: 72). The amino acid sequence X1-X29 may, for example, have no more than 4, 3, 2 or 1 amino acid differences from that sequence.

BRIEF DESCRIPTION OF THE DRAWINGS

FIG. 2: Body weight during the 21-days treatment period (A) and absolute body weight changes (delta Δ=body weight at day 21−body weight at day 0) (B). Data are means±SEM; n=7-10.

FIG. 3: Percent body fat mass (delta Δ=fat mass at day 19−fat mass before treatment) (A) and percent body lean mass (delta Δ=lean mass at day 19−lean mass before treatment) (B) on day 19. Data are means±SEM; n=7-10.

FIG. 5: Blood glucose (A) and plasma insulin (B) on day 13. The blood samples were taken from 4-hour fasted mice. The mice were not dosed in the morning prior to the blood sampling. Data are means±SEM; n=7-10.

FIG. 6: Blood glucose (A) and plasma insulin (B) on day 21. The mice were injected with vehicle, liraglutide or test substance 2 hours prior to the blood sampling. Data are means±SEM; n=7-10.

DETAILED DESCRIPTION OF THE INVENTION

Figure 1:
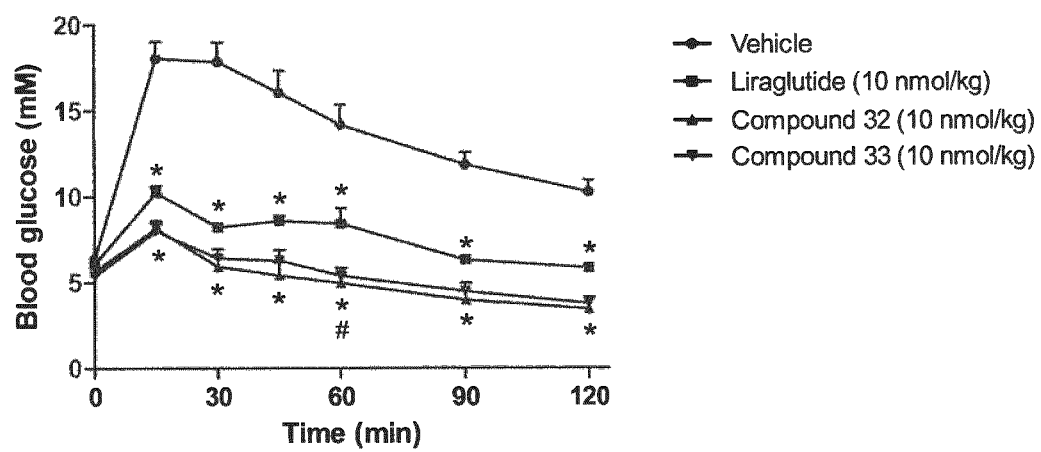
FIG. 1: Effect of Compounds 32 and 33 on glucose tolerance. Compound 32, Compound 33 and liraglutide significantly improved glucose tolerance as compared to vehicle at all time points ($p<0.05$). At time t=60 min, Compound 33 caused a statistically significant greater reduction ($p<0.05$) in blood glucose than liraglutide. *, $p<0.05$ vs. vehicle; #, $p<0.05$ vs. liraglutide. Two-way ANOVA followed by Bonferroni post-tests were used for the statistical analysis. Data are mean±SEM; n=2-6.
Figure 4:
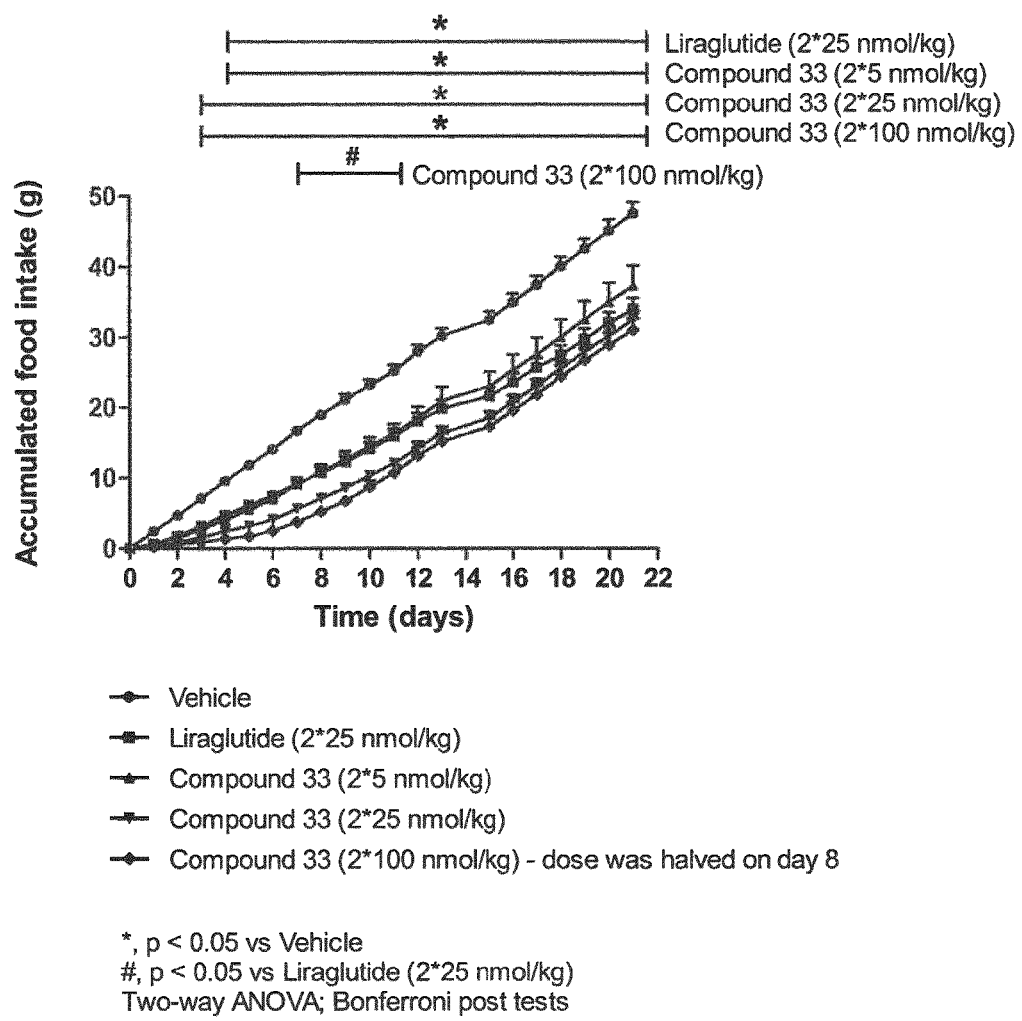
FIG. 4: Accumulated food intake. Food intake was not measured on day 14. Data are means±SEM; n=7-10.
Figure 7:
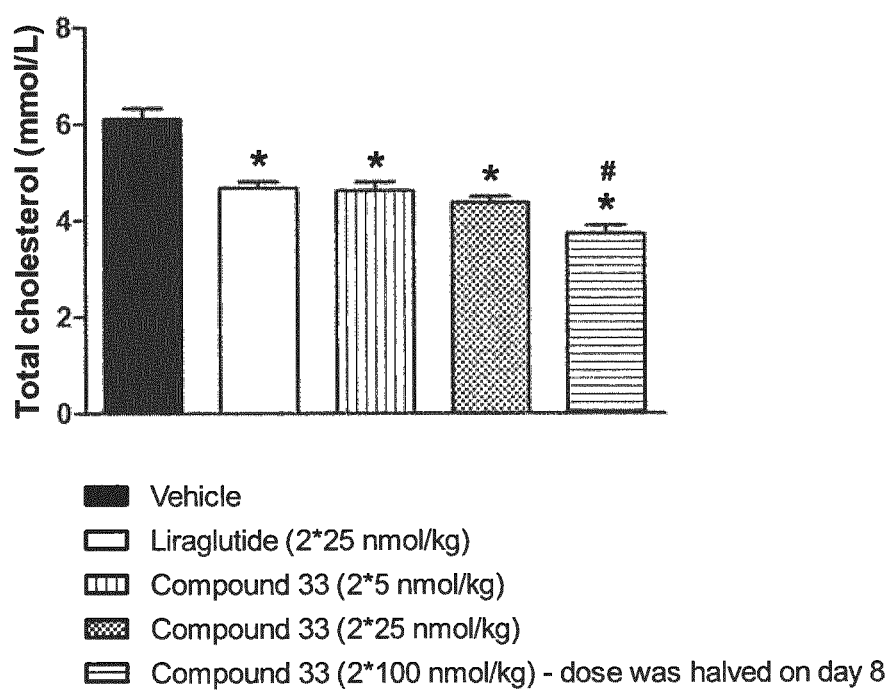
FIG. 7: Plasma total cholesterol (A), plasma LDL cholesterol (B), plasma HDL cholesterol (C), and plasma triglycerides (D) on day 21. Data are means±SEM; n=7-10.
Figure 7:
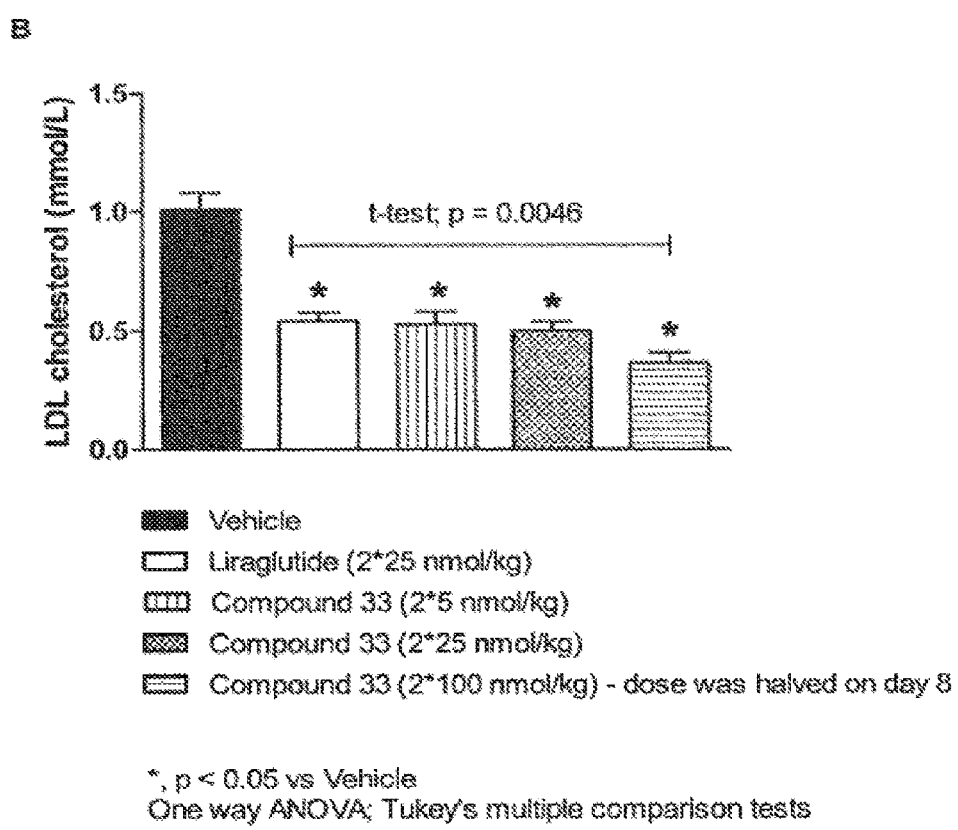
Figure 7:
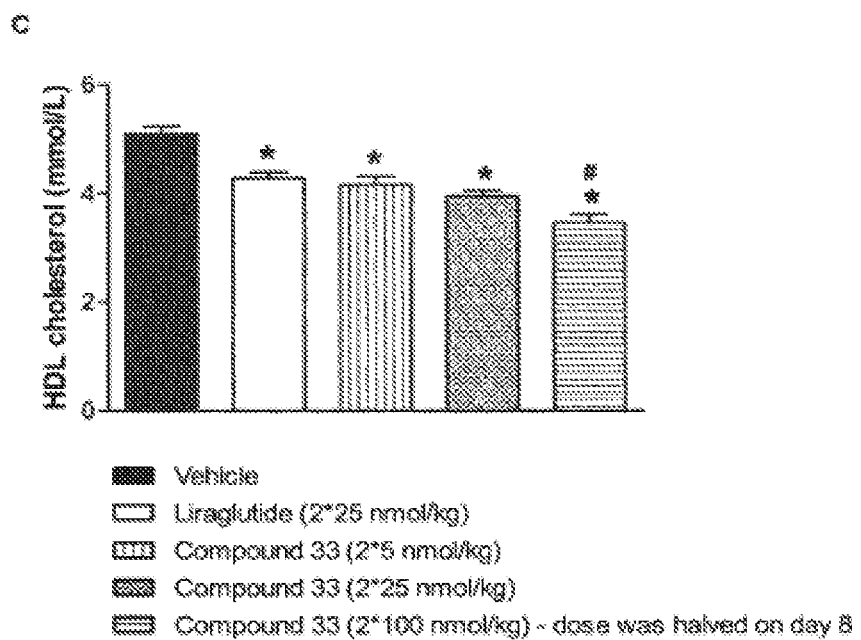
Figure 7:
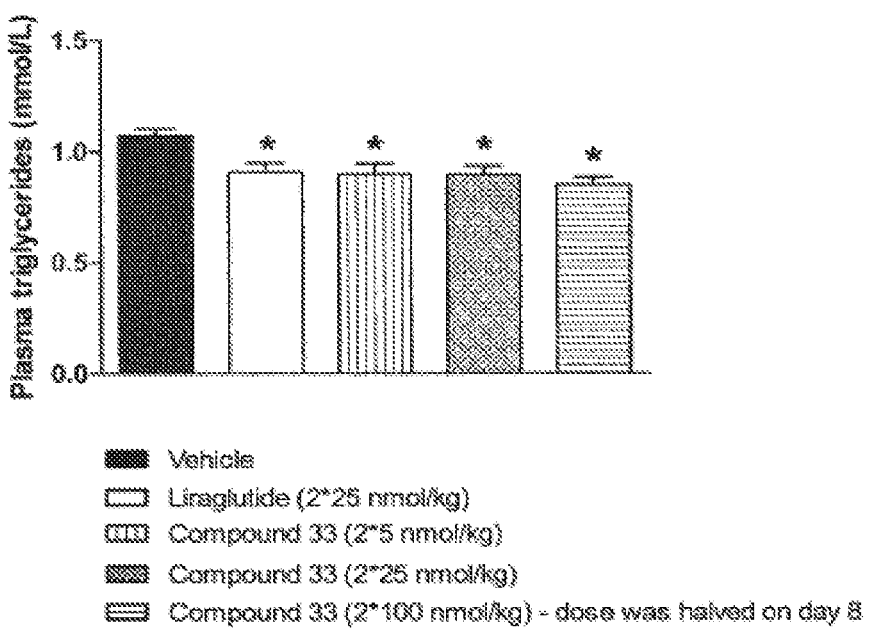

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

All publications, patents and published patent applications referred to in this application are specifically incorporated by reference herein. In case of conflict, the present specification, including its specific definitions, will control.

Each embodiment of the invention described herein may be taken alone or in combination with one or more other embodiments of the invention.

DEFINITIONS

Unless specified otherwise, the following definitions are provided for specific terms, which are used in the above written description.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "solvate" in the context of the present invention refers to a complex of defined stoichiometry formed between a solute (in casu, a peptide conjugate or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

The term "agonist" as employed in the context of the invention refers to a substance (ligand) that activates the receptor type in question.

Throughout the description and claims the conventional one-letter and three-letter codes for natural amino acids are used as well as generally accepted three letter codes for other α-amino acids, such as sarcosine (Sar), norleucine (Nle), α-aminoisobutyric acid (Aib) and β-(1-naphthyl)-alanine (1Nal). All amino acid residues in peptides of the invention are preferably of the L-configuration. However, D-configuration amino acids may also be present.

Among sequences disclosed herein are sequences incorporating an "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, an "Hy-" moiety at the N-terminus of the sequence in question indicates a hydrogen atom [e.g., $R^1$=Hy- in formulas I I(a), I(b), II, II(a) or II(b); corresponding to the presence of a free primary or secondary amino group at the N-terminus], while an "—OH" or an "—NH$_2$" moiety at the C-terminus of the sequence indicates a hydroxy group [e.g., $R^2$=OH in formulas I I(a), I(b), II, II(a) or II(b); corresponding to the presence of a carboxy (COOH) group at the C-terminus] or an amino group [e.g., $R^2$=NH$_2$ in formulas I I(a), I(b), II, II(a) or II(b); corresponding to the presence of an amido (CONH$_2$) group at the C-terminus], respectively. In each sequence of the invention, a C-terminal "—OH" moiety may be substituted for a C-terminal "—NH$_2$" moiety, and vice-versa.

As used herein "conservative substitution" means that an amino acid residue belonging to a certain position of the native human GIP peptide sequence has been exchanged with an amino acid residue belonging to the same group (I, II, III, IV, V, 1, 2, 3) as defined in the following table:

| I | II | III | IV | V |
|---|----|-----|----|----|
| A | N | H | M | F |
| S | D | R | L | Y |
| T | E | K | I | W |
| P | Q |   | V |   |
| G |   |   | C |   |

In the scheme below, conservative substitutions of amino acids are grouped by physicochemical properties. I: neutral or hydrophobic, II: acidic, III: basic, IV: polar, V: aromatic.

| I | II | III | IV | V |
|---|----|-----|----|----|
| A | E | H | M | F |
| L | D | R | S | Y |
| I |   | K | T | W |
| P |   |   | C |   |
| G |   |   | N |   |
| V |   |   | Q |   |

A "non-conservative" substitution as used herein means any other substitution of an amino acid residue of the native human GIP sequence, e.g. such as substituting with a non-protein amino acid (Sar, Nle, Aib, 1Nal) or substituting with an amino acid which does not belong to the same group. In some embodiments, the peptide conjugate of the invention may comprise functional fragments or variants thereof that have at most 34, 33, 32, 31 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid substitutions compared to one or more of the specific sequences recited below.

Preferred compounds of the present invention have at least one GIP and one GLP-1 biological activity, in particular in treatment of metabolic diseases such as diabetes and obesity. This can be assessed, e.g., in in vivo assays, for example as described in the examples, in which the blood glucose level or another biological activity is determined after a test animal has been treated or exposed to a GIP analogue. In particular, compounds of the invention may be capable of improving glycaemic control when adminstered to a diabetic subject. Additionally or alternatively, they may be capable of reducing body weight when administered to an overweight or obese subject. In either case, the effect may be superior to that obtained with an equivalent quantity (by mass, or molar ratio) of wild type human GIP or GLP-1 in comparable subjects when given according to a comparable dosing regime.

Activity in in vitro assays may also be used as a measure of the compounds' activity. Typically the compounds have activity at both the GLP-1 and GIP receptors. $EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$ [GLP-1R] lower than the $EC_{50}$ [GLP-1R] of native glucagon in a particular assay may be considered to have higher potency at the GLP-1R than glucagon. In some embodiments of the present invention, the $EC_{50}$ GLP-1-R and/or $EC_{50}$ GIP-R is below 1.0 nM, below 0.9 nM, below 0.8 nM, below 0.7 nM, below 0.6 nM, below 0.5 nM, below 0.4 nM, below 0.3 nM, below 0.2 nM, below 0.1 nM, below 0.09 nM, below 0.08 nM, below 0.07 nM, below 0.06 nM, below 0.05 nM, below 0.04 nM, below 0.03 nM, below 0.02 nM, below 0.01 nM, below 0.009 nM, below 0.008 nM, below 0.007 nM, below 0.006 nM, or below 0.005 nM, e.g. when assessed using the assay described in Example 2. In any given assay, the $EC_{50}$ value of a compound in a given assay may be assessed relative to the $EC_{50}$ of human GIP. Thus, the ratio of the $EC_{50}$ value of the test compound to the $EC_{50}$ value of wild type human GIP ($EC_{50}$[test compound]/$EC_{50}$[GIP]) at the human GIP receptor may be less than 10, less than 5, less than 1, less than 0.1, less than 0.05 or less than 0.01. The ratio of the $EC_{50}$ value of the test compound to the $EC_{50}$ value of wild type human GIP ($EC_{50}$[test compound]/$EC_{50}$[GIP]) at the GLP-1 receptor may be less than 10, less than 5, less than 1, less than 0.1, less than 0.05 or less than 0.01. It may also be desirable to compare the ratio of $EC_{50}$ values at the two receptors for the test compound and for human GIP. Preferably the test compound has an $EC_{50}$[GIP]/$EC_{50}$[GLP-1] which is greater than the equivalent ratio for GIP in the same assays.

The GIP analogue compounds of the present invention have one or more amino acid substitutions, deletions, inversions, or additions compared with native GIP and as defined above. This definition also includes the synonym terms GIP mimetics and/or GIP-GLP1 agonists. Further, the analogue of the present invention may additionally have chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Preferably herein lower alkyl is $C_1$-$C_4$ alkyl. Furthermore, one or more side groups, or terminal groups, may be protected by protective groups known to the ordinarily-skilled peptide chemist. The α-carbon of an amino acid may be mono- or di-methylated.

Exemplary GIP analogue compounds of the present invention (formulae I, II, III or IV) are described below, where said compounds may be modified at the N-terminus and C-terminus as described for R1 and R2, and include a pharmaceutically acceptable salt, solvate or derivative thereof:

```
                                                     SEQ ID NO. 3
Y-Aib-EGTFISDYSIYLEKKAAKEFVNWLLAQK

SEQ ID NO. 4
Y-Aib-EGTFTSDYSI-Aib-LDKKAQRAFVEWLLAQGPSSGAPPPS

SEQ ID NO. 5
Y-Aib-EGTFTSDYSIALDKIAQRAFVNWLVA-Aib-K

SEQ ID NO. 6
Y-Aib-EGTFISDYSIYLEKIAAKEFVNWLLAQK

SEQ ID NO. 7
Y-Aib-EGTFTSDYSIYLDKKAQRAFVNWLLA-Aib-K

SEQ ID NO. 8
YAEGTFTSDYSIYLDKKAQRAFVNWLLA-Aib-K

SEQ ID NO. 9
YGEGTFTSDYSIYLDKKAQRAFVNWLLA-Aib-K

SEQ ID NO. 10
Y-Aib-EGTFSSDYSIYLDKKAQRAFVNWLLA-Aib-K

SEQ ID NO. 11
Y-Aib-EGTFTSDLSIYLDKKAQRAFVNWLLA-Aib-K

SEQ ID NO. 12
Y-Aib-EGTFTSDSSIYLDKKAQRAFVNWLLA-Aib-K

SEQ ID NO. 13
Y-Aib-EGTFTSDYLIYLDKKAQRAFVNWLLA-Aib-K

SEQ ID NO. 14
Y-Aib-EGTFTSDYSIALDKKAQRAFVNWLLA-Aib-K

SEQ ID NO. 15
Y-Aib-EGTFTSDYSIYSDKKAQRAFVNWLLA-Aib-K

SEQ ID NO. 16
Y-Aib-EGTFTSDYSIYLEKKAQRAFVNWLLA-Aib-K

SEQ ID NO. 17
Y-Aib-EGTFTSDYSIALEKKAQRAFVNWLLA-Aib-K

SEQ ID NO. 18
Y-Aib-EGTFTSDYSIYLDSKAQRAFVNWLLA-Aib-K

SEQ ID NO. 19
Y-Aib-EGTFTSDYSIYLDEKAQRAFVNWLLA-Aib-K
```

```
                                                SEQ ID NO. 20
Y-Aib-EGTFTSDYSIYLDSKAKRAFVNWLLA-Aib-K

SEQ ID NO. 21
Y-Aib-EGTFTSDYSIYLDKKAQKEFVNWLLA-Aib-K

SEQ ID NO. 22
Y-Aib-EGTFTSDYSIYLDKKAQRAFVKWLLA-Aib-K

SEQ ID NO. 22
Y-Aib-EGTFTSDYSIYLDKKAQRAFVNWLVA-Aib-K

SEQ ID NO. 24
Y-Aib-EGTFTSDYSIYLDKKAQRAFVNWLSA-Aib-K

SEQ ID NO. 25
Y-Aib-EGTFTSDYSIYLDKKAQRAFVNWLKA-Aib-K

SEQ ID NO. 26
Y-Aib-EGTFTSDYSIYLDKKAQRAFVNWLL-Aib-K

SEQ ID NO. 27
Y-Aib-EGTFTSDYSIYLDKKAQRAFVNWLLA-Aib-KYG-1Nal-LDF

SEQ ID NO. 28
Y-Aib-EGTFTSDYSIYLDKKAQRAFVNWLLAYG-1Nal-LDF

SEQ ID NO. 29
Y-Aib-EGTFTSDYSIYLDKKAEKAFVNWLLA-Aib-K

SEQ ID NO. 30
Y-Aib-EGTFTSDYSIYLDKKAQRAFVNWLLA-Aib-GPSSGAPPPS

SEQ ID NO. 31
Y-Aib-EGTFTSDYSIYLDKKAQRAFVNWLLA-Aib-GPSSGAPPS

SEQ ID NO. 32
Y-Aib-EGTFTSDYSIYLEKKAAEFVNWLLAQK

SEQ ID NO. 35
Y-Aib-EGTFTSDYSIYLDK-K(15-carboxy-pentadecanoyl-
isoGlu)-AQRAFVNWLLA-Aib-K SEQ ID NO. 36
Y-Aib-EGTFTSDYSI-Aib-LDK-K(Hexadecanoyl-isoGlu)-
AQRAFVEWLLAQGPSSGAPPPS SEQ ID NO. 37
Y-Aib-EGTFTSDYSIYLDK-K(hexadecanoyl-isoGlu)-
AQRAFVEWLLAQGPSSGAPPPS SEQ ID NO. 38
Y-Aib-EGTFTSDYSIYLDE-K(hexadecanoyl-isoGlu)-
AAKEFIEWLESA SEQ ID NO. 39
Y-Aib-EGTFTSDYSIYLDK-K(hexadecanoyl-isoGlu)-
AQRAFVNWLLA-Aib-KPSSGAPPPS SEQ ID NO. 40
Y-Aib-EGTFTSDYSIALDK-K(hexadecanoyl-isoGlu)-
AQRAFVNWLVA-Aib-KPSSGAPPPS SEQ ID NO. 41
Y-Aib-EGTFTSDYSIYLE-KKAAKDFVEWLLSA SEQ ID NO. 93
Y-Aib-EGTFTSDYSIYLE-KKAAHDFVEWLLSA SEQ ID NO. 42
Y-Aib-EGTFTSDYSIYLEKKAQKEFVEWLLSA SEQ ID NO. 43
Y-Aib-EGTFTSDYSIYLDEKAAKDFVEWLLSA SEQ ID NO. 44
Y-Aib-EGTFTSDYSIYLESKAAHDFVEWLLSA SEQ ID NO. 45
Y-Aib-EGTFTSDYSIYLDKKAAHDFVEWLLSA SEQ ID NO. 46
Y-Aib-EGTFTSDYSIYLEKKAAKEFVEWLLSA SEQ ID NO. 47
Y-Aib-EGTFTSDYSIYLDSKAAHDFVEWLLRA SEQ ID NO. 48
Y-Aib-EGTFTSDYSKYLDS-K(Hexadecanoyl-isoGlu)-
AAHDFVEWLLSA SEQ ID NO. 49
Y-Aib-EGTFTSDYSIYLEK-K(Hexadecanoyl-isoGlu)-
AAKEFVEWLLSA SEQ ID NO. 50
Y-Aib-EGTFTSDYSIYLDS-K(Hexadecanoyl-isoGlu)-
AAHDFVEWLLRA SEQ ID NO. 51
Y-Aib-EGTFTSDYSIYLDE-K(Hexadecanoyl-isoGlu)-
AAKDFVEWLESA SEQ ID NO. 52
Y-Aib-EGTFTSDYSKYLDE-K(Hexadecanoyl-isoGlu)-
AAKDFIEWLESA SEQ ID NO. 53
Y-Aib-EGTFTSDYSIYLDE-K(Hexadecanoyl-isoGlu)-
AAKDFIEWLESA SEQ ID NO. 54
Y-Aib-EGTFTSDYSKYLDS-K(Hexadecanoyl-isoGlu)-
AAHDFVEWLLRA SEQ ID NO. 55
Y-Aib-EGTFTSDYSIYLDE-K(Hexadecanoyl-isoGlu)-
AAKDFVEWLLSA SEQ ID NO. 56
Y-Aib-EGTFTSDYSIYLDS-K(Hexadecanoyl-isoGlu)-
AAHDFVEWLLSAGPSSGAPPPS SEQ ID NO. 57
Y-Aib-EGTFTSDYSIYLEK-K-(Hexadecanoyl-isoGlu)-
AAKEFVEWLLSAGPSSGAPPPS SEQ ID NO. 58
Y-Aib-EGTFTSDYSIYLDSKAAHDFVEWLLSAGPSSGAPPPS SEQ ID NO: 69
Y-Aib-EGTFTSDYSIYLDE-K(Hexadecanoyl-isoGlu)-
AAHDFVEWLLSA
```

Lipophilic Substituents

One or more of the amino acid side chains in a compound employed in the context of the invention may be conjugated to a lipophilic substituent $Z^1$. Without wishing to be bound by theory, it is thought that the lipophilic substituent binds albumin in the blood stream, thus shielding the compounds employed in the context of the invention from enzymatic degradation which can enhance the half-life of the compounds. The lipophilic substituent may also modulate the potency of the compound, e.g., with respect to the GIP receptor and/or the GLP-1 receptor.

In certain embodiments, only one amino acid side chain is conjugated to a lipophilic substituent. In other embodiments, two amino acid side chains are each conjugated to a lipophilic substituent. In yet further embodiments, three or even more amino acid side chains are each conjugated to a lipophilic substituent. When a compound contains two or more lipophilic substituents, they may be the same or different.

The lipophilic substituent $Z^1$ may be covalently bonded to an atom in the amino acid side chain, or alternatively may be conjugated to the amino acid side chain by one or more spacers $Z^2$.

The term "conjugated" is used here to describe the covalent attachment of one identifiable chemical moiety to another, and the structural relationship between such moieties. It should not be taken to imply any particular method of synthesis. The spacer $Z^2$, when present, is used to provide a spacing between the compound and the lipophilic moiety.

The lipophilic substituent may be attached to the amino acid side chain or to the spacer via an ester, a sulphonyl ester, a thioester, an amide or a sulphonamide. Accordingly it will be understood that preferably the lipophilic substituent includes an acyl group, a sulphonyl group, an N atom, an O atom or an S atom which forms part of the ester, sulphonyl ester, thioester, amide or sulphonamide. Preferably, an acyl group in the lipophilic substituent forms part of an amide or ester with the amino acid side chain or the spacer.

The lipophilic substituent may include a hydrocarbon chain having 10 to 24 carbon (C) atoms, e.g. 10 to 22 C atoms, e.g. 10 to 20 C atoms. Preferably it has at least 11 C atoms, and preferably it has 18 C atoms or fewer. For example, the hydrocarbon chain may contain 12, 13, 14, 15, 16, 17 or 18 carbon atoms. The hydrocarbon chain may be linear or branched and may be saturated or unsaturated. Furthermore, it can include a functional group in the end of the lipophilic chain, e.g., carboxylic acid which may or may not be protected during synthesis. From the discussion above it will be understood that the hydrocarbon chain is preferably substituted with a moiety which forms part of the attachment to the amino acid side chain or the spacer, for example an acyl group, a sulphonyl group, an N atom, an O atom or an S atom.

Most preferably, the hydrocarbon chain is substituted with acyl, and accordingly the hydrocarbon chain may be part of an alkanoyl group, for example a dodecanoyl, 2-butyloctanoyl, tetradecanoyl, hexadecanoyl, heptadecanoyl, octadecanoyl or eicosanoyl group. An example of a functionalized hydrocarbon chain is the 15-carboxy-pentadecanoyl.

As mentioned above, the lipophilic substituent $Z^1$ may be conjugated to the amino acid side chain by one or more spacers $Z^2$. When present, the spacer is attached to the lipophilic substituent and to the amino acid side chain. The spacer may be attached to the lipophilic substituent and to the amino acid side chain independently by an ester, a sulphonyl ester, a thioester, an amide or a sulphonamide. Accordingly, it may include two moieties independently selected from acyl, sulphonyl, an N atom, an O atom or an S atom. The spacer may consist of a linear C1-10 hydrocarbon chain or more preferably a linear C1-5 hydrocarbon chain. Furthermore, the spacer may be substituted with one or more substituents selected from C1-6 alkyl, C1-6 alkyl amine, C1-6 alkyl hydroxy and C1-6 alkyl carboxy.

The spacer may be, for example, a residue of any naturally occurring or unnatural amino acid. For example, the spacer may be a residue of (Gly, Pro, Ala, Val, Leu, Ile, Met, Cys, Phe, Tyr, Trp, His, Lys, Arg, Gln, Asn, α-Glu, γ-Glu, ε-Lys, Asp, Ser, Thr, Gaba, Aib, β-Ala (i.e. 3-aminopropanoyl), 4-aminobutanoyl, 5-aminopentanoyl, 6-aminohexanoyl, 7-aminoheptanoyl, 8-aminooctanoyl, 9-aminononanoyl, 10-aminodecanoyl or 8-amino-3,6-dioxaoctanoyl. In certain embodiments, the spacer is a residue of Glu, γ-Glu, ε-Lys, β-Ala (i.e. 3-aminopropanoyl), 4-aminobutanoyl, 8-aminooctanoyl or 8-amino-3,6-dioxaoctanoyl. In the present context, γ-Glu and isoGlu are used interchangeably. The amino acid side chain to which the lipophilic substituent is conjugated is a side chain, e.g., of a Glu, Lys, Ser, Cys, Dbu, Dpr or Orn residue. For example, it may be a side chain of a Lys, Glu or Cys residue. Where two or more side chains carry a lipophilic substituent, they may be independently selected from these residues. Thus the amino acid side chain includes a carboxy, hydroxyl, thiol, amide or amine group, for forming an ester, a sulphonyl ester, a thioester, an amide, or a sulphonamide with the spacer or lipophilic substituent.

An example of a lipophilic substituent comprising a lipophilic moiety $Z^1$ m and spacer $Z^2$ is shown in the formula below:

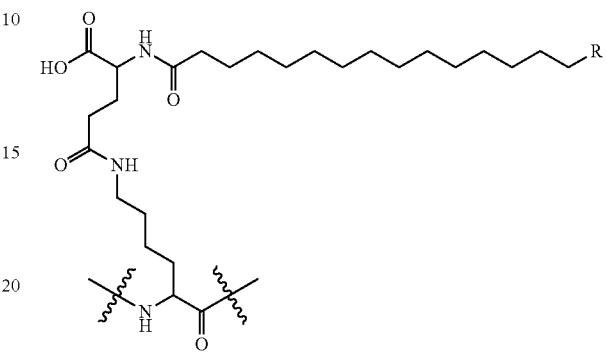

Here, the side chain of a Lys residue is covalently attached to a γ-Glu spacer ($Z^2$) via an amide linkage. A hexadecanoyl group ($Z^1$, R=$CH_3$) is covalently attached to the γ-Glu spacer via an amide linkage. This combination of lipophilic moiety and spacer, conjugated to a Lys residue, may be referred to by the short-hand notation K(Hexadecanoyl-γ-Glu), e.g., when shown in formulae of specific compounds. γ-Glu can also be referred to as isoGlu, and a hexadecanoyl group as a palmitoyl group. Thus it will be apparent that the notation (Hexadecanoyl-γ-Glu) is equivalent to the notations (isoGlu(Palm)) or (isoGlu(Palmitoyl)) as used for example in PCT/GB2008/004121. In different embodiments, the 15-carboxy-pentadecanoyl group ($Z^2$. R=COOH) is covalently attached to the γ-Glu spacer via an amide linkage. The combination of lipophilic moiety with a functional group like COOH and a spacer, conjugated to a Lys residue may be referred to as K(15-carboxy-pentadecanoyl-γ-Glu) or K(15-carboxy-pentadecanoyl-isoGlu).

In certain embodiments, a GIP analogue of the invention is conjugated with a lipophilic substituent to one or more of amino acid positions 16, 17, 19, 20, 24, 27, 28, 30 and 32.

The skilled person will be well aware of suitable techniques for preparing the compounds employed in the context of the invention. For examples of suitable chemistry, see, e.g., WO98/08871, WO00/55184, WO00/55119, Madsen et al. (*J. Med. Chem.* 2007, 50, 6126-32), and Knudsen et al. 2000 (*J. Med Chem.* 43, 1664-1669).

Non-Proteinogenic Amino Acids

One or more of the amino acids of a GIP analogue compound may be a non-proteinogenic (non-naturally occurring) amino acid. Non-proteinogenic amino acids may include those amino acids not encompassed by the 20 "standard" amino acids used in protein synthesis, e.g., alanine, arginine, aspartate, asparagine, cysteine, glutamate, glutamine, glycine, histidine, isoleucine, leucine, lysine, methionine, phenylalanine, proline, serine, threonine, tryptophan, tyrosine, and valine. Examples of non-proteinogenic amino acids include, but are not limited to, para amino benzoic acid (PABA), 2-amino benzoic acid, anthranilic acid, p-hydroxybenzoic acid (PHBA), 3-amino benzoic acid, 4-aminomethyl benzoic acid, 4-amino salicylic acid (PAS), 4-amino cyclohexanoic acid 4-aminophenyl acetic acid, 4-amino-hippuric acid, 4-amino-2-chlorobenzoic acid, 6-aminonicotinic acid, methyl-6-aminonicotinate, 4-amino methyl salicylate, 2-amino thiazole-4-acetic acid, 2-amino-4-(2-aminophenyl)-4-oxobutanoic acid (L-kynurenine), O-methyl serine, acetylamino alanine, β-alanine, β-(acetylamino)alanine, β-aminoalanine, β-chloroalanine, citrulline, homocitrulline, hydroxyproline, homoarginine, homoserine, homotyrosine, homoproline, ornithine, 4-amino-phenylalanine, sarcosine, biphenylalanine, homophenylalanine, 4-nitro-phenylalanine, 4-fluoro-phenylalanine, 2,3,4,5,6-pentafluoro-phenylalanine, norleucine, cyclohexylalanine, N-methyl-alanine, N-methyl-glycine, N-methyl-glutamic acid, tert-butylglycine, α-aminobutyric acid, α-aminoisobutyric acid (AIB), 2-aminoisobutyric acid, 2-aminoindane-2-carboxylic acid, selenomethionine, lanthionine, dehydroalanine, γ-aminobutyric acid, naphthylalanine, aminohexanoic acid, phenylglycine, pipecolic acid, 2,3-diaminoproprionic acid, tetrahydroisoquinoline-3-carboxylic acid, taurine, tert-leucine, tert-butylalanine, cyclohexylglycine, diethylglycine, and dipropylglycine.

C-Terminal Amidation

The major biologically active fragment of a GIP analogue is produced as a 42-amino acid peptide with a free carboxylic acid at the C-terminal. In some embodiments, a compound employed in the context of the invention may also comprise a truncated or full length analogue of naturally occurring GIP and further comprise a C-terminal modification, e.g., amidation.

Clinical Utility

The GIP analogue compounds employed in the context of the invention may provide an attractive treatment option for metabolic diseases including obesity, diabetes mellitus (diabetes), obesity-related disorders, and diabetes-related disorders. Diabetes comprises a group of metabolic diseases characterized by hyperglycemia resulting from defects in insulin secretion, insulin action, or both. Diabetes is classified into type 1 diabetes, type 2 diabetes and gestational diabetes on the basis on pathogenic characteristics. Type 1 diabetes accounts for 5-10% of all diabetes cases and is caused by auto-immune destruction of insulin-secreting pancreatic β-cells. Acute signs of diabetes include excessive urine production, resulting compensatory thirst and increased fluid intake, blurred vision, unexplained weight loss, lethargy, and changes in energy metabolism. However, in type 2 diabetes symptoms are often not severe or may be absent. The chronic hyperglycemia of diabetes is associated with long-term damage, dysfunction, and failure of various organs, notably the eyes, kidneys, nerves, heart and blood vessels.

Type 2 diabetes accounts for 90-95% of diabetes cases and is a result of a complex set of metabolic disorders. However, symptoms are often not severe or may be absent. Type 2 diabetes is the consequence of endogenous insulin production becoming insufficient to maintain plasma glucose levels below diagnostic thresholds.

Gestational diabetes refers to any degree of glucose intolerance identified during pregnancy.

Pre-diabetes includes impaired fasting glucose and impaired glucose tolerance and refers to those states that occur when blood glucose levels are elevated but below the levels that are established for the clinical diagnosis for diabetes.

A large proportion of people with type 2 diabetes and pre-diabetes are at increased risk of morbidity and mortality due to the high prevalence of additional metabolic risk factors, including abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension) a prothrombotic state (e.g. high fibrinogen or plasminogen activator inhibitor-1 in the blood), and/or a proinflammatory state (e.g., elevated C-reactive protein in the blood).

Conversely, obesity confers an increased risk of developing pre-diabetes, type 2 diabetes as well as, e.g., certain types of cancer, obstructive sleep apnea and gall-bladder disease. Dyslipidemia is associated with increased risk of cardiovascular disease. High Density Lipoprotein (HDL) is of clinical importance since an inverse correlation exists between plasma HDL concentrations and risk of atherosclerotic disease. The majority of cholesterol stored in atherosclerotic plaques originates from LDL and hence an elevated concentration of Low Density Lipoproteins (LDL) is closely associated with atherosclerosis. The HDL/LDL ratio is a clinical risk indictor for atherosclerosis and coronary atherosclerosis in particular.

Compounds employed in the context of the invention act as GIP-GLP1 dual agonists. The dual agonist may combine the effect of GIP, e.g., on fat metabolism and weight loss, and blood glucose, with the effect of GLP-1, e.g., on blood glucose levels and food intake. They may therefore act to accelerate elimination of excessive adipose tissue, induce sustainable weight loss, and improve glycemic control. Dual GIP-GLP1 agonists may also act to reduce cardiovascular risk factors such as high cholesterol, such as high LDL-cholesterol.

The GIP-GLP1 dual agonist compounds of the present invention may therefore be used as pharmaceutical agents for preventing weight gain, promoting weight loss, reducing excess body weight or treating obesity (e.g., by control of appetite, feeding, food intake, calorie intake, and/or energy expenditure and lipolysis), including morbid obesity, as well as associated diseases and health conditions including but not limited to obesity linked inflammation, obesity linked gallbladder disease and obesity induced sleep apnea. The GIP-GLP1 dual agonist compounds employed in the context of the invention may also be used for treatment of insulin resistance, glucose intolerance, pre-diabetes, increased fasting glucose, type 2 diabetes, hypertension, dyslipidemia (or a combination of these metabolic risk factors), atherosclerosis, arteriosclerosis, coronary heart disease, peripheral artery disease and stroke. These are all conditions which may be associated with obesity. However, the effects of the compounds employed in the context of the invention on these conditions may be mediated in whole or in part via an effect on body weight, or may be independent thereof. The GIP-GLP1 dual agonist compounds employed in the context of the invention may also be used for treating a stomach and/or bowel-related disorder.

The GIP-GLP1 dual agonist compounds, nucleic acids, vectors, host cells, and pharmaceutical compositions thereof, also may be used for the treatment and/or prevention of any of the diseases, disorders, or conditions described herein, including metabolic diseases, diabetes or diabetes related disorders, stomach and/or bowel related disorder, and/or obesity or obesity related disorders. In some embodiments, the GIP-GLP1 dual agonist compounds, nucleic acids, vectors, host cells, also may be used for the preparation of a medicament for the treatment and/or prevention of any of the diseases, disorders, or conditions described herein, including metabolic diseases, diabetes or diabetes related disorders, and/or obesity or obesity related disorders. In certain embodiments, the diabetes related disorder is selected from insulin resistance, glucose intolerance, increased fasting glucose, pre-diabetes, type 1 diabetes, type 2 diabetes, gestational diabetes hypertension, dyslipidemia, or a combination thereof. In certain embodiments, the diabetes related disorder is selected from atherosclerosis, arteriosclerosis, coronary heart disease, peripheral artery disease and stroke; or associated with a condition selected from atherogenic dyslipidemia, blood fat disorders, elevated blood pressure, hypertension, a prothrombotic state, and proinflammatory state, or a combination thereof. In certain embodiments, the blood fat disorder is selected from high triglycerides, low HDL cholesterol, high LDL cholesterol, plaque buildup in artery walls, or a combination thereof. In certain embodiments, the prothrombotic state is selected from high fibrinogen levels in the blood and high plasminogen activator inhibitor-1 levels in the blood. In certain embodiments, the proinflammatory state is an elevated C-reactive protein level in the blood. In certain embodiments, the obesity related disorder is selected from obesity linked inflammation, obesity linked gallbladder disease and obesity induced sleep apnea.

In some embodiments, the invention also provides a therapeutic kit comprising a GIP analogue of the invention, a nucleic acid molecule of the invention, an expression vector of the invention, or a host cell of the invention, each optionally in combination with a pharmaceutically acceptable carrier. In some embodiments, the invention provides a device comprising a GIP analogue of the invention, a nucleic acid molecule of the invention, an expression vector of the invention, or a host cell of the invention for delivery of the GIP analogue to a subject.

Pharmaceutical Compositions

The GIP-GLP1 dual agonist compounds of the present invention, or salts or solvates thereof, may be formulated as pharmaceutical compositions prepared for storage or administration, which typically comprise a therapeutically effective amount of a compound employed in the context of the invention, or a salt or solvate thereof, in a pharmaceutically acceptable carrier. In some embodiments, the pharmaceutical composition is formulated as a liquid suitable for administration by injection or infusion, or which is formulated to cause slow release of the GIP-GLP1 dual agonist compound The therapeutically effective amount of a compound of the present invention will depend, e.g., on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. Suitable pH buffering agents may be, e.g., phosphate, citrate, acetate, lactate, maleate, tris/hydroxymethyl)aminomethane (TRIS). N-Tris(hydroxymethyl)methyl-3-aminopropanesulphonic acid (TAPS), ammonium bicarbonate, diethanolamine, histidine, which in certain embodiments is a preferred buffer, arginine, lysine, or acetate or mixtures thereof. The term further encompasses any agents listed in the US Pharmacopeia for use in animals, including humans.

The term "pharmaceutically acceptable salt" refers to a salt of the compound. Salts include pharmaceutically acceptable salts, such as, e.g., acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" may also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms (e.g. weight gain, hyperglycemia) when compared to the absence of treatment, and is not necessarily meant to imply complete cessation of the relevant condition.

The pharmaceutical compositions of the invention may be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of an injection pen. Compositions may be formulated for any suitable route and means of administration. Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for certain of the compounds described herein.

Combination Therapy

In certain embodiments, a GIP-GLP-1 dual agonist compound employed in the context of the invention may be administered as part of a combination therapy with at least one other agent for treatment of diabetes, obesity, dyslipidemia, or hypertension.

In such cases, the at least two active agents may be given together or separately, and as part of the same pharmaceutical formulation or as separate formulations. Thus, the GIP-GLP-1 dual agonist compound employed in the context of the invention (or the salt or solvate thereof) may be used in combination with an antidiabetic agent including but not limited to metformin, a sulfonylurea, a glinide, a DPP-IV inhibitor, a glitazone, or insulin. In certain embodiments, the compound or salt or solvate thereof is used in combination with insulin. DPP-IV inhibitor, sulfonylurea or mefformin, particularly sulfonylurea or metformin, for achieving adequate glycemic control. In certain preferred embodiments, the compound or salt or solvate thereof is used in combination with insulin or an insulin analogue for achieving adequate glycemic control. Examples of insulin analogues include but are not limited to Lantus®, NovoRapid®, Humalog®, NovoMix®, Actraphane HM®, Levemir® and Apidra®.

In certain embodiments, the GIP-GLP-1 dual agonist compound or salt or solvate thereof may further be used in combination with one or more of an anti-obesity agent, including but not limited to a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

In certain embodiments, the GIP-GLP-1 dual agonist compound or salt or solvate thereof may be used in combination with an anti-hypertension agent, including but not limited to an angiotensin-converting enzyme inhibitor, angiotensin II receptor blocker, diuretics, beta-blocker, or calcium channel blocker.

In certain embodiments, the GIP-GLP-1 dual agonist compound or salt thereof may be used in combination with an anti-dyslipidemia agent, including but not limited to a statin, a fibrate, a niacin and/or a cholesterol absorption inhibitor.

Nucleic Acids, Vectors, and Host Cells

In some embodiments, the invention provides a nucleic acid molecule comprising a nucleic acid sequence encoding a GIP analogue of the invention. In some embodiments, the invention provides an expression vector comprising a nucleic acid sequence encoding a GIP analogue of the invention, in combination with control sequences to direct its expression. In some embodiments, the invention provides a host cell transformed with such an expression vector. In some embodiments, the invention provides a method of producing a GIP analogue of the invention, the method comprising culturing the host cells described above under conditions suitable for expressing the GIP analogue and purifying the GIP analogue thus produced. In some embodiments, the invention provides a nucleic acid molecule, an expression vector, or a host cell, as described above, for use in therapy. In some embodiments, the invention provides the use of a nucleic acid molecule according, an expression vector, or a host cell, as described above, in the preparation of a medicament for the treatment and/or prevention of a metabolic disorder.

It will be understood that a nucleic acid will typically only be capable of encoding a polypeptide of the invention when the polypeptide sequence consists entirely of the 20 naturally occurring (proteinogenic) amino acids. However, nucleic acids may be employed which encode a fragment or precursor of the compound of the invention.

The peptide compounds of the invention may be manufactured by standard peptide synthetic methods, by use of recombinant expression systems, or by any other suitable method. Thus, the compounds may be synthesized in a number of ways, including, e.g., methods comprising:

(a) synthesizing the peptide compound by standard solid-phase or liquid-phase methodology, either stepwise or by fragment assembly, and isolating and purifying the final peptide compound product;

(b) expressing a nucleic acid construct that encodes the peptide compound or a fragment or precursor thereof in a host cell and recovering the expression product from the host cell culture; or (c) effecting cell-free in vitro expression of a nucleic acid construct encoding the peptide compound or a fragment or precursor thereof, and recovering the expression product; or by any combination of the methods of (a), (b) or (c) to obtain fragments of the peptide compound, subsequently joining (e.g., ligating) the fragments to obtain the peptide compound, and recovering the peptide compound.

The method of synthesis may comprise the step of chemically modifying one of more amino acid side chains in a precursor peptide to yield a compound of the invention. Such modification may, for example, introduce a non-naturally occurring amino acid, convert one or more amino acids into non-naturally occurring amino acids, introduce an intramolecular bridge between two amino acid side chains, e.g. by forming a lactam ring between a Glu and a Lys residue, or introduce a lipophilic substituent at a lysine residue.

It may be preferable to synthesize the peptide compounds of the invention by means of solid-phase or liquid-phase peptide synthesis. In this context, reference may be made to WO 98/11125 or, inter alia, Fields. G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present invention also provides methods for producing a polypeptide of the invention according to above recited methods; a nucleic acid molecule encoding part or all of a polypeptide of the invention or a precursor thereof, a vector comprising at least one nucleic acid of the invention, expression vectors comprising at least one nucleic acid of the invention capable of producing a polypeptide of the invention when introduced into a host cell, and a host cell comprising a nucleic acid molecule, vector or expression vector of the invention.

EXAMPLES

The following examples demonstrate certain embodiments of the present invention. However, it is to be understood that these examples neither purport nor are they intended to be wholly definitive as to conditions and scope of this invention. The examples were carried out using standard techniques, which are well known and routine to those of skill in the art, except where otherwise described in detail. The following examples are presented for illustrative purposes only, and should not be construed in any way as limiting the scope of this invention.

Disclosed are GIP-GLP1 dual agonist compounds that exhibit signaling selectivity, and methods for screening these compounds. Signaling selectivity may be, for example, preferential pathway activation or preferential pathway inhibition, or both. The GIP-GLP1 dual agonist compounds may be useful for the treatment and/or prevention of diseases or conditions caused or characterized by excess body weight, including, but not limited to, obesity, morbid obesity, obesity linked inflammation, obesity linked gallbladder disease, obesity induced sleep apnea, metabolic syndrome, pre-diabetes, insulin resistance, glucose intolerance, type 2 diabetes, type I diabetes, hypertension, atherogenic dyslipidaemia, atherosclerosis, arteriosclerosis, coronary heart disease, peripheral artery disease, and stroke or microvascular disease.

While some embodiments of the invention have been described by way of illustration, it will be apparent that the invention can be put into practice with many different modifications, variations and adaptations, and with the use of numerous equivalents or alternative solutions that are within the scope of persons skilled in the art, without departing from the spirit of the invention or exceeding the scope of the claims.

All publications, patents, and patent applications referred to herein are herein incorporated by reference in their entirety to the same extent as if each individual publication, patent or patent application was specifically and individually indicated to be incorporated by reference in its entirety.

Example 1

The methods used in the instant invention are described below, except where expressly indicated otherwise.
General Synthesis of Acylated GIP Analogues Solid phase peptide synthesis was performed on a CEM Liberty Peptide Synthesizer using standard Fmoc chemistry. TentaGel S Ram resin (1 g; 0.25 mmol/g) was swelled in NMP (10 ml) prior to use and transferred between tube and reaction vessel using DCM and NMP.
Coupling An Fmoc-amino acid in NMP/DMF/DCM (1:1:1; 0.2 M; 5 ml) was added to the resin in a CEM Discover microwave unit together with HATU/DMF or COMU/DMF (0.5 M; 2 ml) and DIPEA/NMP (2.0 M; 1 ml). The coupling mixture was heated to 75° C. for 5 min while nitrogen was bubbled through the mixture. The resin was then washed with NMP (4×10 ml).
Deprotection Piperidine/DMF (20%; 10 ml) was added to the resin for initial deprotection and the mixture was heated by microwaves (30 sec; 40° C.). The reaction vessel was drained and a second portion of piperidine/NMP (20%; 10 ml) was added and heated (75° C.; 3 min.) again. The resin was then washed with DMF (6×10 ml).
Side Chain Acylation Fmoc-Lys(ivDde)-OH or alternatively another amino acid with an orthogonal side chain protective group was introduced at the position of the acylation. The N-terminal of the peptide backbone was then Boc-protected using Boc2O or alternatively by using a Boc-protected amino acid in the last coupling. While the peptide was still attached to the resin, the orthogonal side chain protective group was selectively cleaved using freshly prepared hydrazine hydrate (2-4%) in NMP for 2×15 min. The unprotected lysine side chain was first coupled with Fmoc-Glu-OtBu or another spacer amino acid, which was deprotected with piperidine and acylated with a lipophilic moiety using the peptide coupling methodology as described above. Alternatively, the acylation moiety was introduced as a premade building block e.g. Fmoc-Lys(hexadecanoyl-gamma-Glu)-OH where gamm-Glu is the coupling of Glutamic acid through the side-chain.
Abbreviations employed are as follows:
COMU: 1-[(1-(cyano-2-ethoxy-2-oxoethylideneaminooxy)-dimethylamino-morpholinomethylene)]methanaminium hexaflourophosphate
ivDde: 1-(4,4-dimethyl-2,6-dioxocyclohexylidene)3-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EtOH: ethanol
Et$_2$O: diethyl ether
HATU: N-[(dimethylamino)-1H-1,2,3-triazol[4,5-b]pyridine-1-ylmethylene]-N-methylmethanaminium hexafluorophosphate N-oxide
MeCN: acetonitrile
NMP: N-methylpyrrolidone
TFA: trifluoroacetic acid
TIS: triisopropylsilane
Cleavage The resin was washed with EtOH (3×10 ml) and Et$_2$O (3×10 ml) and dried to constant weight at room temperature (r.t.). The crude peptide was cleaved from the resin by treatment with TFA/TIS/water (95/2.5/2.5; 40 ml, 2 h; r.t.). Most of the TFA was removed at reduced pressure and the crude peptide was precipitated and washed three times with diethylether and dried to constant weight at room temperature.
HPLC Purification of the Crude Peptide The crude peptide was purified to greater than 90% by preparative reverse phase HPLC using a PerSeptive Biosystems VISION Workstation equipped with a C-18 column (5 cm; 10 μm) and a fraction collector and run at 35 ml/min with a gradient of buffer A (0.1% TFA, aq.) and buffer B (0.1% TFA, 90% MeCN, aq.). Fractions were analyzed by analytical HPLC and MS and relevant fractions were pooled and lyophilized. The final product was characterized by HPLC and MS.

The synthesized compounds are shown in Table 1 and Table 2

TABLE 1

| Compound No. | Sequence |
|---|---|
| 1 | Hy-Y-Aib-EGTFISDYSIYLEKKAAKEFVNWLLAQK-NH$_2$ (SEQ ID NO: 94) |
| 2 | Hy-Y-Aib-EGTFTSDYSI-Aib-LDKKAQRAFVEWLLAQGPSSGAPPPS-NH$_2$ (SEQ ID NO: 95) |
| 3 | Hy-Y-Aib-EGTFTSDYSIALDKIAQRAFVNWLVA-Aib-K-NH$_2$ (SEQ ID NO: 96) |
| 4 | Hy-Y-Aib-EGTFISDYSIYLEKIAAKEFVNWLLAQK-NH$_2$ (SEQ ID NO: 97) |
| 5 | Hy-Y-Aib-EGTFTSDYSIYLDKKAQRAFVNWLLA-Aib-K-NH$_2$ (SEQ ID NO: 98) |

TABLE 2

| Compound No. | Sequence |
|---|---|
| 6 | pGlu-YAEGTFTSDYSIYLDKKAQRAFVNWLLA-Aib-K-NH$_2$ (SEQ ID NO: 99) |
| 7 | Hy-YGEGTFTSDYSIYLDKKAQRAFVNWLLA-Aib-K-NH$_2$ (SEQ ID NO: 100) |
| 8 | Hy-Y-Aib-EGTFSSDYSIYLDKKAQRAFVNWLLA-Aib-K-NH$_2$ (SEQ ID NO: 101) |
| 9 | Hy-Y-Aib-EGTFTSDLSIYLDKKAQRAFVNWLLA-Aib-K-NH$_2$ (SEQ ID NO: 102) |
| 10 | Hy-Y-Aib-EGTFTSDSSIYLDKKAQRAFVNWLLA-Aib-K-NH$_2$ (SEQ ID NO: 148) |
| 11 | Hy-Y-Aib-EGTFTSDYLIYLDKKAQRAFVNWLLA-Aib-K-NH$_2$ (SEQ ID NO: 103) |
| 12 | Hy-Y-Aib-EGTFTSDYSIALDKKAQRAFVNWLLA-Aib-K-NH$_2$ (SEQ ID NO: 104) |
| 13 | Hy-Y-Aib-EGTFTSDYSIYSDKKAQRAFVNWLLA-Aib-K-NH$_2$ (SEQ ID NO: 105) |
| 14 | Hy-Y-Aib-EGTFTSDYSIYLEKKAQRAFVNWLLA-Aib-K-NH$_2$ (SEQ ID NO: 106) |
| 15 | Hy-Y-Aib-EGTFTSDYSIALEKKAQRAFVNWLLA-Aib-K-NH$_2$ (SEQ ID NO: 107) |
| 16 | Hy-Y-Aib-EGTFTSDYSIYLDSKAQRAFVNWLLA-Aib-K-NH$_2$ (SEQ ID NO: 108) |
| 17 | Hy-Y-Aib-EGTFTSDYSIYLDEKAQRAFVNWLLA-Aib-K-NH$_2$ (SEQ ID NO: 109) |
| 18 | Hy-Y-Aib-EGTFTSDYSIYLDSKAKRAFVNWLLA-Aib-K-NH$_2$ (SEQ ID NO: 110) |
| 19 | Hy-Y-Aib-EGTFTSDYSIYLDKKAQKEFVNWLLA-Aib-K-NH$_2$ (SEQ ID NO: 111) |
| 20 | Hy-Y-Aib-EGTFTSDYSIYLDKKAQRAFVKWLLA-Aib-K-NH$_2$ (SEQ ID NO: 112) |
| 21 | Hy-Y-Aib-EGTFTSDYSIYLDKKAQRAFVNWLVA-Aib-K-NH$_2$ (SEQ ID NO: 113) |
| 22 | Hy-Y-Aib-EGTFTSDYSIYLDKKAQRAFVNWLSA-Aib-K-NH$_2$ (SEQ ID NO: 149) |
| 23 | Hy-Y-Aib-EGTFTSDYSIYLDKKAQRAFVNWLKA-Aib-K-NH$_2$ (SEQ ID NO: 114) |
| 24 | Hy-Y-Aib-EGTFTSDYSIYLDKKAQRAFVNWLL-Aib-K-NH$_2$ (SEQ ID NO: 115) |
| 25 | Hy-Y-Aib-EGTFTSDYSIYLDKKAQRAFVNWLLA-Aib-KYG-1Nal-LDF-NH$_2$ (SEQ ID NO: 116) |
| 26 | Hy-Y-Aib-EGTFTSDYSIYLDKKAQRAFVNWLLAYG-1Nal-LDF-NH$_2$ (SEQ ID NO: 117) |
| 27 | Hy-Y-Aib-EGTFTSDYSIYLDKKAEKAFVNWLLA-Aib-K-NH$_2$ (SEQ ID NO: 118) |
| 28 | Hy-Y-Aib-EGTFTSDYSIYLDKKAQRAFVNWLLA-Aib-GPSSGAPPPS-NH$_2$ (SEQ ID NO: 119) |
| 29 | Hy-Y-Aib-EGTFTSDYSIYLDKKAQRAFVNWLLA-Aib-GPSSGAPPS-NH$_2$ (SEQ ID NO: 120) |
| 30 | Hy-Y-Aib-EGTFTSDYSIYLEKAAKEFVNWLLAQK-NH$_2$ (SEQ ID NO: 121) |
| 31 | Hy-Y-Aib-EGTFTSDYSIYLDK-K(15-carboxy-pentadecanoyl-isoGlu)-AQRAFVNWLLA-Aib-K-NH$_2$ (SEQ ID NO: 122) |
| 32 | Hy-Y-Aib-EGTFTSDYSI-Aib-LDK-K(Hexadecanoyl-isoGlu)-AQRAFVEWLLAQGPSSGAPPPS-NH$_2$ (SEQ ID NO: 123) |
| 33 | Hy-Y-Aib-EGTFTSDYSIYLDK-K(hexadecanoyl-isoGlu)-AQRAFVEWLLAQGPSSGAPPPS-NH$_2$ (SEQ ID NO: 124) |
| 34 | Hy-Y-Aib-EGTFTSDYSIYLDE-K(hexadecanoyl-isoGlu)-AAKEFIEWLESA-NH$_2$ (SEQ ID NO: 125) |
| 35 | Hy-Y-Aib-EGTFTSDYSIYLDK-K(hexadecanoyl-isoGlu)-AQRAFVNWLLA-Aib-KPSSGAPPPS-NH$_2$ (SEQ ID NO: 126) |
| 36 | Hy-Y-Aib-EGTFTSDYSIALDK-K(hexadecanoyl-isoGlu)-AQRAFVNWLVA-Aib-KPSSGAPPPS-NH$_2$ (SEQ ID NO: 127) |
| 37 | Hy-Y-Aib-EGTFTSDYSIYLE-KKAAKDFVEWLLSA-NH$_2$ (SEQ ID NO: 128) |
| 38 | Hy-Y-Aib-EGTFTSDYSIYLE-KKAAHDFVEWLLSA-NH$_2$ (SEQ ID NO: 129) |
| 39 | Hy-Y-Aib-EGTFTSDYSIYLEKKAQKEFVEWLLSA-NH$_2$ (SEQ ID NO: 130) |
| 40 | Hy-Y-Aib-EGTFTSDYSIYLDEKAAKDFVEWLLSA-NH$_2$ (SEQ ID NO: 131) |
| 41 | Hy-Y-Aib-EGTFTSDYSIYLESKAAHDFVEWLLSA-NH$_2$ (SEQ ID NO: 132) |
| 42 | Hy-Y-Aib-EGTFTSDYSIYLDKKAAHDFVEWLLSA-NH$_2$ (SEQ ID NO: 133) |
| 43 | Hy-Y-Aib-EGTFTSDYSIYLEKKAAKEFVEWLLSA-NH$_2$ (SEQ ID NO: 134) |
| 44 | Hy-Y-Aib-EGTFTSDYSIYLDSKAAHDFVEWLLRA-NH$_2$ (SEQ ID NO: 135) |
| 45 | Hy-Y-Aib-EGTFTSDYSKYLDS-K(Hexadecanoyl-isoGlu)-AAHDFVEWLLSA-NH$_2$ (SEQ ID NO: 136) |
| 46 | Hy-Y-Aib-EGTFTSDYSIYLEK-K(Hexadecanoyl-isoGlu)-AAKEFVEWLLSA-NH$_2$ (SEQ ID NO: 137) |

TABLE 2-continued

| Compound No. | Sequence |
|---|---|
| 47 | Hy-Y-Aib-EGTFTSDYSIYLDS-K(Hexadecanoyl-isoGlu)-AAHDFVEWLLRA-NH$_2$ (SEQ ID NO: 138) |
| 48 | Hy-Y-Aib-EGTFTSDYSIYLDE-K(Hexadecanoyl-isoGiu)-AAKDFVEWLESA-NH$_2$ (SEQ ID NO: 139) |
| 49 | Hy-Y-Aib-EGTFTSDYSKYLDE-K(Hexadecanoyl-isoGlu)-AAKDFIEWLESA-NH$_2$ (SEQ ID NO: 140) |
| 50 | Hy-Y-Aib-EGTFTSDYSIYLDE-K(Hexadecanoyl-isoGlu)-AAKDFIEWLESA-NH$_2$ (SEQ ID NO: 141) |
| 51 | Hy-Y-Aib-EGTFTSDYSKYLDS-K(Hexadecanoyl-isoGlu)-AAHDFVEWLLRA-NH$_2$ (SEQ ID NO: 142) |
| 52 | Hy-Y-Aib-EGTFTSDYSIYLDE-K(Hexadecanoyl-isoGlu)-AAKDFVEWLLSA-NH$_2$ (SEQ ID NO: 143) |
| 53 | Hy-Y-Aib-EGTFTSDYSIYLDS-K(Hexadecanoyl-isoGlu)-AAHDFVEWLLSAGPSSGAPPPS-NH$_2$ (SEQ ID NO: 144) |
| 54 | Hy-Y-Aib-EGTFTSDYSIYLEK-K-(Hexadecanoyl-isoGlu)-AAKEFVEWLLSAGPSSGAPPPS-NH$_2$ (SEQ ID NO: 145) |
| 55 | Hy-Y-Aib-EGTFTSDYSIYLDSKAAHDFVEWLLSAGPSSGAPPPS-NH$_2$ (SEQ ID NO: 146) |
| 56 | Y-Aib-EGTFTSDYSIYLDE-K(Hexadecanoyl-isoGlu)-AAHDFVEWLLSA (SEQ ID NO: 147) |

Synthesis of Compound No. 36

Solid phase peptide synthesis was performed on a CEM Liberty Peptide Synthesizer using standard Fmoc chemistry. TentaGel S Ram S resin (1.05 g; 0.25 mmol/g) was swelled in DMF (10 ml) prior to use and transferred between tube and reaction vessel using DCM and DMF.

Coupling

An Fmoc-amino acid in DMF/DCM (2:1; 0.2 M; 5 ml) was added to the resin in a CEM Discover microwave unit together with COMU/DMF (0.5 M; 2 ml) and DIPEA&DMF (2.0 M; 1 ml). The coupling mixture was heated to 75° C. for 5 min while nitrogen was bubbled through the mixture. The resin was then washed with DMF (4×10 ml). Fmoc-Tyr(OtBu)-Ser(Psi Me,Me)-OH pseudoproline was used for amino acid number 29 and 30 counting from the C-terminal. Fmoc-Lys(hexadecanoyl-gamma-Glu)-OH (2:1; 0.2 M; 5 ml) was incorporated as a premade building block using standard Fmoc coupling chemistry. The first 9 amino acids and amino acid number 24 (counting from the C-terminal) was double couple meaning the building block was coupled twice before deprotection.

Deprotection

Piperidine/DMF (20%; 10 ml) was added to the resin for initial deprotection and the mixture was heated by microwaves (30 sec; 40° C.). The reaction vessel was drained and a second portion of piperidine/DMF (20%; 10 ml) was added and heated (75° C.; 3 min.) again. The resin was then washed with DMF (6×10 ml).

The resin was washed with EtOH (3×10 ml) and Et2O (3×10 ml) and dried to constant weight at room temperature (r.t.). The crude peptide was cleaved from the resin by treatment with TFA/TIS/H$_2$O (95/2.5/2.5; 60 ml, 2 h; r.t.). Most of the TFA was removed at reduced pressure and the crude peptide was precipitated and washed three times with diethylether and dried to constant weight at room temperature.

HPLC Purification of the Crude Peptide

The crude peptide was first purified to 45% by preparative reverse phase HPLC using a PerSeptive Biosystems VISION Workstation equipped with a Gemini NX 5µ C-18 110A, 10×250 mm column and a fraction collector and run at 35 ml/min with a gradient of buffer A (0.1% TFA, aq.) and buffer B (0.1% TFA, 90% MeCN, aq.). Fractions were analyzed by analytical HPLC and MS and relevant fractions were pooled and lyophilized. The product (138 mg) was analysed to give a purity of 96% as characterized by HPLC and MS. Calculated monoisotopic mass=4534, 42, found 4534, 43.

Example 2

Human GIP Receptor (GIP R) and GLP-1 Receptor (GLP-1 R) Activity Assay

In vitro effects of peptide conjugates of the invention were assessed by measuring the induction of cAMP following stimulation of the respective receptor by GIP, GLP1 or analogues of these, as outlined in the invention, using the AlphaSceen® cAMP kit from Perkin-Elmer according to instructions. Briefly. HEK293 cells expressing the human GIP R or GLP-1 R (stable cell lines generated through transfection of the cDNA for human GIP R or GLP-1 and selection of stable clones) were seeded at 30,000 cells/well in 96-well microtiter plates coated with 0.01% poly-L-lysine, and grown for 1 day in culture in 200 µl growth medium (DMEM, 10% FCS, Penicillin (100 IU/ml), Streptomycin (100 µg/ml)). On the day of analysis, growth medium was removed and the cells were washed once with 150 ml Tyrode's buffer (Tyrode's Salts (9.6 g/l), 10 mM HEPES, pH 7.4). Cells were then incubated in 100 ml Assay buffer (0.1% W/V Alkali-treated Casein and 100 µM IBMX in Tyrode's Buffer) containing increasing concentrations of control and test compounds for 15 min at 37° C. The Assay buffer was removed and cells are lysed in 80 µl Lysis buffer (0.1% w/v BSA, 5 mM HEPES, 0.3% v/v Tween-20) per well. From each well 10 µl lysed cells was transferred to a 384-well plate and mixed with 15 µl bead-mix (1 Unit/15 µl anti-cAMP Acceptor Beads, 1 Unit/15 µl Donor Beads, and 1 Unit/15 µl Biotinylated cAMP in Assay Buffer). The plates were mixed and incubated in the dark for an hour at room temperature before measuring using an Envision™ plate reader (Perkin-Elmer). The results are summarized in Table 3.

TABLE 3

EC$_{50}$ average values of the compounds on the GIP-R and GLP1-R compared to control peptides.

| Compound No | GIP R (EC$_{50}$ in nM) | GLP1 R (EC$_{50}$ in nM) |
|---|---|---|
| hGIP | 0.0038 | |
| Exendin-4 | | 0.0043 |
| 2 | 0.0068 | 0.015 |
| 3 | 0.015 | 0.022 |
| 4 | 0.022* | 2.6 |
| 5 | 0.031 | 0.023 |
| 6 | 0.27 | 0.97 |
| 7 | 0.21 | 0.024 |
| 8 | 0.10 | 0.029 |
| 9 | 0.091 | 0.014 |
| 11 | 0.76 | 0.47 |
| 12 | 0.050 | 0.010 |
| 13 | 0.14 | 0.032 |
| 14 | 0.036 | 0.0087 |
| 15 | 0.060 | 0.010 |
| 16 | 0.053 | 0.012 |
| 17 | 0.021 | 0.0074 |
| 18 | 0.36 | 0.015 |
| 19 | 0.015 | 0.0073 |
| 20 | 0.049 | 0.0090 |
| 21 | 0.080 | 0.0090 |
| 23 | 0.42 | 0.012 |
| 24 | 0.096 | 0.0085 |
| 25 | 0.12 | 0.041 |
| 26 | 0.80 | 0.39 |
| 27 | 0.30 | 0.074 |
| 28 | 0.020 | 0.0051 |
| 29 | 0.024 | 0.0088 |
| 30 | 0.054 | 0.0093 |
| 31 | 0.022 | 0.020 |
| 32 | 0.012 | 0.018 |
| 33 | 0.035 | 0.031 |
| 34 | 0.045 | 0.031 |
| 35 | 0.028 | 0.022 |
| 36 | 0.0099 | 0.015 |
| 37 | 0.0097 | 0.018 |
| 38 | 0.0070 | 0.018 |
| 39 | 0.0083 | 0.011 |
| 40 | 0.011 | 0.022 |
| 41 | 0.013 | 0.011 |
| 42 | 0.0070 | 0.012 |
| 43 | 0.0091 | 0.017 |
| 44 | 0.016 | 0.013 |
| 45 | 0.32 | 0.11 |
| 46 | 0.088 | 0.048 |
| 47 | 0.096 | 0.14 |
| 48 | 0.061 | 0.041 |
| 49 | 0.092 | 0.049 |
| 50 | 0.053 | 0.090 |
| 51 | 0.24 | 0.11 |
| 52 | 0.087 | 0.18 |
| 53 | 0.062 | 0.092 |
| 54 | 0.037 | 0.033 |
| 55 | 0.0071 | 0.0087 |
| 56 | 0.14 | 0.13 |

*Value is slightly adjusted from that in U.S. application Ser. No. No. 61/642,439 due to additional determinations. All values are based on multiple determinations.

Example 3

Pharmacokinetics of Compounds 32 and 33 in Mice

Method

C57BL/6J mice were given a single subcutaneous dose of 200 nmol/kg body weight of each peptide to be tested. Blood samples were drawn 0.5, 2, 4, 6, 8, 16, 24 and 36 hours post-dose by sublingual bleeding. At each time point, samples from two mice were taken, i.e. 16 mice per compound. The mice were euthanized immediately after blood sampling by cervical dislocation. Plasma samples were analyzed after solid phase extraction (SPE) by liquid chromatography mass spectrometry (LC-MS/MS). The pharmacokinetic analyses were performed by using the non-compartmental approach (see Table 4).

TABLE 4

Terminal elimination half-life (h) in mice following subcutaneous administration of 200 nmol/kg body weight.

| Compound | T$_{1/2}$ (h) |
|---|---|
| 32 | 3.4 |
| 33 | 3.7 |

Example 4

IPGTT (Intraperitoneal Glucose Tolerance Test) in Mice

Male C57BL/6J mice (Charles River, Germany) were maintained on normal chow (Altromin 1324, Brogaarden A/S, Gentofte, Denmark) and domestic quality water with added citric acid to pH~3.6. The animals were housed pair-wise in a light-, temperature-, and humidity-controlled room (12:12 h light-dark cycle, with lights on at 06.00-18.00 hr; 20-22° C.; 50-80% relative humidity). Mice were fasted for 5 hr before the IPGTT. Peptides and vehicle were administered subcutaneously before the intraperitoneal injection of glucose (t=0 min; 2 g/kg; 5 ml/kg). Tail vein blood was sampled at time t=0 (before glucose administration), 15, 30, 45, 60, 90, and 120 min for measurements of blood glucose. Results are shown in FIG. 1.

Example 5

Sub-Chronic Effects of GIP-GLP-1 Receptor Dual Acting Agonist on Body Weight, Body Composition, Food Intake, Blood, Glucose, Plasma Insulin, Cholesterol and Triglycerides in Diet-Induced Obese C57BL/6J Mice Male C57BL/6J mice (obtained from Jackson Labs, USA) fed high-fat diet (60% of total energy from fat, D12492, Research Diet Inc.) for approximately 6 months were used. The mice were housed individually, and they were maintained on a 12:12 hour light-dark cycle (lights on at 05.00-17.00). All mice were mock-treated (once daily s.c. injection of vehicle) for a week to acclimatize the animals to handling and injections. Subsequently, the mice were stratified according to body fat mass (measured by magnetic resonance technique) and body weight into five groups (n=10). Animals were thereafter treated twice daily with s.c. injections (5 ml/kg) of vehicle (group 1: 50 mM phosphate buffer, pH 7.5), the GLP-1 analogue liraglutide (group 2: 2*25 nmol/kg), or test substance (group 3, 2*5 nmol/kg; group 4, 2*25 nmol/kg, or group 5, 2*100 nmol/kg) for a total of 21 days. The daily injections were given in the morning (at 8.00-9.00) and in the afternoon (15.00-16.00 hr). Body weight, food and water intake were determined daily throughout the study. On day 8 of treatment, the 2*100 nmol/kg dose of test substance was halved due to profound body weight loss. This dose (2*50 nmol/kg) was used throughout the remaining treatment period. On day 13, animals were fasted for 4 hours, and blood samples were taken for measurements of blood glucose and plasma insulin. The animals were not dosed in the morning before the blood sampling. On day 19, body composition was measured using a MR scanner. On day 21, blood was sampled for measurements of blood glucose, plasma insulin, plasma cholesterol, and plasma triglycerides. Animals were injected with vehicle, liraglutide or test substance 2 hours before blood sampling. After the final blood sampling, the mice were euthanized.

Statistical analyses were performed using Graph Pad Prism version 5. The measured parameters were compared using one-way or two-way ANOVAs followed by Tukey's multiple comparison tests or Bonferroni post tests. Student's two-tailed, unpaired t-test was used to compare the means of two independent groups. Differences were considered statistically significant at $p<0.05$.

The invention claimed is:

1. A GIP analogue represented by the general formula I':

(I')
(SEQ ID NO: 61)
$R^1$-Tyr-X2-X3-Gly-Thr-Phe-X7-Ser-X9-X10-X11-X12-X13-X14-X15-X16-Lys-Ala-X19-X20-X21-X22-X23-X24-Trp-Leu-X27-X28-X29-X30-X31-X32-X33-X34-X35-X36-X37-X38-X39-X40-X41-X42-$R^2$ or a pharmaceutically acceptable salt thereof,
wherein
$R^1$ is Hy-, Ac or pGlu;
X2 is Ala, Aib or Gly;
X3 is Glu or Asp;
X7 is Thr, Ser, or Ile;
X9 is Asp or Glu;
X10 is Tyr, Leu or Ser;
X11 is Ser or Leu;
X12 is Ile or Lys;
X13 is Ala, Tyr or Aib;
X14 is Met, Leu or Ser;
X15 is Asp or Glu;
X16 is Lys, Gly, Ser or Glu;
X19 is Gln, Ala, Glu or Lys;
X20 is Gln, Lys, Arg or His;
X21 is Asp, Ala or Glu;
X22 is Phe or 1Nal;
X23 is Val, Ile or Leu;
X24 is Asn, Glu, Arg or Lys;
X27 is Leu, Val, Ile, Lys, Glu or Ser;
X28 is Ala, Ser, Arg or Aib;
X29 is Gln, Aib, Lys, Gly or Ala;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;

X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
R² is —NH2 or —OH.

2. The GIP analogue of claim 1, wherein the GIP analogue is represented by the general Formula I(b)':

```
(I(b)')                                    (SEQ ID NO: 63)
R¹-Tyr-X2-X3-Gly-Thr-Phe-X7-Ser-X9-X10-X11-X12-
X13-X14-X15-X16-Lys-Ala-X19-X20-X21-Phe-X23-X24-
Trp-Leu-X27-X28-X29-X30-X31-X32-X33-X34-X35-X36-
X37-X38-X39-X40-X41-X42-R²
``` or a pharmaceutically acceptable salt thereof,
wherein
R1 is Hy-, Ac or pGlu;
X2 is Ala, Aib or Gly;
X3 is Glu or Asp;
X7 is Thr or Ser;
X9 is Asp or Glu;
X10 is Tyr or Leu;
X11 is Ser or Leu;
X12 is Ile or Lys;
X13 is Ala, Tyr or Aib;
X14 is Leu or Ser;
X15 is Asp or Glu;
X16 is Lys, Ser or Glu;
X19 is Gln, Ala, Glu or Lys;
X20 is Gln, Lys, Arg or His;
X21 is Asp, Ala or Glu;
X23 is Val, Ile or Leu;
X24 is Asn, Glu, Arg or Lys;
X27 is Leu, Glu, Val or Ile;
X28 is Ala, Ser, Arg or Aib;
X29 is Gln, Gly, Aib or Ala;
X30 is Lys, Gly, Pro or absent;
X31 is Gly, Pro, Ser, Glu or absent;
X32 is Lys, Ser or absent;
X33 is Lys, Ser, Glu or absent;
X34 is Asn, Gly, Ala, Lys or absent;
X35 is Asp, Ala, Pro, Glu or absent;
X36 is Trp, Pro, Lys or absent;
X37 is Lys, Pro, Glu or absent;
X38 is His, Pro, Ser, Lys or absent;
X39 is Asn, Ser or absent;
X40 is Ile or absent;
X41 is Thr or absent;
X42 is Gln or absent; and
R² is —NH₂ or —OH.

3. A GIP analogue represented by the general Formula II':

```
(II')                                      (SEQ ID NO: 64)
R¹-Tyr-X2-Glu-Gly-Thr-Phe-X7-Ser-Asp-X10-X11-
X12-X13-Leu-X15-X16-Lys-Ala-X19-X20-X21-Phe-X23-
X24-Trp-Leu-X27-X28-X29-X30-Y1-R²
``` or a pharmaceutically acceptable salt thereof,
wherein
R1 is Hy-, Ac or pGlu;
X2 is Aib or Gly;
X7 is Thr, Ile or Ser;
X10 is Tyr or Leu;
X11 is Ser or Leu;
X12 is Ile or Lys;
X13 is Ala, Tyr or Aib;
X15 is Asp or Glu;
X16 is Ser, Glu or Lys;
X17 is Ile or Lys;
X19 is Gln or Ala;
X20 is Lys, His or Arg;
X21 is Ala, Asp or Glu;
X23 is Val or Ile;
X24 is Asn, Lys or Glu;
X27 is Leu, Glu, Val or Ile;
X28 is Aib, Ala, Ser or Arg;
X29 is Gln, Aib, Ala, Gly or Lys;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
R² is —NH₂ or —OH.

4. The GIP analogue of claim 3, wherein the GIP analogue is represented by the general Formula II(a)':

```
(II9a)')                                   (SEQ ID NO: 65)
R¹-Tyr-X2-Glu-Gly-Thr-Phe-X7-Ser-Asp-X10-X11-Ile-
X13-Leu-X15-X16-Lys-Ala-X19-X20-X21-Phe-X23-X24-
Trp-Leu-X27-X28-X29-X30-Y1-R²
``` wherein
R¹ is Hy-, Ac or pGlu;
X2 is Aib or Gly;
X7 is Thr, Ile or Ser;
X10 is Tyr or Leu;
X11 is Ser or Leu;
X13 is Ala, Tyr or Aib;
X15 is Asp or Glu;
X16 is Ser, Glu or Lys;
X19 is Gln or Ala;
X20 is Lys, His or Arg;
X21 is Ala, Asp or Glu;
X23 is Val or Ile;
X24 is Asn, Lys or Glu;
X27 is Leu, Glu, Val or Ile;
X28 is Aib, Ala, Ser or Arg;
X29 is Gln, Aib, Ala or Gly;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
R² is —NH₂ or —OH.

5. The GIP analogue of claim 4, wherein the GIP analogue is represented by the general Formula II(b)':

```
(II(b)')                                   (SEQ ID NO: 66)
R¹-Tyr-Aib-Glu-Gly-Thr-Phe-X7-Ser-Asp-Tyr-Ser-Ile-
X13-Leu-X15-X16-Lys-Ala-Gln-X20-X21-Phe-X23-Glu-
Trp-Leu-X27-X28-Ala-X30-Y1-R²
``` or a pharmaceutically acceptable salt thereof,
wherein
R¹ is Hy-, Ac or pGlu;
X7 is Thr or Ser;

215

X13 is Ala or Tyr;
X15 is Asp or Glu;
X16 is Lys, Glu or Ser;
X20 is Lys, His or Arg;
X21 is Ala, Asp or Glu;
X23 is Val or Ile;
X27 is Leu, Glu or Val;
X28 is Arg or Ser;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —$NH_2$ or —OH.

6. The GIP analogue of claim 4, wherein the GIP analogue is represented by the general Formula II(c)':

```
(II(c)')
                                      (SEQ ID NO: 67)
R¹-Tyr-Aib-Glu-Gly-Thr-Phe-X7-Ser-Asp-Tyr-Ser-
Ile-X13-Leu-X15-X16-Lys-Ala-Gln-X20-X21-Phe-Val-
X24-Trp-Leu-X27-Ala-X29-X30-Y1-R²
``` or a pharmaceutically acceptable salt thereof,
wherein
$R^1$ is Hy-, Ac or pGlu;
X7 is Thr or Ser;
X13 is Ala, Aib or Tyr;
X15 is Asp or Glu;
X16 is Glu, Lys or Ser;
X20 is Lys, His or Arg;
X21 is Ala, Asp or Glu;
X24 is Glu or Asn;
X27 is Leu, Glu or Val;
X29 is Gln or Aib;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —$NH_2$ or —OH.

7. The GIP analogue of claim 4, wherein the GIP analogue is represented by the general Formula II(d)':

```
(II(d)')
                                      (SEQ ID NO: 68)
R¹-Tyr-Aib-Glu-Gly-Thr-Phe-X7-Ser-Asp-Tyr-Ser-
Ile-X13-Leu-X15-X16-Lys-Ala-Gln-X20-Ala-Phe-Val-
Glu-Trp-Leu-X27-Ala-Gln-X30-Y1-R²
``` or a pharmaceutically acceptable salt thereof,
wherein
$R^1$ is Hy-, Ac or pGlu;
X7 is Thr or Ser;
X13 is Ala, Aib or Tyr;
X15 is Asp or Glu;
X16 is Glu, Lys or Ser;
X20 is Lys, His or Arg;
X27 is Leu, Glu or Val;
X30 is Lys, Gly or absent;
Y1 is Gly-Pro-Ser-Ser-Gly-Ala-Pro-Pro-Pro-Ser (SEQ ID NO:74), Gly-Pro-Ser-Ser-Gly-Ala-Pro-Pro-Ser (SEQ ID NO:75), Pro-Ser-Ser-Gly-Ala-Pro-Pro-Pro-Ser (SEQ ID NO:76), Pro-Ser-Ser-Gly-Ala-Pro-Pro-Ser (SEQ ID NO:77) or absent; and
$R^2$ is —$NH_2$ or —OH.

216

8. A GIP analogue of claim 1, wherein the amino acid sequence X1-X29 has no more than 6 amino acid differences from the sequence
Y-Aib-EGTFTSDYSIYLDKKAQRAFVEWLLAQ (SEQ ID NO: 70).

9. A GIP analogue of claim 1, wherein the amino acid sequence X1-X29 has no more than 6 amino acid differences from the sequence Y-Aib-EGTFTSDYSIYLEK-KAAKEFVEWLLSA (SEQ ID NO: 71).

10. A GIP analogue of claim 1, wherein the amino acid sequence X1-X29 has no more than 5 amino acid differences from sequence
Y-Aib-EGTFTSDYSIYLDEKAAKEFIEWLESA (SEQ ID NO: 72).

11. A GIP analogue according to claim 1, wherein X24 is Glu and/or X21 is Ala.

12. A GIP analogue according to claim 1, wherein X7 is Thr and X14 is Leu.

13. A GIP analogue according to claim 1, wherein X7 is Thr, X14 is Leu and X18 is Ala.

14. A GIP analogue according to claim 1, wherein X2 is Aib, X7 is Thr and X14 is Leu.

15. A GIP analogue according to claim 1, wherein X2 is Aib, X7 is Thr, X14 is Leu and X13 and/or X29 is Aib.

16. A GIP analogue according to claim 1, wherein X2 is Aib, X7 is Thr, X14 is Leu and X24 is Glu.

17. A GIP analogue according to claim 1, wherein X2 is Aib, X7 is Thr, X14 is Leu, X24 is Glu and X29 is Gln.

18. A GIP analogue according to claim 1, wherein X2 is Aib, X7 is Thr, X14 is Leu, X21 is Ala, X24 is Glu and X29 is Gln.

19. A GIP analogue according to claim 1, wherein X2 is Aib, X7 is Thr, X14 is Leu, X24 is Glu, X27 is Leu and X28 is Ser.

20. A GIP analogue according to claim 1, wherein X2 is Aib, X7 is Thr, X14 is Leu, X24 is Glu, X27 is Glu and X28 is Ser.

21. A GIP analogue according to claim 1, wherein X2 is Aib, X7 is Thr, X14 is Leu, X20 is His, X24 is Glu, X27 is Leu and X28 is Ser.

22. A GIP analogue according to claim 1 selected from:

```
                                      (SEQ ID NO: 94)
Hy-Y-Aib-EGTFISDYSIYLEKKAAKEFVNWLLAQK-NH₂
(Compound 1);

(SEQ ID NO: 95)
Hy-Y-Aib-EGTFTSDYSI-Aib-
LDKKAQRAFVEWLLAQGPSSGAPPPS-NH₂(Compound 2);

(SEQ ID NO: 98)
Hy-Y-Aib-EGTFTSDYSIYLDKKAQRAFVNWLLA-Aib-K-
NH₂ (Compound 5);

(SEQ ID NO: 99)
pGlu-YAEGTFTSDYSIYLDKKAQRAFVNWLLA-Aib-K-
NH₂ (Compound 6);

(SEQ ID NO: 100)
Hy-YGEGTFTSDYSIYLDKKAQRAFVNWLLA-Aib-K-
NH₂ (Compound 7);

(SEQ ID NO: 101)
Hy-Y-Aib-EGTFSSDYSIYLDKKAQRAFVNWLLA-Aib-K-
NH₂ (Compound 8);

(SEQ ID NO: 102)
Hy-Y-Aib-EGTFTSDLSIYLDKKAQRAFVNWLLA-Aib-K-
NH₂ (Compound 9);
```

```
Hy-Y-Aib-EGTFTSDYLIYLDKKAQRAFVNWLLA-Aib-K-
NH2 (Compound 11);
                                      (SEQ ID NO: 103)

Hy-Y-Aib-EGTFTSDYSIALDKKAQRAFVNWLLA-Aib-K-
NH2 (Compound 12);
                                      (SEQ ID NO: 104)

Hy-Y-Aib-EGTFTSDYSIYSDKKAQRAFVNWLLA-Aib-K-
NH2 (Compound 13);
                                      (SEQ ID NO: 105)

Hy-Y-Aib-EGTFTSDYSIYLEKKAQRAFVNWLLA-Aib-K-
NH2 (Compound 14);
                                      (SEQ ID NO: 106)

Hy-Y-Aib-EGTFTSDYSIALEKKAQRAFVNWLLA-Aib-K-
NH2 (Compound 15);
                                      (SEQ ID NO: 107)

Hy-Y-Aib-EGTFTSDYSIYLDSKAQRAFVNWLLA-Aib-K-
NH2 (Compound 16);
                                      (SEQ ID NO: 108)

Hy-Y-Aib-EGTFTSDYSIYLDEKAQRAFVNWLLA-Aib-K-
NH2 (Compound 17);
                                      (SEQ ID NO: 109)

Hy-Y-Aib-EGTFTSDYSIYLDSKAKRAFVNWLLA-Aib-K-
NH2 (Compound 18);
                                      (SEQ ID NO: 110)

Hy-Y-Aib-EGTFTSDYSIYLDKKAQKEFVNWLLA-Aib-K-
NH2 (Compound 19);
                                      (SEQ ID NO: 111)

Hy-Y-Aib-EGTFTSDYSIYLDKKAQRAFVKWLLA-Aib-
K-NH2 (Compound 20);
                                      (SEQ ID NO: 112)

Hy-Y-Aib-EGTFTSDYSIYLDKKAQRAFVNWLVA-Aib-
K-NH2 (Compound 21);
                                      (SEQ ID NO: 113)

Hy-Y-Aib-EGTFTSDYSIYLDKKAQRAFVNWLKA-Aib-
K-NH2 (Compound 23);
                                      (SEQ ID NO: 114)

Hy-Y-Aib-EGTFTSDYSIYLDKKAQRAFVNWLL-Aib-K-
NH2 (Compound 24);
                                      (SEQ ID NO: 115)

Hy-Y-Aib-EGTFTSDYSIYLDKKAEKAFVNWLLA-Aib-K-
NH2 (Compound 27);
                                      (SEQ ID NO: 118)

Hy-Y-Aib-EGTFTSDYSIYLDKKAQRAFVNWLLA-Aib-
GPSSGAPPPS-NH2 (Compound 28);
                                      (SEQ ID NO: 119)

Hy-Y-Aib-EGTFTSDYSIYLDKKAQRAFVNWLLA-Aib-
GPSSGAPPS-NH2 (Compound 29);
                                      (SEQ ID NO: 120)

Hy-Y-Aib-EGTFTSDYSIYLEKKAAKEFVNWLLAQK-
NH2 (Compound 30);
                                      (SEQ ID NO: 121)

Hy-Y-Aib-EGTFTSDYSIYLDK-K(15-carboxy-
pentadecanoyl-isoGlu)-AQRAFVNWLLA-Aib-
K-NH2 (Compound 31);
                                      (SEQ ID NO: 122)

Hy-Y-Aib-EGTFTSDYSI-Aib-LDK-K(Hexadecanoyl-
isoGlu)-AQRAFVEWLLAQGPSSGAPPPS-NH2(Compound 32);
                                      (SEQ ID NO: 123)

Hy-Y-Aib-EGTFTSDYSIYLDK-K(hexadecanoyl-isoGlu)-
AQRAFVEWLLAQGPSSGAPPPS-NH2(Compound 33);
                                      (SEQ ID NO: 124)

Hy-Y-Aib-EGTFTSDYSIYLDE-K(hexadecanoyl-isoGlu)-
AAKEFIEWLESA-NH2(Compound 34);
                                      (SEQ ID NO: 125)

Hy-Y-Aib-EGTFTSDYSIYLDK-K(hexadecanoyl-isoGlu)-
AQRAFVNWLLA-Aib-KPSSGAPPPS-NH2(Compound 35);
                                      (SEQ ID NO: 126)

Hy-Y-Aib-EGTFTSDYSIALDK-K(hexadecanoyl-isoGlu)-
AQRAFVNWLVA-Aib-KPSSGAPPPS-NH2 (Compound 36);
                                      (SEQ ID NO: 127)

Hy-Y-Aib-EGTFTSDYSIYLE-KKAAKDFVEWLLSA-NH2
(Compound 37);
                                      (SEQ ID NO: 128)

Hy-Y-Aib-EGTFTSDYSIYLE-KKAAHDFVEWLLSA-NH2
(Compound 38);
                                      (SEQ ID NO: 129)

Hy-Y-Aib-EGTFTSDYSIYLEKKAQKEFVEWLLSA-NH2
(Compound 39);
                                      (SEQ ID NO: 130)

Hy-Y-Aib-EGTFTSDYSIYLDEKAAKDFVEWLLSA-NH2
(Compound 40);
                                      (SEQ ID NO: 131)

Hy-Y-Aib-EGTFTSDYSIYLESKAAHDFVEWLLSA-NH2
(Compound 41);
                                      (SEQ ID NO: 132)

Hy-Y-Aib-EGTFTSDYSIYLDKKAAHDFVEWLLSA-NH2
(Compound 42);
                                      (SEQ ID NO: 133)

Hy-Y-Aib-EGTFTSDYSIYLEKKAAKEFVEWLLSA-NH2
(Compound 43);
                                      (SEQ ID NO: 134)

Hy-Y-Aib-EGTFTSDYSIYLDSKAAHDFVEWLLRA-NH2
(Compound 44);
                                      (SEQ ID NO: 135)

Hy-Y-Aib-EGTFTSDYSKYLDS-K(Hexadecanoyl-isoGlu)-
AAHDFVEWLLSA-NH2 (Compound 45);
                                      (SEQ ID NO: 136)

Hy-Y-Aib-EGTFTSDYSIYLEK-K(Hexadecanoyl-isoGlu)-
AAKEFVEWLLSA-NH2(Compound 46);
                                      (SEQ ID NO: 137)

Hy-Y-Aib-EGTFTSDYSIYLDS-K(Hexadecanoyl-isoGlu)-
AAHDFVEWLLRA-NH2 (Compound 47);
                                      (SEQ ID NO: 138)

Hy-Y-Aib-EGTFTSDYSIYLDE-K(Hexadecanoyl-isoGlu)-
AAKDFVEWLESA-NH2 (Compound 48);
                                      (SEQ ID NO: 139)

Hy-Y-Aib-EGTFTSDYSKYLDE-K(Hexadecanoyl-isoGlu)-
AAKDFIEWLESA-NH2 (Compound 49);
                                      (SEQ ID NO: 140)

Hy-Y-Aib-EGTFTSDYSIYLDE-K(Hexadecanoyl-isoGlu)-
AAKDFIEWLESA-NH2 (Compound 50);
                                      (SEQ ID NO: 141)

Hy-Y-Aib-EGTFTSDYSKYLDS-K(Hexadecanoyl-isoGlu)-
AAHDFVEWLLRA-NH2 (Compound 51);
                                      (SEQ ID NO: 142)

Hy-Y-Aib-EGTFTSDYSIYLDE-K(Hexadecanoyl-isoGlu)-
AAKDFVEWLLSA-NH2(Compound 52);
                                      (SEQ ID NO: 143)

Hy-Y-Aib-EGTFTSDYSIYLDS-K(Hexadecanoyl-isoGlu)-
AAHDFVEWLLSAGPSSGAPPPS-NH2 (Compound 53);
                                      (SEQ ID NO: 144)
```

-continued

```
                                              (SEQ ID NO: 145)
Hy-Y-Aib-EGTFTSDYSIYLEK-K-(Hexadecanoyl-isoGlu)-
AAKEFVEWLLSAGPSSGAPPPS-NH2(Compound 54);
and
                                              (SEQ ID NO: 146)
Hy-Y-Aib-EGTFTSDYSIYLDSKAAHDFVEWLLSAGPSSGAPPPS-
NH2 (Compound 55);
and
                                              (SEQ ID NO: 147)
Hy-Y-Aib-EGTFTSDYSIYLDE-K(Hexadecanoyl-isoGlu)-
AAHDFVEWLLSA-NH2 (Compound 57),
``` or a pharmaceutically acceptable salt thereof.

23. A GIP analogue according to claim 1 with a lipophilic substituent conjugated to one or more of positions 15, 16, 17, 19, 20, 24, 27, 28 and 30.

24. A pharmaceutical composition comprising a GIP analogue of claim 1, or a salt thereof, in admixture with a carrier.

25. The pharmaceutical composition of claim 24, wherein the GIP analogue is a pharmaceutically acceptable acid addition salt.

26. The pharmaceutical composition of claim 24, which is formulated as a liquid suitable for administration by injection or infusion, or which is formulated to cause slow release of said GIP analogue.

27. A therapeutic kit comprising a GIP analogue according to claim 1, optionally in combination with a pharmaceutically acceptable carrier.

28. A device comprising a GIP analogue according to claim 1, for delivery of the GIP analogue to a subject.

* * * * *